(12) United States Patent
White et al.

(10) Patent No.: US 8,298,289 B2
(45) Date of Patent: Oct. 30, 2012

(54) SUTURE-BASED ORTHOPEDIC JOINT DEVICE DELIVERY METHODS

(75) Inventors: David White, Atherton, CA (US); Janine C. Robinson, Half Moon Bay, CA (US); Michael Hogendijk, Mountain View, CA (US)

(73) Assignee: Articulinx, Inc., Cupertino, CA (US)

( * ) Notice: Subject to any disclaimer, the term of this patent is extended or adjusted under 35 U.S.C. 154(b) by 289 days.

(21) Appl. No.: 12/210,099

(22) Filed: Sep. 12, 2008

(65) Prior Publication Data
US 2009/0012617 A1    Jan. 8, 2009

(51) Int. Cl.
*A61F 2/42* (2006.01)
(52) U.S. Cl. .................................................. 623/21.11
(58) Field of Classification Search ............... 623/13.12, 623/21.11
See application file for complete search history.

(56) References Cited

U.S. PATENT DOCUMENTS

| | | | |
|---|---|---|---|
| 4,781,190 A | 11/1988 | Lee | |
| 5,344,459 A | 9/1994 | Swartz | |
| 5,505,735 A | 4/1996 | Li | |
| 5,716,416 A | 2/1998 | Lin | |
| 6,007,580 A | 12/1999 | Lehto et al. | |
| 6,017,366 A * | 1/2000 | Berman | 623/21.11 |
| 6,371,958 B1 | 4/2002 | Overaker | |
| 6,764,512 B2 | 7/2004 | Keller | |
| 6,966,930 B2 | 11/2005 | Arnin et al. | |
| 2002/0026244 A1 | 2/2002 | Trieu | |
| 2002/0161114 A1 | 10/2002 | Gunatillake et al. | |
| 2003/0125748 A1 | 7/2003 | Li et al. | |
| 2004/0044410 A1 | 3/2004 | Ferree et al. | |
| 2004/0097943 A1 * | 5/2004 | Hart | 606/72 |
| 2004/0193279 A1 * | 9/2004 | Roger | 623/20.28 |
| 2004/0220296 A1 | 11/2004 | Lowman et al. | |
| 2004/0228901 A1 | 11/2004 | Trieu et al. | |
| 2004/0267277 A1 | 12/2004 | Zannis et al. | |
| 2005/0131541 A1 * | 6/2005 | Trieu | 623/17.11 |
| 2005/0154463 A1 | 7/2005 | Trieu | |
| 2005/0177240 A1 | 8/2005 | Blain | |
| 2005/0197711 A1 | 9/2005 | Cachia | |
| 2005/0240269 A1 | 10/2005 | Lambrecht et al. | |
| 2005/0283159 A1 | 12/2005 | Amara | |
| 2006/0084983 A1 | 4/2006 | Kim | |

(Continued)

FOREIGN PATENT DOCUMENTS
WO    WO-2005/070309 A1    8/2005
(Continued)

OTHER PUBLICATIONS

Final Rejection mailed on Mar. 1, 2010, for U.S. Appl. No. 11/862,095, filed Sep. 26, 2007, 14 pages.

(Continued)

*Primary Examiner* — Bruce E Snow
*Assistant Examiner* — Melissa Hoban
(74) *Attorney, Agent, or Firm* — Morrison & Foerster LLP

(57) ABSTRACT

Devices and treatments for various joint conditions include a resilient elongate orthopedic device inserted into a joint space using a suture. The suture is passed through the joint space and used to pull the orthopedic device into the joint space. The suture may be using a percutaneously inserted needle or other type of needle-based delivery instrument. The resilient elongate orthopedic device may be restrained to a reduced profile that permits minimally invasive implantation, but assume an enlarged profile when positioned at an implantation site.

14 Claims, 30 Drawing Sheets

U.S. PATENT DOCUMENTS

| | | | |
|---|---|---|---|
| 2006/0085068 A1 | 4/2006 | Barry | |
| 2006/0149259 A1* | 7/2006 | May et al. | 606/72 |
| 2006/0149261 A1 | 7/2006 | Nilsson et al. | |
| 2006/0212110 A1 | 9/2006 | Osborne et al. | |
| 2006/0265077 A1 | 11/2006 | Zwirkoski | |
| 2006/0283159 A1 | 12/2006 | Scherrer | |
| 2007/0016196 A1 | 1/2007 | Winslow et al. | |
| 2007/0118218 A1* | 5/2007 | Hooper | 623/14.12 |
| 2007/0293947 A1 | 12/2007 | Mansmann | |
| 2008/0027560 A1 | 1/2008 | Jackson et al. | |
| 2008/0097606 A1* | 4/2008 | Cragg et al. | 623/14.12 |
| 2008/0255501 A1 | 10/2008 | Hogendijk et al. | |
| 2008/0255664 A1 | 10/2008 | Hogendijk et al. | |
| 2009/0005871 A1 | 1/2009 | White et al. | |
| 2009/0012612 A1 | 1/2009 | White et al. | |

FOREIGN PATENT DOCUMENTS

| | | | |
|---|---|---|---|
| WO | WO-2008/124737 | A2 | 10/2008 |
| WO | WO-2008/124737 | A3 | 10/2008 |
| WO | WO-2008/124739 | A1 | 10/2008 |
| WO | WO-2010/030933 | A1 | 3/2010 |

OTHER PUBLICATIONS

International Preliminary Report on Patentability mailed on Oct. 22, 2009, for PCT Patent Application No. PCT/US2008/059682, filed on Apr. 8, 2008, 6 pages.

International Preliminary Report on Patentability mailed on Oct. 29, 2009, for PCT Patent Application No. PCT/US2008/059679, filed on Apr. 8, 2008, 7 pages.

International Search Report mailed on Sep. 3, 2008, for PCT Application No. PCT/US08/59682, filed on Apr. 8, 2008, 1 page.

International Search Report mailed on Jun. 8, 2009, for PCT Application No. PCT/US08/59679, filed on Apr. 8, 2008, 1 page.

International Search Report mailed on Jan. 11, 2010 for PCT Patent Application No. PCT/US2009/056724, filed on Sep. 11, 2009, 1 page.

Non-Final Office Action mailed on Jul. 6, 2009, for U.S. Appl. No. 11/862,095, filed Sep. 26, 2007, 9 pages.

Written Opinion of the International Searching Authority mailed on Sep. 3, 2008, for PCT Application No. PCT/US08/59682, filed on Apr. 8, 2008, 4 pages.

Written Opinion of the International Searching Authority mailed on Jun. 8, 2009, for PCT Application No. PCT/US08/59679, filed on Apr. 8, 2008, 3 pages.

Written Opinion of the International Searching Authority mailed on Jan. 11, 2010 for PCT Patent Application No. PCT/US2009/056724, filed on Sep. 11, 2009, 12 pages.

Final Rejection mailed on Jan. 4, 2011, for U.S. Appl. No. 12/099,296, filed Apr. 8, 2008, 10 pages.

Non-Final Office Action mailed on Jun. 1, 2010, for U.S. Appl. No. 12/099,296, filed Apr. 8, 2008, 6 pages.

Non-Final Office Action mailed on Oct. 18, 2010, for U.S. Appl. No. 12/212,587, filed Sep. 17, 2008, 13 pages.

Non-Final Office Action mailed on Oct. 27, 2010, for U.S. Appl. No. 12/694,178, filed Jan. 26, 2010, 12 pages.

Non-Final Office Action mailed on Nov. 9, 2010, for U.S. Appl. No. 12/210,101, filed Sep. 12, 2008, 11 pages.

* cited by examiner

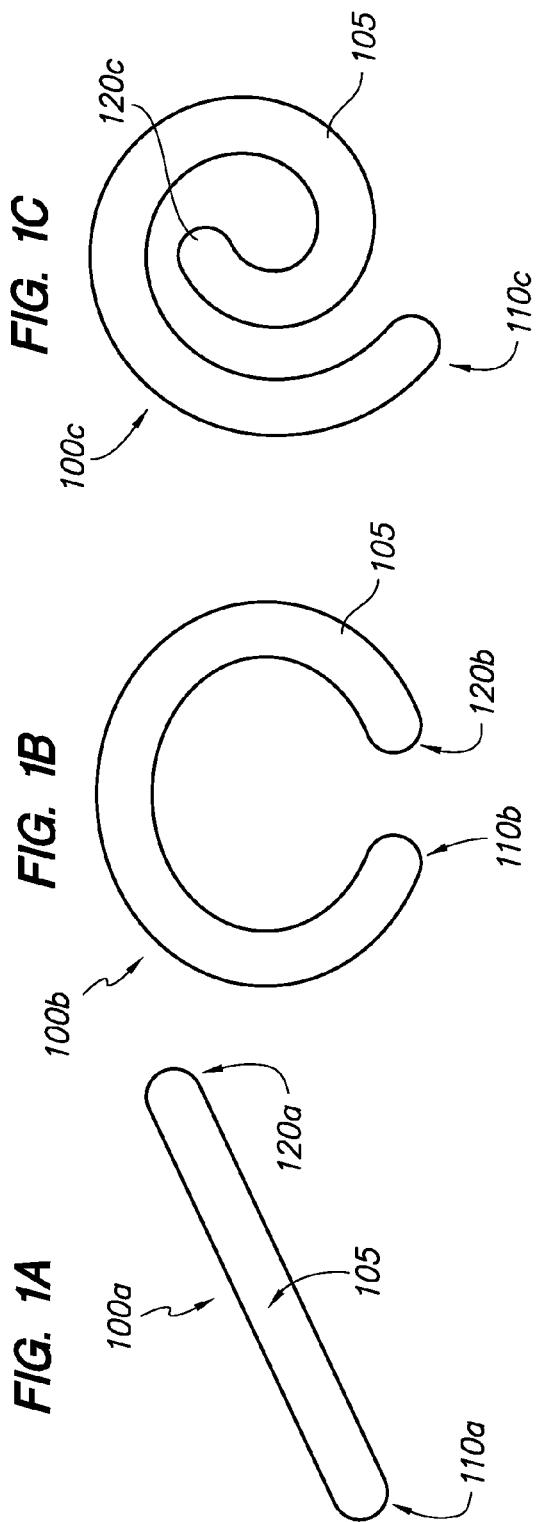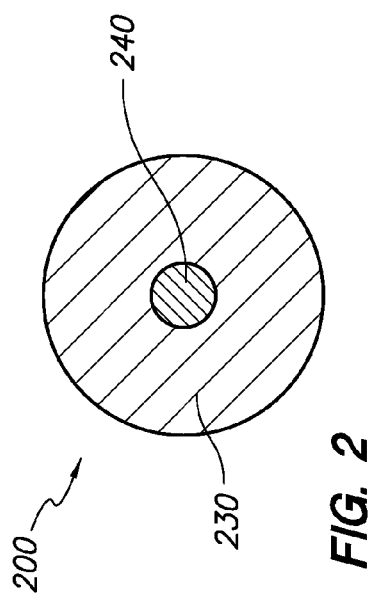

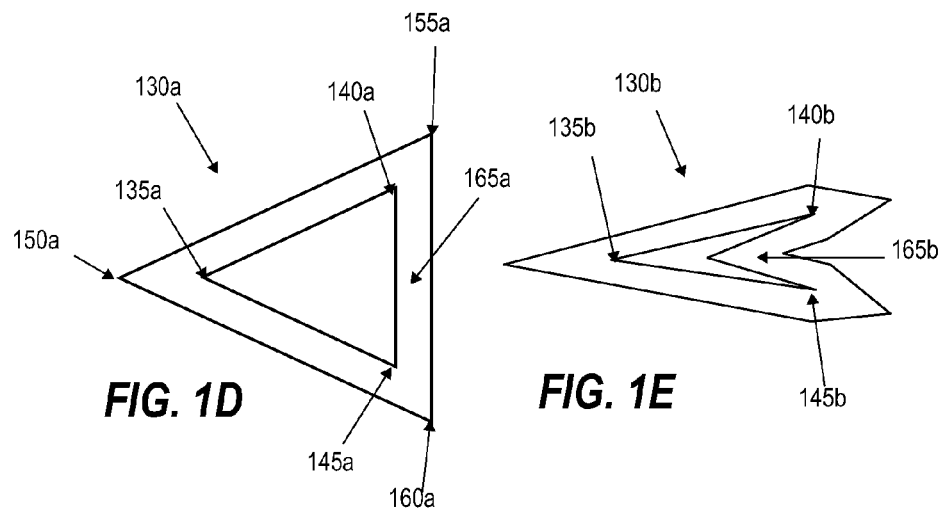
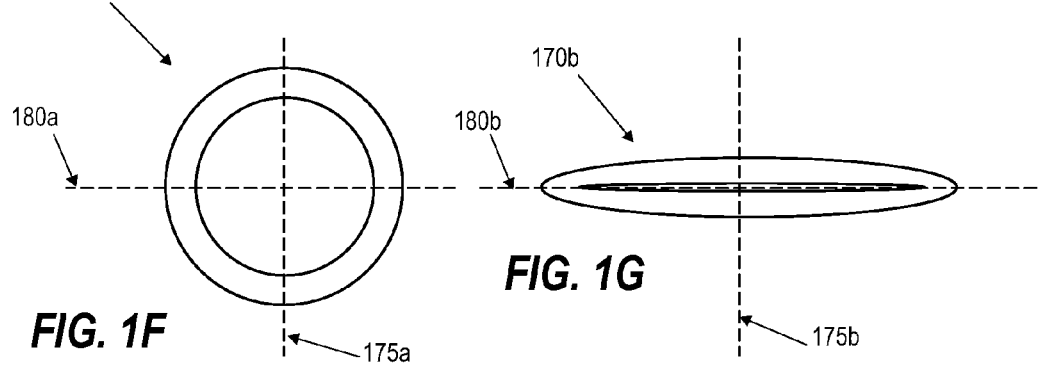
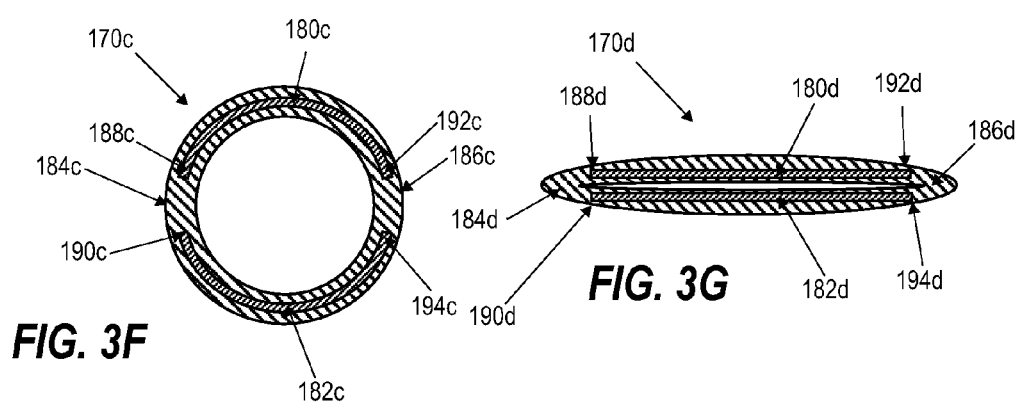

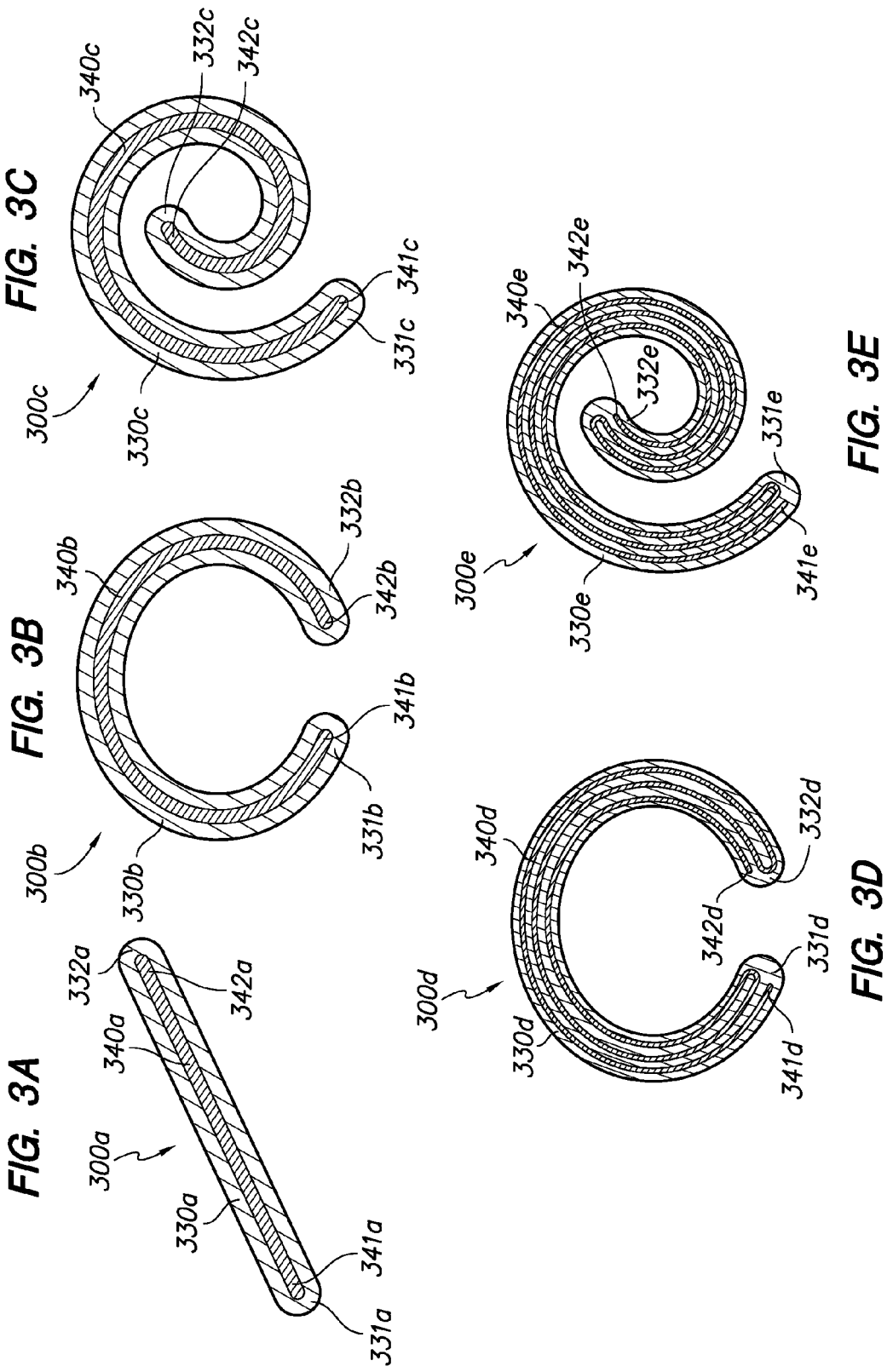

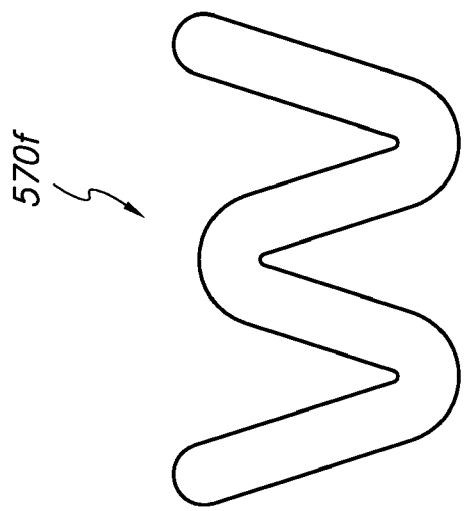
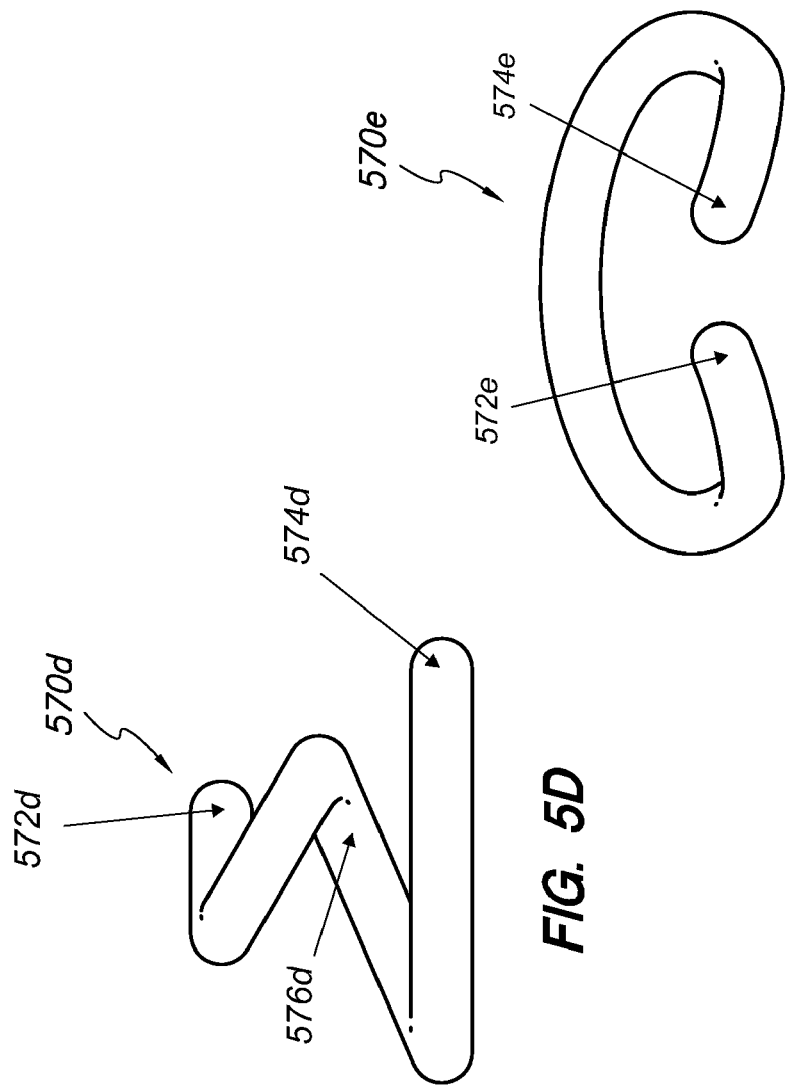

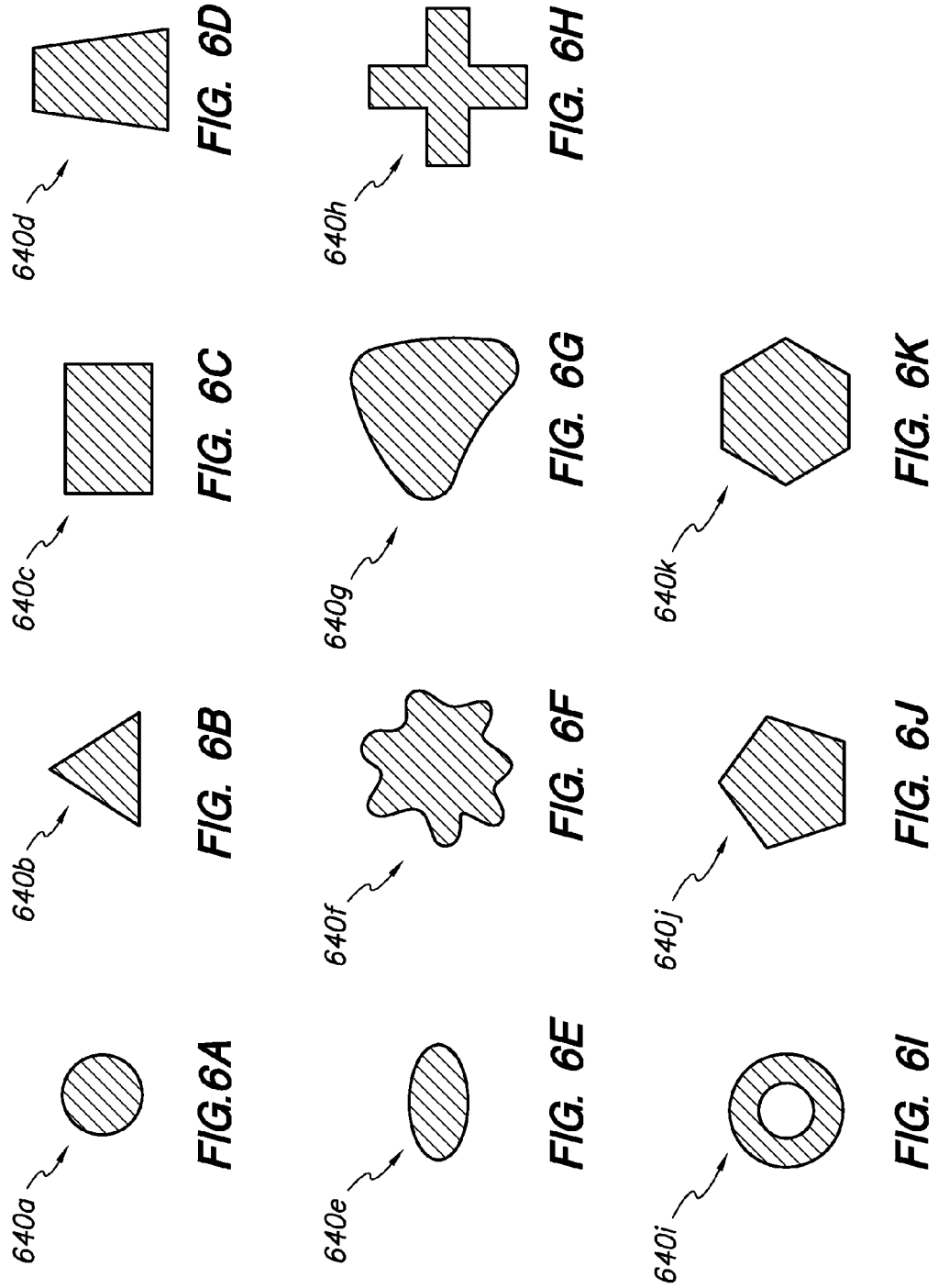

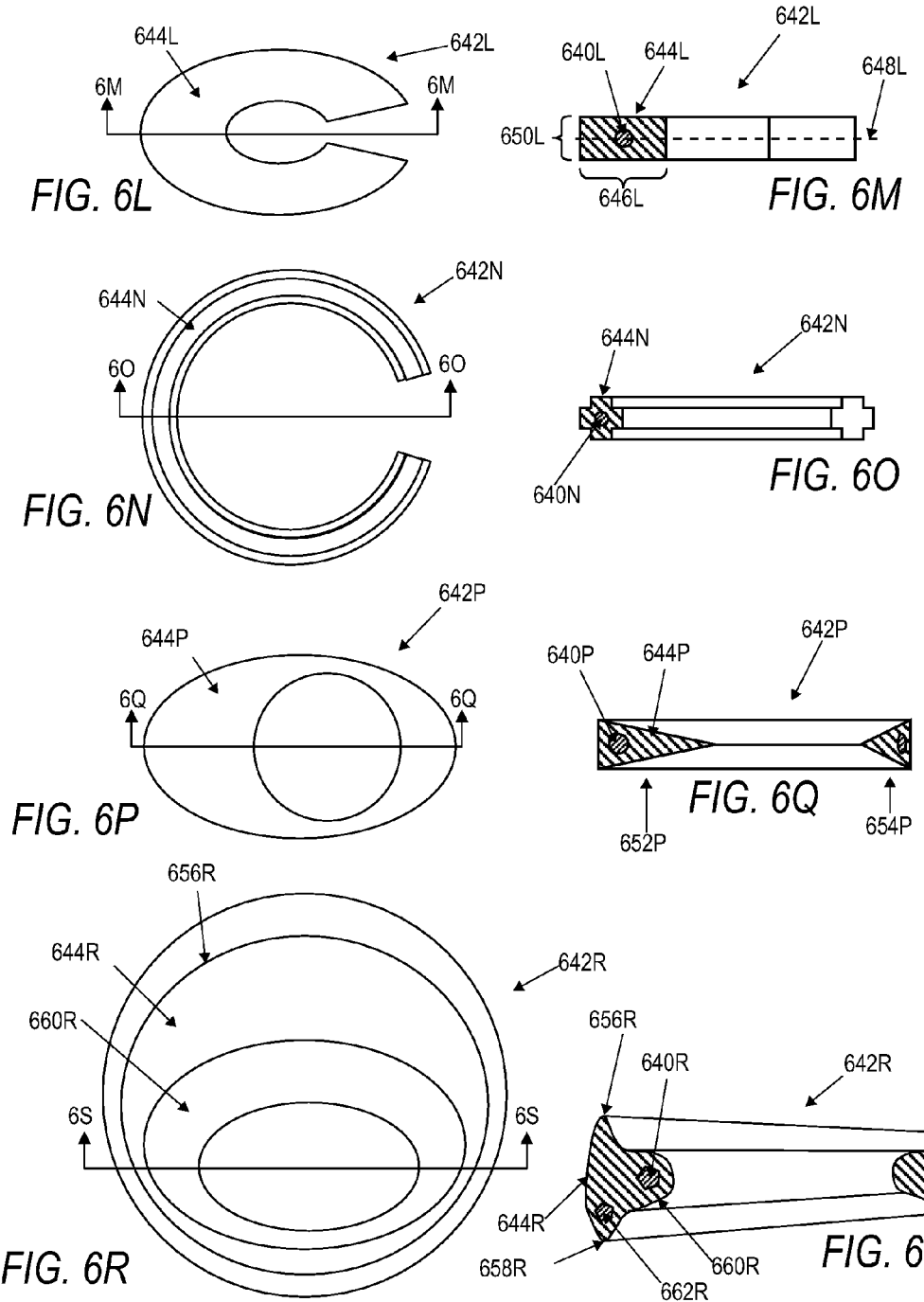

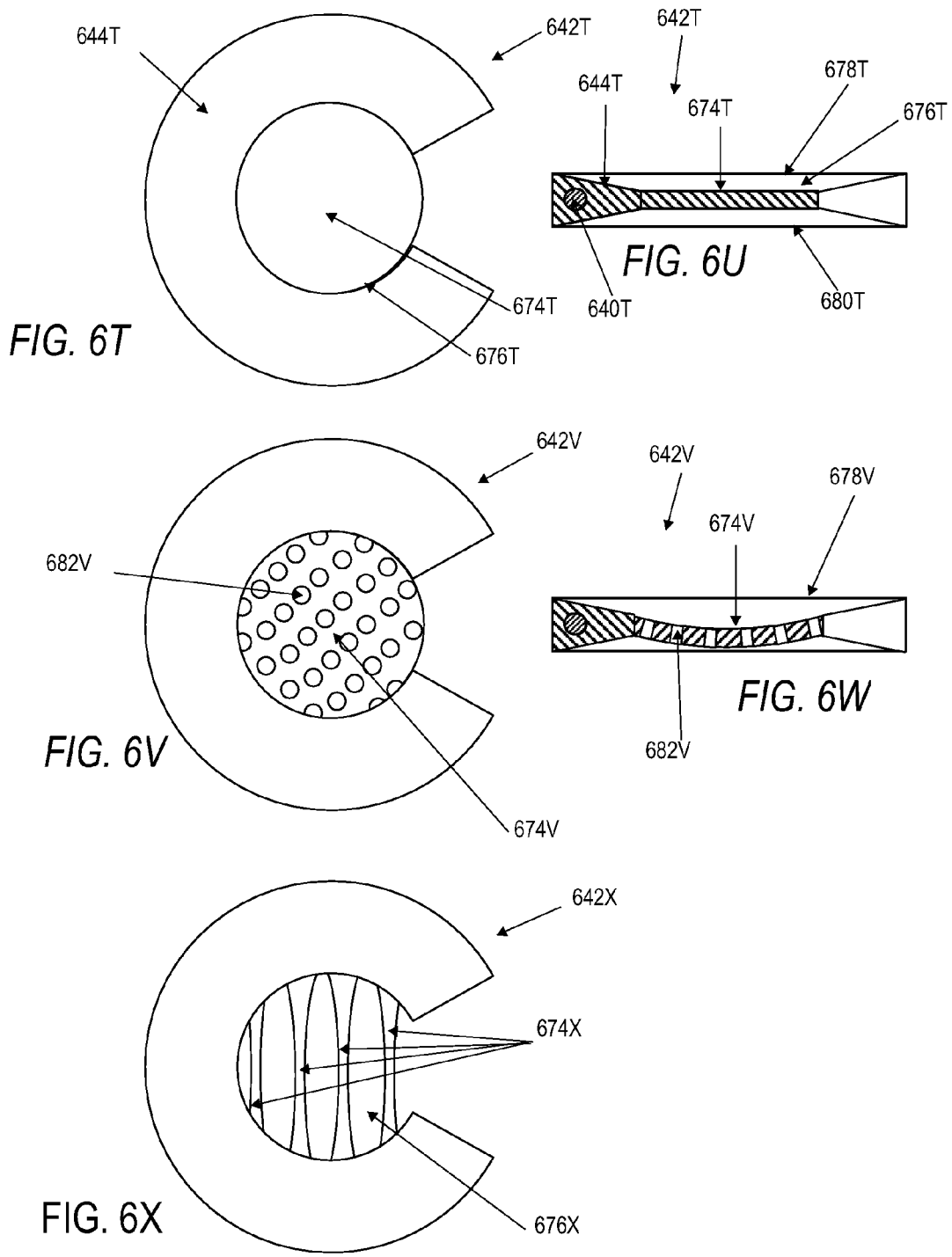

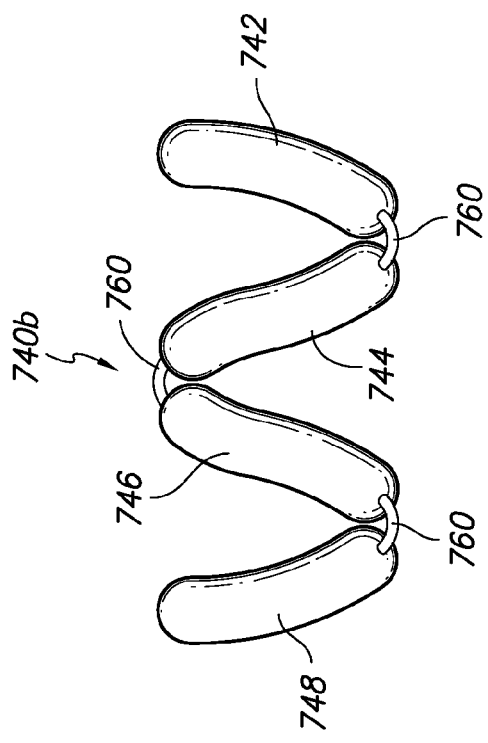
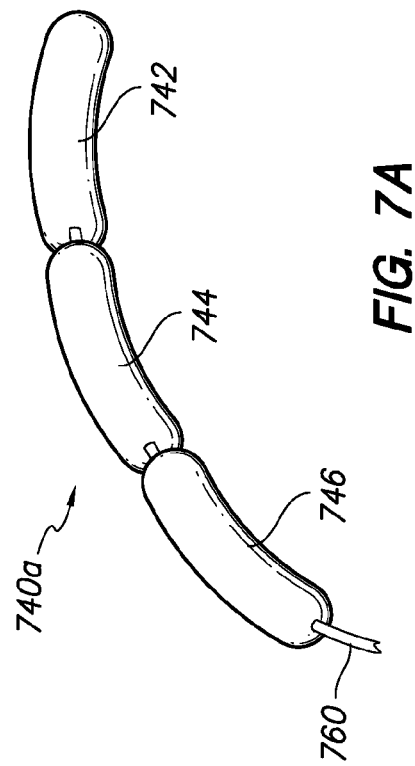
FIG. 7A
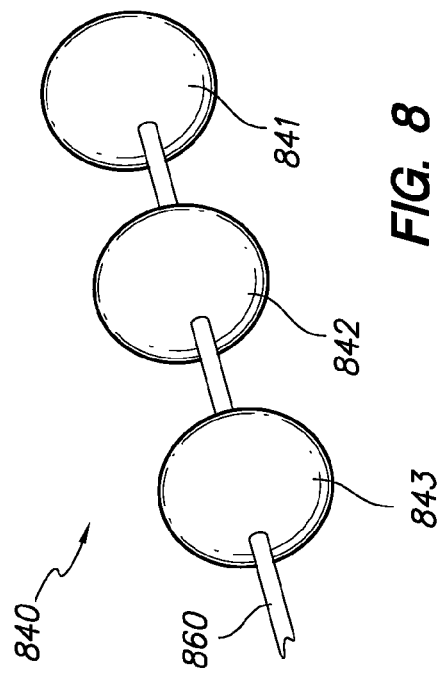
FIG. 7B
FIG. 8

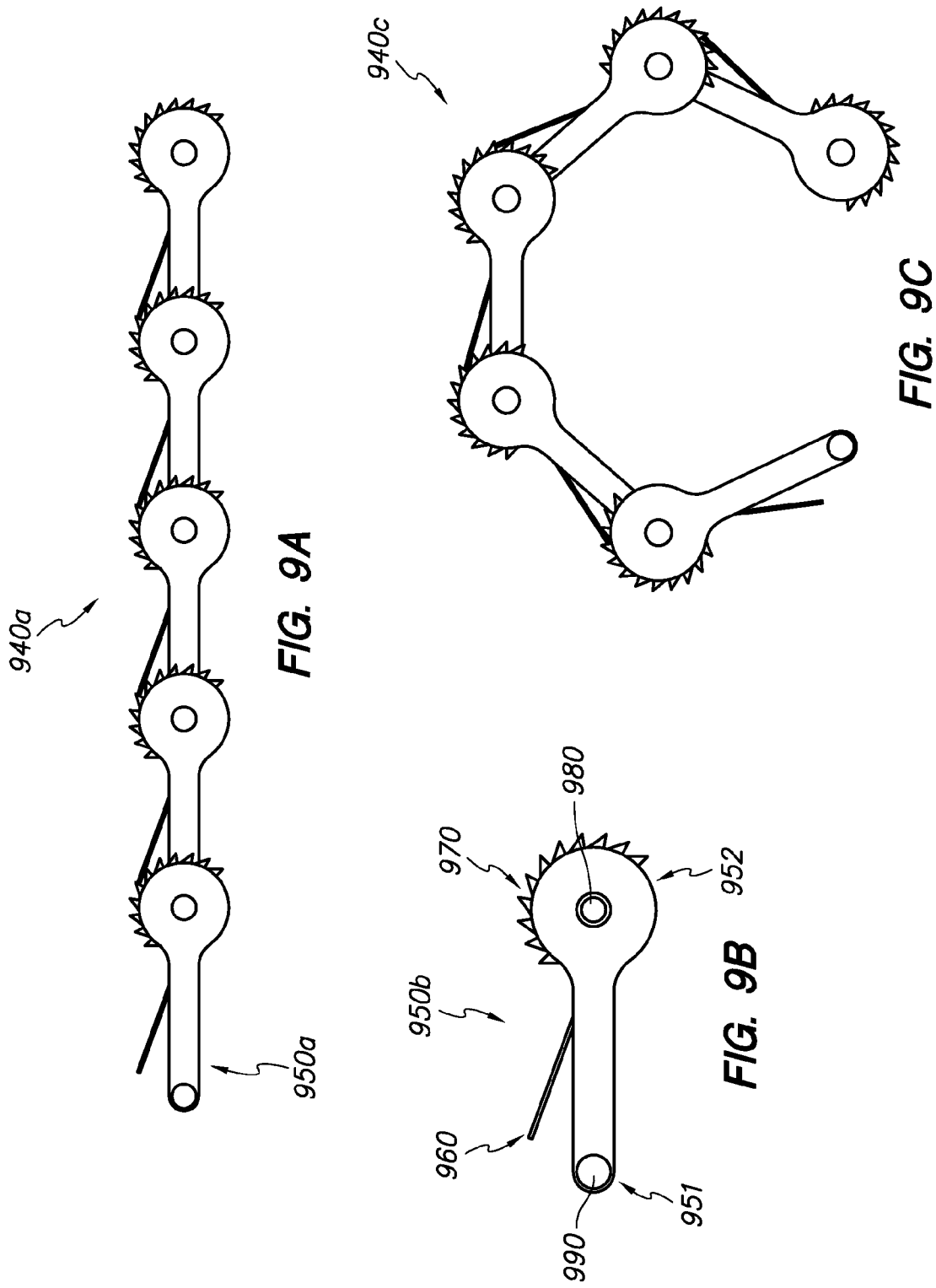

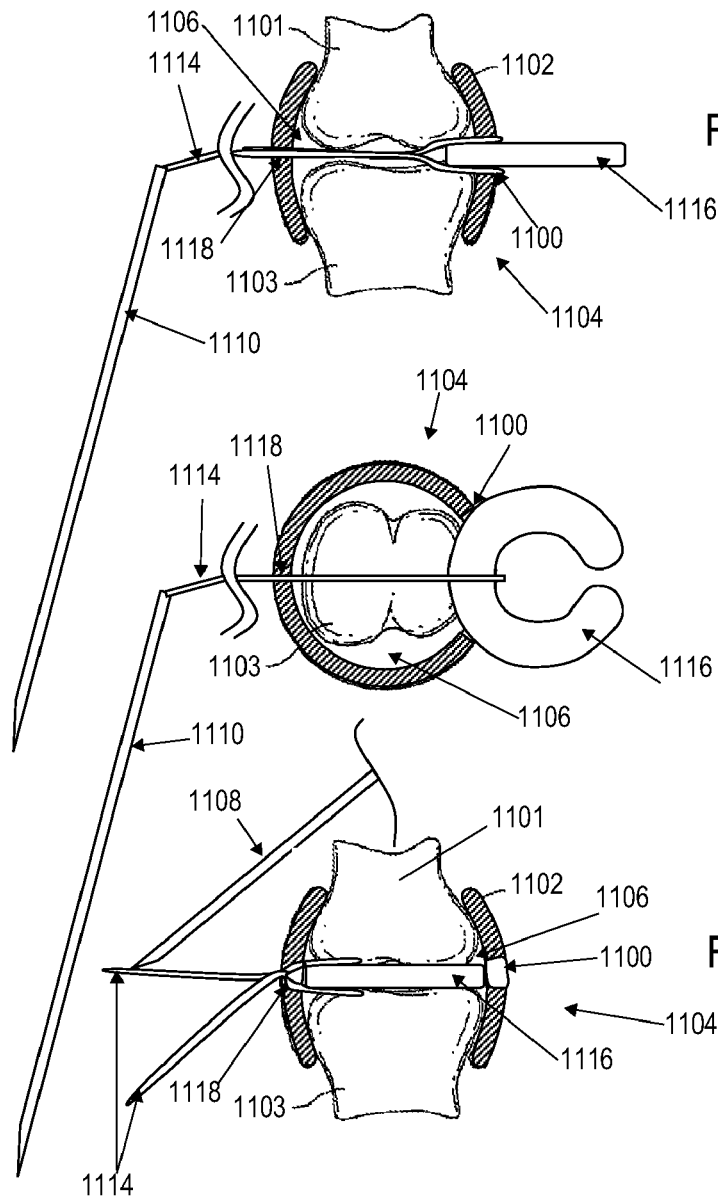

SUTURE-BASED ORTHOPEDIC JOINT DEVICE DELIVERY METHODS

CROSS-REFERENCE TO RELATED APPLICATIONS

This application is related to U.S. application Ser. No. 11/862,095, filed Sep. 26, 2007, U.S. application Ser. No. 12/099,296, filed Apr. 8, 2008, U.S. Provisional Ser. No. 60/911,056, filed Apr. 10, 2007, and to U.S. Provisional Ser. No. 60/975,444, filed Sep. 26, 2007, all of the above which are hereby incorporated by reference in their entirety.

BACKGROUND OF THE INVENTION

Today, there are an increasing number of patients with osteoarthritis, rheumatoid arthritis, and other joint degenerative processes. Osteoarthritis is by far the most common type of arthritis, and the percentage of people who have it grows higher with age. An estimated 12.1 percent of the U.S. population (nearly 21 million Americans) age 25 and older have osteoarthritis of one form or another. Although more common in older people, it usually is the result of a joint injury, a joint malformation, or a genetic defect in joint cartilage. The incidence and prevalence of osteoarthritis differs among various demographic groups: osteoarthritis tends to start for men before the age of 45, and after the age of 45 it is more common in women. It is also more likely to occur in people who are obese or overweight and is related to those jobs that stress particular joints.

Arthritis is a degenerative process that affects the musculoskeletal system and specifically the joints—where two or more bones meet. It often occurs in the joints of the hands and wrists (particularly in the fingers and thumbs, between the phalanges, the metacarpals and/or the carpals), feet (in the toes, between phalanges, metatarsals and/or tarsals), ankles, elbows, shoulders, knees, hips, and the spine (particularly at the neck and lower back). Joint problems can include inflammation and damage to joint cartilage (the tough, smooth tissue that covers the ends of the bones, enabling them to glide against one another) and surrounding structures. Such damage can lead to joint stiffness, weakness, instability and visible deformities that, depending on the location of joint involvement, can interfere with the basic daily activities such as walking, climbing stairs, using a computer keyboard, cutting food and brushing teeth. This ultimately results in moderate to severe pain. Drug regimes can provide temporary relief from the pain, but do not slow down the crippling affects. Drugs may also subject patients to serious side effects and risks, such as the increased cardiovascular risks associated with osteoarthritis drugs Vioxx and Bextra, which were withdrawn from the market. Drugs used to treat other forms of arthritis, such as corticosteroids, are associated with osteoporosis and hyperglycemia and can lead to increased risks of bone fracture and diabetes, for example. When pharmacologic therapy and physical therapy no longer provide adequate relief, only surgical options remain.

The extreme result or end point in traditional treatments is an open surgical procedure to implant a spacer or to perform total joint replacement with a prosthetic device. Current joint replacement therapies (spacers or a total prosthesis) require the joint capsule to be surgically opened and the bone surfaces to be partially or totally removed. Both modalities present various drawbacks. For example, U.S. Pat. No. 6,007,580 to Lehto et al. describes an implantable spacer that must be fixed at one or both ends to the bone of either end of the knuckle (e.g. the metacarpal-phalangeal (MCP) joint). The spacer must be implanted by opening of the joint capsule and be affixed at one or both ends to the corresponding bone surfaces.

Various spacers in the art can cause inflammation, while total joint replacement can limit the range of motion and also compromise the strength and stability of the joint. These surgeries are highly invasive and require the joint capsule to be surgically opened, and the incision itself can result in inflammation and infection. Due to the invasiveness of the procedure, prolonged healing times are required. Furthermore, the invasive nature of these surgeries sometimes precludes a second joint replacement or spacer when the first joint device wears out or fails.

It would be desirable as well as beneficial if there were an intermediary step or alternative treatment before subjecting patients to drastic joint replacement and/or long-term drug therapy.

BRIEF SUMMARY OF THE INVENTION

Various embodiments disclosed herein relate generally to the treatment of osteoarthritis, rheumatoid arthritis, and other degenerative joint processes, and include but are not limited to minimally invasive implantable devices to reduce bone-to-bone contact in a joint.

Systems and methods for treating degenerative joint conditions include an orthopedic device comprising a resilient elongate member, which may be implanted in a joint space using a suture or other type of bendable elongate element. Using minimally invasive surgical techniques, a small skin incision and arthrotomy are made to provide access to the joint. The suture is passed through the incision and joint space and used to pull the orthopedic device into the joint space. The suture may also be inserted using a percutaneously inserted needle or other type of needle-based delivery instrument. The orthopedic device may be restrained to a reduced profile that permits minimally invasive implantation, but changes to an enlarged profile when positioned at an implantation site. The orthopedic device may comprise a shape-memory and/or superelastic material, and may comprise an open or closed shape configuration.

In one example, an orthopedic joint device is provided, comprising a resilient C-shape joint device with a shape-memory elongate curved core and an outer polymeric articular jacket, where the joint device has a first configuration where the C-shape joint device is coupled to a suture and in a deformed reduced profile, a second configuration where the joint device is coupled to the suture and in an expanded profile, and a third expanded configuration where the joint device is in the expanded profile without coupling to the suture.

In another example, an orthopedic device system comprises an orthopedic device with a resilient elongate core, a flexible polymeric jacket covering at least a portion of the resilient elongate core, and a first suture aperture, wherein the orthopedic device is configured to reside between two opposing articular surfaces and within a joint space of a joint. In some further examples, the elongate core may have a delivery configuration and an implantation configuration, and the implantation configuration is optionally a non-linear configuration, including but not limited to a "C"-shape configuration. In other examples, the delivery configuration may be a linear configuration. The first suture aperture may comprise a suture lumen through the jacket, or a suture eyelet coupled to the jacket, while in some examples, the core may comprise a suture eyelet. In one specific example, the suture eyelet may comprise a twisted loop of the core. Some systems may further comprise a suture, which may be located in the first suture aperture. In some examples, the system may also further comprise a penetrating member, which is optionally pre-attached to the suture. The penetrating member, the suture and the orthopedic device may be provided in a single sterile package. The system may also further comprise a penetrating member holder, which in turn may optionally comprise an orthopedic device retaining assembly, such as a retaining post. In some examples, the elongate core may have an elongate length that is at least about 50% of the circumference of the joint space. The joint space may be a joint space of a carpo-metacarpal joint, such as the carpo-metacarpal joint of a thumb. In some systems, the orthopedic device may further comprise an inner region at least partially surrounded by the resilient elongate core, and at least one span member across the inner region. Sometimes, the span member may have a planar configuration, and may comprise a resilient or elastic material, for example. The jacket of the orthopedic device may comprise a thickened jacket region about the first suture aperture. The system may also optionally comprise a first pull member and a second pull member, wherein the first pull member is coupled to the first suture aperture. The second pull member may be coupled to a second suture aperture, and in some further examples, the first and second pull members may each pass through a third suture aperture. An optional third pull member may also be coupled to the third suture aperture.

In another example, a method of implanting a orthopedic device in a patient is provided, comprising percutaneously inserting a needle through a first joint capsule opening of a joint space, passing the needle with an attached suture across the joint space and through a second joint capsule opening, wherein the second joint capsule opening is smaller than the first joint capsule opening, pulling a resilient orthopedic device into the joint space using the suture, wherein the resilient orthopedic device comprises a first end, a second end, and a body therebetween having an elongate arcuate configuration, separating at least a portion of the suture from the resilient orthopedic device, and removing at least a portion of the suture from the patient. The method may optionally further comprise abutting the resilient orthopedic device against the second joint capsule opening, positioning the resilient orthopedic device symmetrically within the joint space with respect to the second joint capsule opening, and/or restraining the resilient orthopedic device in a reduced profile as the resilient orthopedic device traverses the first joint capsule opening. In some further examples, the method may further comprise enlarging the resilient orthopedic device from a reduced profile to an enlarged profile with substantially the same volume as the orthopedic device in the reduced profile, and/or with substantially the same mass as the orthopedic device in the reduced profile. The method may also further comprise restraining the resilient orthopedic device in a delivery configuration as the resilient orthopedic device traverses the first joint capsule opening. The method may also further comprise releasing the resilient orthopedic device from the delivery configuration in the joint space to assume an implantation configuration that is non-linear. In some methods, a distance between a first end and a second end of the resilient orthopedic device in the delivery configuration is greater than the distance between the first end and the second end of the resilient orthopedic device in the implantation configuration. The implantation configuration may comprise at least one arcuate section, and/or a generally a non-planar implantation configuration. In some examples, a first portion of the resilient orthopedic device may have a delivery position in the delivery configuration that is different from an implantation position in the implantation position with respect to a second portion of the resilient joint implant. The method may also further comprise orienting the resilient orthopedic device in the joint space such that the delivery position and the implantation position of the first portion of the resilient orthopedic device generally lie in a plane that is generally aligned with an axis between the first and second joint capsule openings. In some examples, the resilient orthopedic device may be pre-coupled to the suture at the point-of-manufacture. Also, when pulling the resilient orthopedic device, the pulling may be performed such that the body of the resilient orthopedic device enters the joint space before the first and second ends. The joint space may be a trapeziometacarpal or a carpo-metacarpal joint, for example, and the first joint capsule opening may be located on the dorsal surface of the joint space.

In another embodiment, the method of implanting a orthopedic device is provided, comprising pulling a joint implant into a joint space from a first joint capsule opening using a pulling force acting through a second joint capsule opening. The joint space may be located in an extremity of a patient, including the upper extremities and the lower extremities, and the joint space may be a carpal-metacarpal joint space, for example. The second joint capsule opening may be formed using a penetrating member, which may be formed from the joint space or external to the joint space. Examples of the penetrating member may include a needle attached to a suture, and the method may further comprise passing the suture through the first joint capsule opening and through the second joint capsule opening. The method may also further comprise coupling the suture and the joint implant together, such as passing the suture through the joint implant, or passing the suture through a pre-formed lumen of the joint implant, or looping the suture around the joint implant. The joint implant may be a bendable joint implant having a reduced profile and an enlarged profile, wherein the enlarged profile has substantially the same volume and/or mass as the reduced profile. In some examples, the joint implant may comprise at least one articulated joint, such as a plurality of pivot joints. In other examples, the joint implant may be a resilient joint implant. While passing through the first joint capsule opening, the resilient joint implant may be in a restrained configuration, and in some instances, the resilient joint implant may be placed in the restrained configuration at the point-of-manufacture or at the point-of-use. A delivery cannula may be used to restrain the resilient joint implant. The method may also optionally comprise positioning the delivery cannula in the joint space through the first joint capsule opening. In some instances, the pulling force acts through a flexible line coupled to the joint implant, and sometimes, any tension in the flexible line may be relieved after the joint implant is located in the joint space. The method may also comprise separating at least a portion of the flexible line from the joint implant and pulling at least a portion of the flexible line out of the joint space.

BRIEF DESCRIPTION OF THE DRAWINGS

These and other features will now be described in connection with various embodiments herein, in reference to the accompanying drawings. The illustrated embodiments, however, are merely examples and are not intended to limit the claimed subject matter.

FIG. 1A is a schematic top view of one embodiment of an orthopedic device comprising a substantially straightened configuration.

FIG. 1B is a schematic top view of one embodiment of an orthopedic device comprising an open hoop arcuate configuration.

FIG. 1C is a schematic top view of one embodiment of an orthopedic device comprising a nautilus-style spiral arcuate configuration.

FIG. 1D is a schematic top view of one embodiment of an orthopedic device comprising a closed polygonal configuration.

FIG. 1E is a schematic top view of the orthopedic device of FIG. 1D in a collapsed delivery configuration.

FIG. 1F is a schematic top view of one embodiment of an orthopedic device comprising a closed circular configuration.

FIG. 1G is a schematic top view of the orthopedic device of FIG. 1F in a collapsed delivery configuration.

FIG. 2 is a schematic cross-sectional view perpendicular to a longitudinal axis of an embodiment of an orthopedic device comprising an elongate core and an articular layer surrounding at least a portion of the core.

FIG. 3A is a schematic longitudinal cross-sectional view of an embodiment of an orthopedic device having a substantially straightened configuration and comprising an elongate core and an articular layer surrounding at least a portion of the core.

FIG. 3B is a schematic longitudinal cross-sectional view of an embodiment of an orthopedic device having an open hoop arcuate configuration, the device comprising an elongate core and an articular layer surrounding at least a portion of the core.

FIG. 3C is a schematic cross-sectional view of an embodiment of an orthopedic device having a nautilus-style spiral arcuate configuration, the device comprising an elongate core and an articular layer surrounding at least a portion of the core.

FIG. 3D is a schematic longitudinal cross-sectional view of an embodiment of an orthopedic device having an open hoop arcuate configuration, the device comprising one or more elongate cores wrapped, braided or folded along a length of the device and an articular layer surrounding at least a portion of the core.

FIG. 3E is a schematic longitudinal cross-sectional view of an embodiment of an orthopedic device having a nautilus-style spiral arcuate configuration, the device comprising one or more elongate cores wrapped, braided or folded along a length of the device and an articular layer surrounding at least a portion of the core.

FIG. 3F is a schematic planar cross-sectional view of the orthopedic device of FIG. 1F.

FIG. 3G is a schematic planar cross-sectional view of the orthopedic device of FIG. 1G.

FIG. 5D is a schematic side view of an embodiment of an orthopedic device comprising a multi-planar spiral configuration.

FIG. 5E is a schematic side view of an embodiment of an orthopedic device comprising a multi-planar arcuate configuration.

FIG. 5F is a schematic side view of an embodiment of an orthopedic device comprising a "W"-shape configuration.

FIGS. 6A to 6K are schematic cross-sectional views of various embodiments of elongate cores.

FIGS. 6L to 6S are schematic superior and cross-sectional views of various embodiments of orthopedic devices with non-circular cross-sectional shapes.

FIGS. 6T to 6W are schematic superior and cross-sectional views of various embodiments of an orthopedic device with a membrane member.

FIG. 6X is a schematic superior view of additional embodiment of orthopedic device with membrane member.

FIG. 7A is a schematic perspective view of an embodiment of an orthopedic device comprising a plurality of independent or inter-connectable discrete elongate members.

FIG. 7B is a schematic perspective view of an embodiment of an orthopedic device comprising a plurality of independent or inter-connectable discrete elongate members in a "W"-shape configuration.

FIG. 8 is a schematic perspective view of an embodiment of an orthopedic device comprising a plurality of independent or inter-connectable discrete members.

FIG. 9A is a schematic side view of an embodiment of an elongate core comprising a plurality of inter-connectable discrete members in a substantially straightened configuration.

FIG. 9B is a schematic side view of an inter-connectable discrete member of FIG. 9A.

FIG. 9C is a schematic side view of an embodiment of an elongate core comprising a plurality of inter-connectable discrete members according to FIG. 9A in an arcuate open loop configuration.

FIGS. 10A to 10L are schematic cross-sectional views of one embodiment for implanting an orthopedic device in a joint space using a suture. FIGS. 10A, 10C, 10E, 10G, 10I and 10K are longitudinal cross-sectional views through the joint, whereas FIGS. 10B, 10D, 10F, and 10H, 10J and 10L are the corresponding axial cross-sectional views, respectively.

FIGS. 30A, 31A and 32A are schematic side cutaway views depicting the use of the system in FIG. 28A in a joint, whereas

Figure 4A:
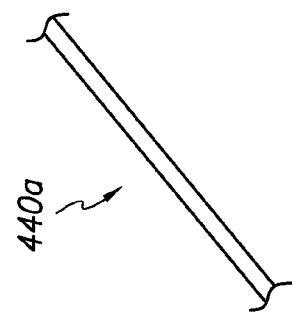
FIG. 4A is a schematic side view of an embodiment of an elongate core comprising one or more substantially linear or straight members.

Throughout the figures, the same reference numerals and characters, unless otherwise stated, are used to denote like features, elements, components or portions of the illustrated embodiments. In certain instances, similar reference number schemes are used whereby the reference numerals referred to as "AA" in reference numeral "AAxx" correspond to a figure while the "xx" is directed to similar or interchangeable features, elements, components or portions of the illustrated embodiments in different figures. In certain instances, similar names may be used to describe similar components with different reference numerals which have certain common or similar features. Moreover, while the subject invention will now be described in detail with reference to the figures, it is done so in connection with the illustrative embodiments. It is intended that changes and modifications can be made to the described embodiments without departing from the true scope and spirit of the subject invention as defined by the claims.

DETAILED DESCRIPTION OF THE INVENTION

As should be understood in view of the following detailed description, this application is generally directed to systems and methods for minimally-invasive treatment of bone joints, in both medical and veterinary settings (including both small and large animal veterinary medicine). Bone joints contemplated for various embodiments of the orthopedic systems and methods include, but are not limited to, hands (fingers and thumbs, between phalanges, metacarpals and/or carpals), feet (in the toes, between phalanges, metatarsals and/or tarsals), wrists, elbows, shoulders, knees, hips, and the spine (particularly at the neck and lower back). In some embodiments, an orthopedic device comprises a shape memory body that is inserted into the joint space, which may restore proper joint alignment and joint mobility affected by degenerative processes. In some embodiments, the orthopedic device has a generally arcuate or rectilinear configuration, which may enhance self-centering positioning of the orthopedic device when deployed.

Referring to FIG. 1A, in one embodiment, the orthopedic device 100a comprises a resilient or flexible elongate body 105 with a proximal end 110a and a distal end 120a, and adapted to undergo configurational change. For example, the elongate body 105 of orthopedic device 100a may have a straight configuration as depicted in FIG. 1A, but may also have, for example, an arcuate "C"-shape configuration as shown in FIG. 1B, and/or a spiral-shape configuration in FIG. 1C. The change from one configuration to another may, for example, facilitate implantation of the orthopedic device in a minimally invasive manner, and/or facilitate force redistribution in the joint during movement or positioning.

In one particular embodiment, the distal end 120a of the orthopedic device 100a may be advanced or inserted into the body of a patient first, before the proximal end 110a of the orthopedic device 100a is inserted. In some embodiments, the orthopedic device 100a has a shape or configuration that facilitates its loading into a lumen within a needle, cannula, or other device for delivering the orthopedic device to the implantation site. The straightened configuration of orthopedic device 100a may be used for delivery of the orthopedic device 100a from a substantially straight needle. As the device 100a exits the needle or cannula, the configuration of the device 100a may change to assume the arcuate or spiral configurations of FIGS. 1B and 1C. In another example, the elongate body 105 of the orthopedic device 100a may be bent or biased to a curve to permit delivery from curved or other non-linear needles or cannulae. Thus, the orthopedic device need not have a linear delivery configuration as depicted in FIG. 1A. The orthopedic device 100a may also be configured with a lumen or one or more apertures to facilitate delivery over a delivery structure, such as a rigid or flexible guidewire. Once implanted into the joint, the orthopedic device may be configured to re-expand to its pre-delivery configuration, or may expand to a different configuration. The deployment configuration may be different, depending upon the base configuration of the orthopedic device, and/or whether the orthopedic device has a resilience or bias to one or more particular configurations. The resulting configuration may also result from anatomical restrictions, for example, relating to the dimensions of the joint capsule, or the geometry of the articular surface. The deployment configuration in the joint capsule may vary in use, depending upon the joint position, the body position of the patient (e.g. standing or lying down) and other conditions which may alter the forces acting on the joint and the orthopedic device. In one example, an orthopedic device has an arcuate configuration that is less-curved, or has a larger major diameter, than the device as fully deployed in the joint, or has an enlarged configuration with at least one dimension that is larger than the corresponding joint space dimension when deployed in the joint space.

In one embodiment, the orthopedic device may be configured and implanted to permit its displacement and/or deformation within the joint. In some instances, the movement and/or deformation facilitates the conformation of the orthopedic device to the natural movement of the bones through the range of motion of the joint. For example, the orthopedic device may be implanted into a joint without any attachment to adjacent tissue and constrained only by the joint capsule and/or ligaments within the joint. In some examples, because the device is not fixed in place (e.g. attached to either end of bones in a joint), the device may "float" between the ends of the bones in a joint. In some embodiments, a floating design and implantation procedure may provide a mechanical advantage over that of a fixed-type orthopedic device that is rigidly attached to bone tissue by redistributing forces acting on the joint.

For example, the "open ring," "hoop" or "coil" configuration, or any "open" embodiment, including open polygons of an orthopedic device, may permit a greater range of deformation than closed structures. An open design may facilitate the distribution of the loading, shearing and/or compressive forces seen by the articulation and/or loading of the joint. Thus, in certain open embodiments of orthopedic devices that are flexible, such as orthopedic device 100b, the open configuration may offer reduced or minimal resistance to shape change. Thus, the orthopedic device 100b can spring open or closed as force is applied to the device or to the joint, but still maintain a bearing, cushion, slidable, or articulate surface. However, orthopedic devices with a closed configuration may also be used and may also have deformation properties.

In some embodiments, the gap between the proximal and distal ends of an orthopedic device with an open configuration could be extended to the entire length of the orthopedic device, e.g. when a device is completely straightened. However, various embodiments of an orthopedic device may be configured with functional operating ranges allow varying degrees of flexion and gap widening to support loads and articulation in the joint. In some embodiments, the functional operating range is based upon the amount of stress and strain that the orthopedic device can undergo without significant plastic change (e.g. less than 5%). In some embodiments comprising a shape memory material such as nickel-titanium, the functional operating range may lie within the range of pseudoelastic deformation of the shape memory component, e.g. a Nitinol core that can undergo strain up to about 8%. In one embodiment, the functional flexion in an open orthopedic device allows for a change in the gap between the open ends of the orthopedic device in situ to flex in a range from about 0.5 to about 6 times or more the distance between the gap when the orthopedic device is in its natural state, either pre-implantation or in situ. In one embodiment, the deformation or flex range is roughly from about 2 to about 6 times or greater the natural gap distance, and in another embodiment the flex range is about 3 to about 5 times greater. In one example, the orthopedic device has a flex range with an upper limit of about 4 times. In one embodiment the functional gap can be as wide as a first dimension, diameter, or width of the over all orthopedic device. Thus, orthopedic device 100b may allow for the redistribution of the compressive and/or shearing forces, as well as the resulting wear along the device. In certain embodiments, the orthopedic devices comprise arcuate configurations, such as an open circle or continuous spiral configurations, rather than closed configurations like a complete ring or closed circular shape. The open configurations may result in increased dissipation or redistribution of loading and compression forces though at least one or two deformations in the orthopedic device. First, an open ring may allow for dynamic loading response as force that is applied to the joint is partially dissipated by the force necessary to radially-outwardly deform the open ring or spiral into a larger radius profile. In one embodiment, the operating range of radial deformation of an arcuate orthopedic device is in the range of about 0 to about 50% of the orthopedic device profile diameter within the joint. Second, as discussed above, the compression of the articular layer may result in cross-sectional deformation into a flatter shape, which may also dissipate force or pressure in the joint.

In one embodiment, the orthopedic device 100b is sized to snugly fit into the joint capsule itself. In some specific embodiments, one or more portions of the orthopedic device may be sized and/or configured to conform to the dimensions of the joint capsule. This fit may facilitate the seating or centering of the orthopedic device 100b with respect to the axis of the bones of the joint, such as in a proximal or distal interphalangeal (PIP/DIP) joint of a finger or an MCP joint of a knuckle.

As used herein, "arcuate" may refer to curved or rounded configurations or shapes, but can also include generally arcuate configurations and shapes that have some straight aspect or element with curved or rounded configurations or shapes. As used herein, arcuate and generally arcuate shapes can include open or closed "C", "O", "S", spiral, nautilus, "Q" and other generally arcuate shapes which can be planar or non-planar. Certain embodiments of the orthopedic device may have open or closed rectilinear configurations, which can include polygons such as triangles, squares, rectangles, diamonds, rhombuses, pentagons, hexagons, octagons and other shapes with generally straight edges, and further including shapes and configurations that are generally rectilinear having some curved edge or corners or segments among rectilinear shapes. As used herein, rectilinear and generally rectilinear shapes can include "N", "M", "W", "Z", "T", "Y", "V", "L", "X" and other generally rectilinear shapes. FIG. 5F, for example, depicts an embodiment of a rectilinear orthopedic device 570f, comprising a "W"-shape configuration. Various embodiments of generally arcuate or generally rectilinear shapes can include shapes with both rectilinear and arcuate portions, such as a "P", "R", "B", and "U".

Embodiments of the orthopedic device may have three major dimensions, which can correspond to a first major dimension, a second major dimension and a third major dimension. In one embodiment, the first major dimension, second major dimension and third major dimension correspond to a width, a height and a thickness, respectively. Certain embodiments have a thickness which corresponds to the smallest dimension, which may generally correspond to the spacing between articulating surfaces of tissue such as bone or cartilage in a joint. In one embodiment, the width and height can be the same, such as with a circular or square-shape orthopedic device. In other embodiments, the height and width may be different, as with an oval shape or a rectangle or other shape with non-equal height and width. In some embodiments, the orthopedic implant can be implanted in joints of varying sizes, in which the first major dimension and second major dimension may have a range of about 0.0394 to about 4.0 inches (or about 1.0 to about 101.6 mm) and the third major diameter may have a range of roughly about 0.001 to about 0.50 inches (or about 0.025 to about 15 mm). Orthopedic devices having other dimensions may also be used, including but not limited to orthopedic devices configured for larger joints such as the knee, hip, ankle, and shoulder, for example. Although the orthopedic device may be implanted between the articular surfaces of two bones, the articular surfaces are not limited to the hinge joints and may include sliding joints. In some examples, the orthopedic device may be inserted into various joints and other locations of the spine, including the facet joints, in an intervertebral disc, or in the post-discectomy space between the endplates of two adjacent vertebral bodies.

As mentioned previously, certain embodiments of the orthopedic device may have a narrowed configuration or a reduced profile to fit in a lumen of a delivery tube or delivery device, or through a small opening in a joint capsule. In one embodiment, a narrowed configuration comprises the reduction of the first major dimension, second major dimension or third major dimension, or a combination thereof. In some embodiments with narrowing configurations, one or more dimensions are reduced while one or more other dimensions are increased. In one embodiment, the orthopedic device can be moved into a narrowed configuration by pinching, squeezing or restraining the device so that parts of the orthopedic device overlap, such as a "C"-shape body being collapsed into an alpha shape ($\alpha$), a gamma shape ($\gamma$), a twisted shape, a helix, and/or a multi-planar configuration, as illustrated in the embodiments of FIGS. 5D and 5E, for example. In one embodiment, the orthopedic device may be manipulated into a straightened or a substantially straightened configuration. In one embodiment, the orthopedic device may have a substantially straightened configuration, including a completely straightened, linear configuration, as well as configurations in which at least a part of the orthopedic device is straightened or partially straightened, configurations in which arcuate orthopedic devices can be made less-arcuate and configurations in which rectilinear orthopedic devices can be made less-rectilinear.

Referring back to FIG. 1A, some embodiments of the orthopedic device may have a relatively uniform width or diameter along its elongate length. However, in other contemplated embodiments, the width of the device body can vary along its length. For example, some orthopedic devices may have one or more tapered sections along a portion of its length, or be tapered along the device's entire length. The tapered section may have a linear or a non-linear taper configuration, and embodiments with two or more tapered sections need not taper in the same direction. The width, or other dimensions of the orthopedic device, can vary from large to small or small to large, making the device thicker in some portions than in others. In one embodiment, the device may be radially compressible along part or over the entire length of the device. In one embodiment, the device may be compressed such that its cross-sectional area is reduced, so that the device may exit a delivery system and expand to a larger cross-sectional area. In one embodiment, the device can be axially compressed or axially stretched along part or over the entire length of the device.

In one embodiment, the orthopedic device 100a comprises a shape memory material. For example, the shape memory material can be made from a shape-memory material, such as Nitinol, or a shape memory plastic, polymeric, or synthetic material, such as polycarbonate urethane. One example of this type of a polyurethane or polyurethane-urea polymer shape memory material is described in United States Patent Publication 2002/0161114 A1, which is hereby incorporated by reference in its entirety and which describes a shape memory polyurethane or polyurethane-urea polymer including a reaction product of: (A) (a) silicon-based macrodiol, silicon-based macrodiamine and/or polyether of the formula (I): A-[(CH2)m-O-]n-(CH2)m-A', wherein A and A are end-capping groups; m is an integer of 6 or more; and n is an integer of 1 or greater; (b) a diisocyanate; and (c) a chain extender; or (B) (b) a diisocyanate: and (c) a chain extender, where the polymer has a glass transition temperature which enables the polymer to be formed into a first shape at a temperature higher than the glass transition temperature, and where the polymer is maintained in the first shape when the polymer is cooled to a temperature lower than the glass transition temperature, so that the polymer is capable of resuming its original shape on heating to a temperature higher than the glass transition temperature. Various embodiments may include a shape memory polymer alone, or a blend of two or more of the shape memory polyurethane or polyurethane-urea polymers or at least one shape memory polyurethane or polyurethane-urea polymer defined above in combination with another material. Other embodiments relate to processes for preparing materials having improved mechanical properties, clarity, processability, biostability and/or degradation resistance and devices or articles containing the shape memory polyurethane or polyurethane-urea polymer and/or composition defined above.

In other embodiments, the orthopedic device may comprise any of a variety of rigid, semi-rigid or flexible materials, which may be metallic or non-metallic, polymeric or non-polymeric, bioresorbable or non-bioresorbable, lipophilic, hydrophilic or hydrophobic, for example. These materials may include but are not limited to stainless steel, cobalt-chromium, titanium, pyrolytic carbon, any of a variety of ceramic or hydroxyapatite-based materials, polymers such as PTFE, silicone, nylon, polyethylene, polypropylene, polycarbonate, polyimide, polycarbonate, polyurethane, PEEK, PEKK and PEBAX, any of a variety of bioresorbable materials such as PGA, PLA, PLGA, PDS and the like, as well as chitosan, collagen, wax and alginate-based materials, and animal-derived materials such as small intestine submucosa (SIS).

In one embodiment, the orthopedic device 100a comprises an articular layer 105, blanket or jacket. The articular layer 105 is sized and configured to be placed within a body, such as in a joint, as a layer between bones of the joint to provide a slidable articulation surface and/or a cushion. In some embodiments, the articular layer can range from about 0.001 to about 0.5 inches thick (or about 0.025 to about 13 mm). The orthopedic device may or may not include a core, backbone or other support structure, which may support the articular layer or contribute or impart certain features or characteristics to the orthopedic device. Support structures, such as the core, are described in greater detail below.

In one embodiment, the articular layer 105 is configured to be compressed by forces acting on the joint. For example, in one embodiment an articular layer may be compressed from a substantially circular cross-sectional shape to an oval, elliptical, or football shaped cross-sectional shape. As the compression occurs, the amount of surface coverage of the articular layer with respect to bony joint contact, resulting in reduced in relative pressure across the joint. In one embodiment, the operating range of compression of an orthopedic device is in the range of about 0 to about 50% of the cross-sectional diameter or other dimension along the axis of compressive force.

The articular layer 105 may comprise one or more layers of material, and any of a variety of materials may be used for each layer. In certain embodiments of the orthopedic device 100a, the body of the orthopedic device 100a comprises an articular layer with shape-memory properties, with or without any backbone or other type of support structure. The shape-memory properties may include but are not limited to temperature-induced configuration changes as well as stress-induced pseudoelastic properties. In certain embodiments, the articular layer 105 materials may include but are not limited to silicone, PTFE or ePTFE, ultra high molecular weight polyurethane or and any implantable grade material, or other materials disclosed above. The articular layer 105 can be compliant and/or compressible, or may have a non-compressible construction. In certain embodiments, the articular layer 105 can have any of a variety of durometers (material hardness) from about 30 to about 90 Shore A, for example. In certain embodiments, the articular layer 105 may comprise a porous material, which may have a closed or open-pore structure. The porous coatings, layers or structures may include but are not limited to macroporous or nanoporous coatings or structures. In some instances, a porous coating may facilitate tissue ingrowth and/or augment the inflammatory response to the orthopedic device, if any. In another embodiment, the coating material can form a casing (or covering) that is spongy or harder or less compliant. The pores of the material could be loaded with one or more therapeutic agents. The casing could form a scaffold for tissue ingrowth and could be used in joints with certain wear characteristics, but is not limited to use with these joints. In some embodiments, the articular layer 105 may be coated with a secondary surface layer, such as another polymer of a different material property, or an anti-friction high wear material such as Parylene, or other similar materials which are known to the art as providing for a low friction surface.

In certain embodiments, the articular layer 105 may contain a material or a drug to inhibit or promote inflammation, joint deterioration etc., or a material or drug to encourage tissue regeneration or device encapsulation. For example, certain embodiments of the articular layer 105 may be coated with or contain one or more therapeutic agents, such as a long-acting steroid or a disease-modifying anti-rheumatic drug (DMARD). DMARDs include but are not limited to agents such as gold, D-penicillamine, methotrexate, azathioprine and cyclophosphamide, leflunomide, etanercept, infliximab, minocycline and certain anti-malarial agents used for arthritis treatment, for example. The therapeutic agents need not be limited to joint-specific therapy agents, however. In other embodiments, the therapeutic agent may include an antibiotic (e.g. a macrolide, a cephalosporin, a quinolone, an aminoglycoside, a beta-lactam or beta-lactamase inhibitor, a lincosamide, or glycopeptides antibiotic, etc.), a sclerosing agent (e.g. bleomycin, tetracycline, talc, alcohol, sodium tetradecyl sulfate, etc.), or other type of inflammation-inducing agent, a growth factor (e.g. connective tissue growth factor, cartilage-derived retinoic acid sensitive protein), and other agents. In some embodiments, one or more therapeutic agents may be injected or infused into a joint space, separate from the orthopedic device, using any of a variety of forms (aqueous solution, suspension, oil, foam, a separate drug eluting disc or other structure, etc.). These therapeutic agents may include viscosupplements (e.g. hylan G-F 20 such as Synvisc®, or various formulations of sodium hyaluronate such as Hyalgan®, Suppartz®, Euflexxa® and Orthovisc®).

In other embodiments, the articular layer may comprise a plurality of surface projections and/or pores, which may cause a mechanical irritant response when implanted and may induce the growth of new tissue or cartilage, or an organization of fluids contained in the joint. The projections and/or pores may be grossly visible on the surface of the articular layer, or may be nano- or micro-sized structures. The projections may comprise discrete surface structures or aggregated structures, including but not limited to hooks, barbs, tubes, rods, cones, spheres, cylinders, loops, pyramids, or a mix thereof. These structures may have a size in the range of about 5 nm to about 5 mm or more, sometimes about 50 nm to about 3 mm, and other times about 500 nm to about 1 mm, and in still other times about 1 µm to about 500 µm.

In one embodiment the coating and or covering can be used to stimulate a thrombotic or coagulant response, and/or organization of tissues or fluids it contacts. For example, the coating or covering may comprise a hemostatic agent such as chitosan, zeolite, fibrinogen, anhydrous aluminum sulfate, titanium oxide, one or more clotting factors or other constituents of the blood clotting cascade.

In some embodiments, one or more therapeutic agents may be mixed with a polymer material which may either biodegradable or non-biodegradable. Thus, release of the therapeutic agents may occur by elution from the polymer material, and/or by degradation of the polymer material. For example, an orthopedic device may comprise a material or reservoir being drug loaded and dissolvable through features provided in a jacketing or coating material, such as through micro holes, pores, or some other feature. In certain embodiments the articular layer is provided with reservoirs, depots, cavities, wells, pockets, porous materials, bubbles or capsules for drug delivery. In one specific example, the orthopedic device could be a drug-loaded element that slowly dissolves to elute a drug of some sort through a casing that is spongiform or porous. This would leave behind the casing after the ring has dissolved. In some embodiments, timed drug delivery could be configured for more controllable dosing. For example, about 75% to about 90% of a therapeutic agent may be released or dissolved over a timeframe of anywhere from about 4 hours to about 4 months or more, sometimes from about 24 hours to about 6 weeks or more, other times from about 72 hours to about 4 weeks, and still other times from about 2 weeks to about 4 weeks. In other embodiments, the casing would maintain the space filling or cushioning feature desired and/or allow for tissue organization or in-growth.

The therapeutic agent may be provided on an outer surface or an inner surface of the articular layer, or within a volume or layer of the articular layer. As mentioned previously, the articular layer may comprise one or more rate control layers to alter the rate of therapeutic agent release. The rate control layer may comprise, for example, polymer layers with a reduced permeability or smaller pore structure.

In one specific embodiment, a coating may comprise a xenograft, allograft or autograft biological covering, from a live and/or cadaveric donor, or a biological material grown from a tissue culture. For example, tissue harvested directly from the patient could be harvested using a laparoscope or other tissue removal and collection system and then affixed to the core, articular layer, preshaped ring or backbone and secured to the orthopedic device. The tissue may include but is not limited to omental tissue, ligamentous or tendinous tissue, cartilage tissue, bone tissue and the like. The graft material may retain the native tissue structure or may have undergone additional mechanical processing (e.g. crushing, blending, etc.) or biological processing (treatment with glutaraldehyde or other cross-linking agents, sterilization with electron-beam, gamma irradiation or ethylene oxide, etc.) The device could then be loaded into a delivery cannula and inserted and ejected (deployed) in the same fashion as the delivery systems employed and described herein. In some embodiments, the articular layer 105 comprises a cartilage replacement material, or a natural or synthetic cartilage.

In another embodiment, an orthopedic device is covered with a material, biological agent, or other coating that expands in volume with contact to fluids. The fluids may be the endogenous fluid found in the joint itself, and/or externally added fluids. Expandable materials may permit the insertion of a device of a diameter that is smaller than the fully expanded finished diameter. For example, a coating on the backbone or the articular layer could be hydrophilic in that it could transition from one configuration or diameter (small for insertion) to a larger configuration or diameter when contacting either the body fluid or some fluid provided from an outside source, such as saline.

In one specific embodiment, the expandable or swellable covering may comprise a composite or matrix with a polymer and a biological material i.e. tissue, including but not limited to cartilage, collagen, ligaments, muscle, etc. In one embodiment, the scaffold could be a polymer-based material. In various embodiments, the casing or covering of the orthopedic device is configured to swell from the small insertion dimension or diameter after implantation to a larger finished dimension or diameter. In some alternate embodiments, such as those disclosed in U.S. application Ser. No. 12/099,296, filed Apr. 8, 2008, the orthopedic device may comprise an inflatable structure. The inflatable structure may be inflated with a gas, liquid, gel, or slurry which may or may not be curable to a solid state. The inflatable structure may also be expanded by filling the structure with a volume of solid structures, such as microspheres or other small structures.

In certain embodiments, the articular layer 105 is radiopaque, and can augment the visibility of the device when implanted as viewed by X-ray and/or fluoroscopic equipment. In one embodiment, the radiopacity of the articular layer 105 is provided by radiopaque markers or structures (not shown here) on or embedded in the layer 105, or by loading or doping the articular layer 105 with platinum, gold or other biocompatible metal.

In various embodiments, any of the features of the articular layer or coatings mentioned herein may be combined on the orthopedic device, either as different layers of the orthopedic device or as different sections or regions of the orthopedics device. In one embodiment, an articular layer or coating can provide for tissue ingrowth or fusion with bone, cartilage, or other tissue while another surface provides a low-friction surface to another side of the joint. Any combinations are possible. In some embodiments, adhesives or transitional polymer layers may be provided to facilitate the attachment of two or more other layers of the articular layer.

As described previously, the orthopedic device can have an arcuate, rectilinear or non-straightened configuration once it is implanted in a joint. Some non-limiting examples of arcuate configurations include an open ring (also called an open hoop or an open loop) such as is shown in the embodiment in FIG. 1B, and a nautilus-style spiral as is shown in the embodiment in FIG. 1C. Referring to FIG. 1B, the open hoop arcuate configuration of the orthopedic device 100b has a proximal end 110b and a distal end 120b in relation to insertion into the body of a patient, such as into a joint. In certain embodiments, the orthopedic device 100b of FIG. 1B may have similar attributes and characteristics of the orthopedic device 100a of FIG. 1A, such as shape memory and/or an articular surface 105. In certain embodiments, orthopedic device 100b is an arcuate configuration of orthopedic device 100a. In certain embodiments, the orthopedic device 100a is biased to the configuration as shown for orthopedic device 100b. The bias may be a preferred configuration for a flexible, pliable, bendable device. In certain embodiments, the orthopedic device of 100a may change to from one configuration to another (e.g. from the configuration of orthopedic device 100a in FIG. 1A to the configuration of orthopedic device of 100b in FIG. 1B) by a change in ambient or implantation site temperature, by a release from deformation stresses, or by the introduction of an activating medium or material. In certain embodiments, the orthopedic device is reversibly configurable between various shapes or geometries.

As mentioned previously, the orthopedic device may also comprise a closed shape that forms a complete perimeter along at least one section or portion of the device. In FIG. 1D, for example, the orthopedic device 130a comprises an expanded configuration with a closed triangular shape. Although the triangular shape in FIG. 1D comprises an equilateral triangular shape with uniform angles 135a, 140a and 145a, in other embodiments, one or more angles may be different from the other angles. Also, although the inner angles 135a, 140a and 145a, along with outer angles 150a, 155a and 160a have sharp angles, in other embodiments, one or more of these angles may be rounded. In its collapsed state, depicted in FIG. 1E, the inner angles 135b, 140b and 145b of the orthopedic device 130b may narrow to collapse its triangular shape into an arrow shape. The orthopedic device 130b may also have a bending section 165a that collapses from a straight configuration to a bent configuration to facilitate the reduction in the cross-sectional profile of the orthopedic device 165b. Although the orthopedic device 130b is depicted as generally collapsing within the plane of the orthopedic device 130a in its expanded configuration, in some embodiments, this and other orthopedic devices disclosed herein may also fold onto themselves or otherwise collapse out of plane to reduce their cross-sectional profile. In other embodiments, the orthopedic device may comprise other polygonal shapes or curvilinear shapes, with angles and/or sides that may be uniform or different, with angles that narrow or widen when changing from one configuration to another configuration. Although several embodiments described herein have a base configuration that is the expanded or deployed configuration, in other embodiments, the base configuration may be the delivery configuration. In still other embodiments, the orthopedic device may comprise a malleable or plastic material or structure with any bias toward one or more configurations.

FIGS. 1F and 1G illustrate another embodiment of an orthopedic device 170a/170b comprising a closed arcuate configuration. In its deployed configuration, the orthopedic device 170a comprises a circular configuration, but other embodiments, may comprise an oval or ovoid shape (e.g. one end being larger than the other end). To transform the device 170a to its delivery configuration, the orthopedic device 170a shortens along a first dimension 175a while lengthening along a second dimension 180a. In some embodiments, the delivery axis of the orthopedic device 170b may be transverse to the first dimension 175b, or parallel to the second dimension 180b.

One example of a nautilus-style spiral arcuate configuration is the embodiment of an orthopedic device 100c as shown in FIG. 1C. The orthopedic device 100c has a proximal end 110c and a distal end 120c in relation to insertion into the body of a patient, such as into a joint. In certain embodiments, orthopedic device 100c has many similar attributes and characteristics of orthopedic device 100a and/or 100b, such as shape memory and/or an articular surface 105. In certain embodiments, orthopedic device 100b is an arcuate configuration of orthopedic device 100a. In certain embodiments, the orthopedic device of 100a may be altered in to a configuration as shown for orthopedic device of 100c. The bias may be a preferred configuration for a flexible, pliable, bendable device. In certain embodiments the orthopedic device 100a, when unconstrained, can change to the configuration as shown for orthopedic device of 100c, or by a change in ambient or implantation site temperature or the introduction of an activating medium or material. In certain embodiments, the orthopedic device is reversibly configurable between various shapes or geometries.

In some embodiments, the orthopedic device is configured to float inside the joint, which may better conform to the natural movement of the bones through the range of motion of the joint. The nautilus-style spiral arcuate configuration depicted in FIG. 1C, for example, may also offer certain advantages described for the open hoop arcuate configuration, or hoop configuration, but also provides a larger bearing surface to the joint. With the extended length of the spiral configuration, the orthopedic device 100c is configured to provide more of an articulate surface, which may result in decreased pressure on the bones by dissipating forces over a larger surface area. The cross-sectional diameter multiplied by the number of winds in a spiral shape roughly equals the surface area coverage of the articular surface in conformation with the bones of the joint. For example, a small cross-sectional diameter of a spiral configuration allows for a plurality of windings in the spiral. This plurality of spiral windings can then adjust to the general surface area of either bone as the joint articulates.

As noted previously, some embodiments of the devices can have additional structures within it. For example, in FIG. 2 an orthopedic device 200 comprises an elongate core 240 and an articular layer 230 surrounding at least a portion of the core 240. Referring back to FIGS. 1A-1C, various embodiments of orthopedic devices 100a, 100b and/or 100c can either have an elongate core or lack an elongate core. Other embodiments of orthopedic devices 100a, 100b and/or 100c may also either have an articular layer or lack an articular layer. Thus, the orthopedic device may consist of an elongate core, an articular layer, or both. In various embodiments directed to use in PIP, DIP and MCP joints, for example, the cross-sectional diameter or thickness of a core can range from roughly about 0.001 to about 0.60 inches (or about 0.025 to about 15 mm) with some embodiments in a range of roughly about 0.005 to about 0.015 inches (or about 0.13 to about 0.38 mm), and some embodiments in a range of roughly about 0.01 to about 0.0125 inches (or about 0.26 to about 0.32 mm). In various embodiments, the cross-sectional outer diameter or overall thickness of an articular layer can range from roughly about 0.003 to about 0.50 inches (or about 0.076 to about 12.7 mm) with some embodiments in a range of roughly about 0.039 to about 0.118 inches (or about 1 to about 3 mm), and some embodiments in a range of roughly about 0.078 to about 0.098 inches (or about 2 to about 2.5 mm). In some embodiments a ratio of core cross-sectional diameter (or thickness) to articular layer cross-sectional outer diameter (or thickness) can range from about 0.000 to about 0.500 inches, and in other embodiments may have ranges of ratios from about 2 to about 30. Other dimensions with the same, similar or different ratios can be used in other parts of the patient's body. Orthopedic devices with cores having other dimensions may also be used, including but not limited to orthopedic devices configured for larger joints such as the knee, hip, ankle, and shoulder, for example.

As illustrated in the embodiment of FIG. 2, the orthopedic device 200 may include the elongate core 240 in addition to the articular layer 230. In some embodiments, the articular layer 230 surrounds, encapsulates, encloses or covers at least a portion of the core 240. In some other embodiments, the articular layer 230 can surround or encapsulate the entire elongate core 240. As used herein, "surround," "encapsulate" and "enclose" include configurations in which a core is not completely surrounded, completely encapsulated or completely enclosed. For example, certain embodiments of an orthopedic device contemplate an articular layer which "surrounds" an elongate core with a continuous or non-continuous helical band, discontinuous tabs, or other intermittent articular layer structure.

In some embodiments, the articular layer 230 may have some or all of the features of other articular layer embodiments described herein. In one embodiment, the ratio of the cross-sectional size of the elongate core 240 to the articular layer 230 is in the range of about 10:1 to 1:10, sometimes in the range of about 5:1 to about 1:5 and other times with a ratio of about 2:1.

In one embodiment, the elongate core 240 comprises a shape memory material. The shape memory material may be made from a heat set/shaped shape-memory material, such as Nitinol, or a shape memory plastic, polymeric, synthetic material. For example, one embodiment of the elongate core 240 comprises a shape memory material including a shape memory polyurethane or polyurethane-urea polymer, as described above. In one embodiment the elongate core 240 comprises a metal "open" ring such as Nitinol encapsulated by an articular layer 230, or outer blanket, comprising silicone. In one embodiment the elongate core 240 comprises a hardened polymer. In one embodiment, the elongate core 240 is configured such that a heat set Nitinol with an arcuate configuration, such as an open ring configuration, a horseshoe configuration, or a spiral configuration, can be straightened for delivery through cooling or plastic deformation, then recovered to its original heat-set shape once released from a delivery system, such as one embodiment using a properly sized hypodermic needle. In one embodiment the elongate core 240 comprises a non-shape memory material which can be bent or deformed.

In certain embodiments, the elongate core 240 is coated or impregnated with a drug or other therapeutic agents as described previously with respect to the articular layer. The therapeutic agents of the elongate core 240 may be the same or different from the therapeutic agents of the articular layer or other layers or coatings of the orthopedic devices.

FIGS. 3A to 3E are longitudinal cross-sectional views of the orthopedic devices 100a to 100c in FIGS. 1A to 1C with various configurations of optional support structures or cores. FIG. 3A is a schematic cross-sectional view of an orthopedic device 300a comprising a substantially straightened configuration. In this embodiment, the device comprises an elongate core 340a and an articular layer 330a surrounding at least a portion of the core 340a. The articular layer 330a has a proximal end 331a and a distal end 332a. The elongate core 340a has a proximal end 341a and a distal end 342a. In one embodiment, the orthopedic device 300a may be a cross-sectional view of the orthopedic device 100a described above, with a core 340a. FIG. 3B shows a device an elongate core 340b and an articular layer 330b surrounding at least a portion of the core 340b in an open hoop arcuate configuration. The articular layer 330b has a proximal end 331b and a distal end 332b, while the elongate core 340b has a proximal end 341b and a distal end 342b. In one embodiment, the orthopedic device 300b may be a cross-sectional view of the orthopedic device 100b described above. Certain embodiments of a spiral shaped device, such as is shown in FIG. 3C can have a single elongate core. For example, orthopedic device 300c comprises a nautilus-style spiral arcuate configuration, the device comprising an elongate core 340c and an articular layer 330c surrounding at least a portion of the core 340c, the articular layer 330c comprises a proximal end 331c and a distal end 332c, and the elongate core 340c has a proximal end 341c and a distal end 342c. In one embodiment, the orthopedic device 300c may be a cross-sectional view of the orthopedic device 100c described above.

In some embodiments, the elongate core may be wrapped around itself or comprise of a number of distinct or separate sections or segments, as shown in FIGS. 3D and 3E. FIG. 3D shows an orthopedic device 300d with an open hoop arcuate configuration. In one embodiment, the orthopedic devices 300d may be a cross-sectional view of the orthopedic device 100b described above, with an optional folded or overlapping core 340d. The device 300d comprises one or more elongate cores 340d wrapped, braided or folded back along a length of the device, and an articular layer 330d surrounding at least a portion of the core(s) 340d. The articular layer 330d has a proximal end 331d and a distal end 332d. The elongate core 340d in FIG. 3D comprises a unitary body with a proximal end 341d, a distal end 342d, an inner segment 350d, a middle segment 352d and an outer segment 254d. The segments 350d to 354d may be interconnected as depicted in FIG. 3D, but in other embodiments may one or more segments may be separated. The segments of the embodiments described herein may themselves have subsegments, e.g. the inner segment 350d may comprise a proximal segment and a distal segment. Also, the segments of a core may generally have a similar length, such as segments 350d to 354d in FIG. 3D, but one or more segments may also have a different length In some embodiments for example, two or more elongate cores 340d are situated in a roughly parallel or co-linear orientation, which can be twisted or braided or interlocked. Other embodiments of the orthopedic device need not be limited to a single elongate core or backbone, but may have a plurality of cores or backbones including a braided configuration, continuous overlaps, etc. FIG. 3E shows an orthopedic device 300e with a nautilus-style spiral arcuate configuration. In some embodiments, the orthopedic device 300e may be a cross-sectional view of the orthopedic device 100c described previously, but with an optional folded or overlapping core 340e. The device 300e comprises one or more elongate cores 340e wrapped or folded along a length of the device and an articular layer 330e surrounding at least a portion of the core(s) 340e. Although the core 340e generally extends from one end 331e of the orthopedic device 300e to the other end 332e, in other embodiments, the core 340e may extend out from the articular layer 330e at either or both ends 331e, 332e of the orthopedic device 300e, or anywhere between the two ends 331e and 332e. In other embodiments, the core 330e may have a length that is substantially less than the length or the orthopedic device 300e. For example, the core may be provided only along the outer spiral portion of the orthopedic device, leaving the inner overlapping portion of the orthopedic device with a portion of the core. In other embodiments, only the inner portion of the orthopedic device may comprise a core, while the outer overlapping portion lacks a core.

FIGS. 3F and 3G depict one embodiment of the orthopedic device 170a and 170b depicted in FIGS. 1F and 1G configured with one or more optional cores. As shown in FIG. 3F, in the orthopedic device 170c in the expanded configuration comprises two separate cores 180c and 182c. In other embodiments, the orthopedic device may have a single core, or three or more cores, including but not limited to four cores, five cores, or six cores, for example. The cores may have substantially similar lengths or their lengths may be substantially different. The cores may also have substantially similar or different cross-sectional or elongate shapes. In some embodiments, the cores 180c and 182c may be separate but arranged in contact with each, or they may be separated by non-core sections 184c and 186c at one or both ends 188c, 190c, 192c and 194c of the cores 180c and 182c. In some embodiments, the non-core portions of an orthopedic device may facilitate a particular collapsed configuration. For example, the narrow oval configuration of the orthopedic device 170d in FIG. 3G illustrates how the non-core sections 184d and 186d may permit substantial bending in the collapsed state compared to portions of the orthopedic device 170d along the cores 180d and 182d. In some embodiments, the perimeter or length of the orthopedic device, whether having an open or closed configuration, may comprise a ratio of core to non-core portions in the range of about 0 to about 1, sometimes about 0.3 to about 1, and other times in the range of about 0.7 to about 0.95.

Figure 4B:
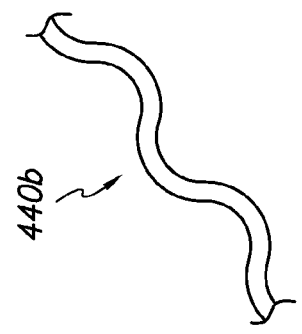
FIG. 4B is a schematic side view of an embodiment of an elongate core comprising one or more wave, curve or zig-zag members disposed in one or more planes.
Figure 4C:
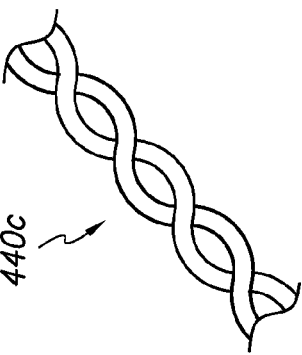
FIG. 4C is a schematic side view of an embodiment of an elongate core comprising one or more members in a braided or weave configuration.

The shape of the elongate core can vary, as is shown in embodiments in FIGS. 4A to 4C. FIG. 4A shows an elongate core 440a with one or more substantially linear or straight members. FIG. 4B shows an elongate core 440b with one or more wave, curve or zig-zag members that may be in one or more planes at any angle with respect to one another. FIG. 4C shows an elongate core 440c with one or more members in a braided or weave configuration. Any of these patterns can be used with any of the elongate cores disclosed herein.

Figure 5A:
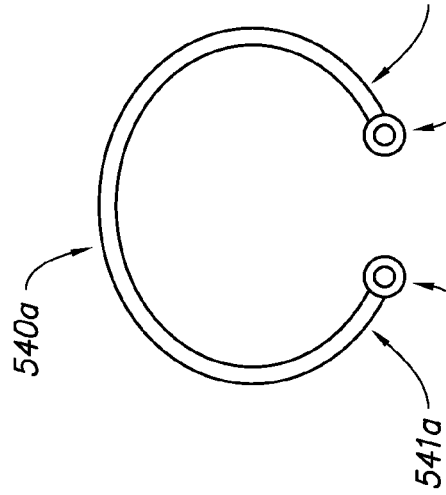
FIG. 5A is a schematic top view of an embodiment of an elongate core comprising an open hoop arcuate configuration and one or more end pieces.
Figure 5B:
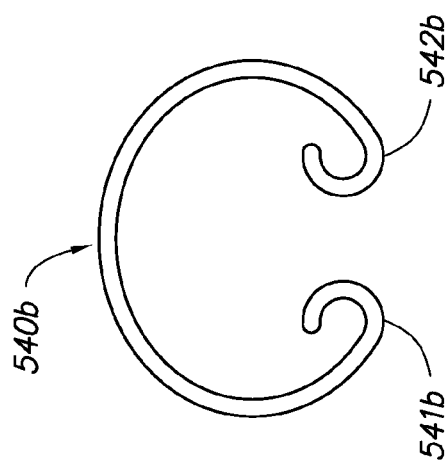
FIG. 5B is a schematic top view of an embodiment of an elongate core comprising an open hoop arcuate configuration and one or more bends or hooks.
Figure 5C:
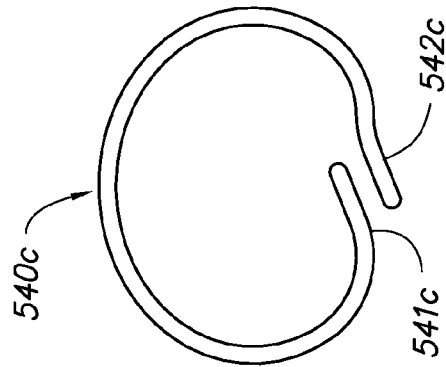
FIG. 5C is a schematic top view of an embodiment of an elongate core comprising an open hoop arcuate configuration and one or more features bent in or out of the primary plane of the device.

Various embodiments of elongate cores can have different features along the length or ends of the core, as is shown in FIGS. 5A-5C. An elongate core 540a with an open hoop arcuate configuration can have one or more end segments, as is shown in FIG. 5A. Such end segments can include proximal end segment 561a and/or distal end segment 562a. In some embodiments, the optional end segments 561a and/or 562a may be configured with an enlarged axial cross-sectional area compared to the portions of the core 540a between the end segments 561a, 562a. The end segments may have any of a variety of configurations, including but not limited to the ring or loop configurations depicted in FIG. 5A. In other embodiments, the end segments may have a T-tag configuration, a spherical or ovoid configuration, a helical or spiral configuration, or any other configuration. The orientation of the end segments may lie within the plane of the rest of the orthopedic device, or may be perpendicular, transverse or some non-planar orientation with respect to the orthopedic device. The configuration of each end segment, if any, may be the same or different. Each end segment may be embedded within the articular layer of the orthopedic device, but in some embodiments, some or all of the end segments may at least partially project from the articular layer or otherwise be exposed with respect to the articular layer. In one particular example, the end segments 561a and 562a of FIG. 5A may be exposed so that the ring configurations may be used to attach a suture or other structure to the orthopedic device. In other embodiments, the end segments 561a and 562a may help to resist relative separation or displacement of the articular layer and the core 540a, and/or to reduce the risk that ends of the core 540a may penetrate through the articular layer of the orthopedic device. In various embodiments, the elongate core or cores 540a can have zero, one, two or more end segments. In one embodiment the end segment 561a or 562a is radiopaque or can be used as a marker for visualization of the ends of the orthopedic device. The end segments 561a and 562a may comprise the same or different material as the length of the elongate core 540a. In one embodiment, the end segments 561a and 562a are separate elements made of the same or different material as the length of the elongate core 540a and which are bonded, fused, welded, glued, or otherwise attached to the proximal end 541a and a distal end 542a, respectively.

Although not illustrated, it is contemplated that an elongate core 540a may have one or more medial segments anywhere along the length of the elongate core 540a. In various embodiments, elongate core 540a has end segments or medial segments to help improve stability of an articular layer or outer blanket, and need not be flat or planar, but can be biased out of the primary plane of the device at one end or both ends.

In another embodiment, an elongate core 540b may include one or more bends, such as proximal bend 541b and/or distal bend 542b as shown in FIG. 5B. In some embodiments, the bends may also include hooks. In various embodiments, the bends or hooks can be closed off to form a loop, as with certain embodiments of elongate core 540a. The bends 541b and/or 542b may be generally oriented radially inward, as shown in FIG. 5B, or radially outward. The bends may or may not have the same orientation. For example, the elongate core 540c shown in FIG. 5C comprises a proximal segment 541c that is bent radially inward from the curvature of the elongate core 540c and a distal segment 542c that is bent radially outward with respect to the overall configuration of the elongate core 540c. In other embodiments, proximal segment 541c and/or distal segment 542c are bent radially inward, radially outward, and/or up or down from the primary plane of the elongate core 540c. FIG. 5E, for example, depicts an embodiment of an orthopedic device 570e with its ends 572e and 574e oriented out-of-plane in a relative upward direction. The orthopedic device 570e may optionally comprise an arcuate core (not shown) with ends that are bent out-of-plane. Thus, in embodiments where the core of the orthopedic device comprises ends which are biased or bent slightly towards or away from its center, the optional core or support structure of the orthopedic device may be similarly configured. In other embodiments, however, the general configuration of the core and the general configuration of the articular layer or the orthopedic device may be the same or may be different.

FIG. 5D schematically illustrates another embodiment of a non-planar orthopedic device. In this particular embodiment, the portions of the orthopedic device 570d at each end 572d and 574d may have a generally planar configuration, with by a compressible axial member 576d therebetween. The axial member 576d may have a multi-angle configuration, as shown in FIG. 5D, but may also comprise a multi-curved or helical configuration, for example. In some embodiments, the planar ends 572d and 574d of the orthopedic device may facilitate the alignment of the orthopedic device 570d with the articulating surfaces of bones of a joint. In some embodiments, the orthopedic device with a multi-planar configuration may augment the shock absorbing characteristics of the orthopedic device, including orthopedic devices that undergo frequent or substantial axial loading, such as a knee joint. Here, the configuration of the axial member 576d may modify the axial loading characteristics of the joint relative to an orthopedic device with a generally planar configuration.

In embodiments of the orthopedic devices comprising elongate cores, the cores may have any of a variety of cross-sectional structures or profiles. For example, some cross-sectional profiles of various embodiments of elongate cores are shown in FIGS. 6A to 6K. The illustrated embodiments are not limiting, but merely examples of various possible cross-sectional profiles of any of the embodiments of elongate cores or orthopedic devices described herein. The illustrated embodiments shows a variety of possible cross-sectional shapes for embodiments of the device or the core of the device, including a square, ellipse, triangle, etc., and wherein the elongate core can be modified by twisting, and zig-zagging, and/or undergo one or more surface treatments such as abrading or pitting, for example.

FIG. 6A illustrates a cross-sectional view of an embodiment of a circular profile elongate core 640a, which can be rotated along a longitudinal axis of the core 640a. In various embodiments, the elongate core 640a is at least partially surrounded by an articular layer, wherein the elongate core 640a and/or the articular layer transition between a straight or slightly curved configuration to a more curved or arcuate configuration. During this change in configuration, elongate core 640a and the articular layer may rotate with respect to each other. In one embodiment, the elongate core 640a and the articular layer has some frictional engagement, which may interfere with rotation between the elements, resulting in some level of deformation. Furthermore, in one embodiment, both the elongate core 640a and the articular layer will have different material properties which are dependent on stiffness, durometer and other aspects of the respective materials. Depending on the desired orientation of an orthopedic device during delivery to a joint, the orientation of the elongate core 640a and/or the articular layer may be controlled by the configuration of the delivery device being used.

In certain embodiments, an elongate core may be configured with a non-circular cross-sectional shape. For example, FIGS. 6B to 6K illustrate cross-sectional views of a triangular profile elongate core 640b, a rectangular profile elongate core 640c, a trapezoidal profile elongate core 640d, an oval or elliptical profile elongate core 640e, a ridged profile elongate core 640f, a non-symmetric profile elongate core 640g, a cross or X-profile elongate core 640h, a lumen profile elongate core 640i, a pentagon profile elongate core 640j, and a hexagon profile elongate core 640k, respectively. In some embodiments, a non-circular profile may be used to resist or limit relative rotation or torsion of an articular layer and the core. Although several of the embodiments disclosed herein comprise one or more cores with an elongate configuration, in other embodiments, the cores may comprise a branching or interlinking structure that may have a generally planar or a generally non-planar structure. For example, some orthopedic devices may have a core with a "Y"-shape or "X"-shape branched configuration, with the arms or segments of the core arranged in a generally the same plane. Other orthopedic devices may also have a "Y"-shape or "X"-shape branched configuration but in a non-planar arranged, such as a three-leg or four-leg tripod arrangement, for example, where the intersection point of the "Y"-shape or "X"-shape is located in a different plane as one or more of the ends of the arms or segments. Embodiments of orthopedic devices having branched cores may or may not have articular layers are also branched, and embodiments of orthopedic devices with branched articular layers may or may not have branched cores.

In some embodiments, the articular layer of the orthopedic device may also comprise a non-circular cross-sectional shape. The cross-sectional shape of elongate core of such orthopedic devices, if any, need not have the same or similar the cross-sectional shape of the articular layer. In FIGS. 6L and 6M, for example, the orthopedic device 642L comprises an articular layer 644L with a rectangular axial cross-sectional shape and an elongate core 640L with a circular axial cross-sectional shape. The larger dimension 646L, if any, of the rectangular articular layer 644L may be generally oriented within the plane 648L of the orthopedic device 642L, while the shorter dimension 650L, if any, (or a dimension transverse to the larger dimension 646L) may be generally oriented transverse to the plane 648L of the orthopedic device 642L. In other embodiments, the orientation may be opposite, or may be at any other angle or orientation with respect to the plane of the orthopedic device, if any, or other geometric reference of the device, including but not limited to the longitudinal axis or a center axis of the orthopedic device, if any. The core 640L of the orthopedic device 640L may be generally centered along the larger dimension 646L and the shorter dimension 648L, e.g. at a position about 50% along the larger dimension 646L and the shorter dimension 648L. In other embodiments, the relative position of the core 640L may be located anywhere from about 0% to about 100% along a particular dimension, including about 10%, about 20%, about 30%, about 40%, about 60%, about 70%, about 80% and about 90%, for example. The relative position of the core may be generally uniform throughout the orthopedic device, or may vary depending upon the particular section of the orthopedic device. In further embodiments, where a portion of the core extends beyond an inner or bottom surface, or an outer or upper surface of the articular layer with respect to a particular dimension, the relative position may be expressed as a negative percentage or a percentage greater than 100%. In some embodiments, for example, the position of the core may be located at about −10%, about −20%, about −30%, about −40% or about −50% or lower, or about 110%, about 120%, about 130%, about 140% or about 150% or greater. The orthopedic device in FIG. 6L also illustrates that the C-shape or arcuate configurations described herein are not limited to generally circular devices, and may include generally oval devices.

FIGS. 6N and 6O depict another embodiment of an orthopedic device 642N, comprising an articular layer 644N with a cross-shape cross-sectional shape along with a circular core 640N. FIG. 6P depicts another embodiment of an orthopedic device 642P, comprising a triangular articular layer 644P and a circular core 640P. In contrast to orthopedic devices 642L and 642N in FIGS. 6L and 6N, respectively, which depict open configurations, FIG. 6P illustrates an orthopedic device 642P with a closed configuration, as well as a cross-sectional shape that varies from one section 652P to another section 654P. Both features, however, need not be found in the same orthopedic device. In this particular example, one section 652P comprises an isosceles triangular shape while the other section 654P comprises an equilateral triangular shape. The different shapes of two or more sections of an orthopedic device, if any, may share one or more shape features (e.g., both may be triangular or polygonal), but in other embodiments, may be completely different (e.g. one section may have a small circular shape, while another section may have a large irregular octagonal shape).

FIG. 6R depicts still another embodiment of an orthopedic device 642R, comprising an articular layer 644R that has a non-polygonal cross-sectional shape that is non-uniform, along with a non-circular core 640R. As shown in FIG. 6S, one section 652R of the articular layer 644R comprises a superior protruding edge 656R and an inferior protruding edge 658R, both of which have a reduced profile in other section 654R of the device 642R. Furthermore, the inner protrusion 660R of one section 652R may also have a different profile compared to another section 654R. Still another feature of the device 642R is the presence of a second core 662R within the articular layer 644R. In this particular embodiment, unlike the primary core 640R, the second core 662R may be located in only a portion of the device 642R, such as the inferior protruding edge 656R, and may not extend along the entire circumference or perimeter of the device 644R.

FIGS. 6T and 6U depict another embodiment of an orthopedic device 642T, comprising a core 640T, an articular layer 644T and a span member 674T that crosses at least a portion of the inner region 676T of the orthopedic device 642T. In this particular embodiment, the span member 674T comprises a membrane having a generally uniform thickness and a planar configuration located generally midway between the superior surface 678T and the inferior surface 680T of the orthopedic device 640T. In other embodiments, the span member have a variable thickness, including one or more openings, depressions or grooves along one or more surfaces of the span member. In addition to planar configurations, the span member may have one or more regions with a non-planar configuration, including corrugated, concave, or convex regions, for example. The span member 674T may comprise the same or different material as the articular layer 644T, and may or may not be attached or embedded with reinforcement structures, e.g. wires, struts or meshes.

FIGS. 6V and 6W depict one example of an orthopedic device 642V with a span member 674V comprising a membrane structure with a convex configuration with respect to the superior surface 678V of the orthopedic device 642V. The span member 674V further comprises one or more through openings 682V arranged in a grid-like order, and with a generally cylindrical shape on cross-section, as shown in FIG. 6W. In other embodiments, one or more openings may have a non-circular shape (e.g. elliptical, ovoid, squared, rectangular, trapezoidal, or polygonal), have a non-uniform shape or diameter (e.g. tapered, toroidal), have a non-linear elongate configuration (e.g. angled or undulating), or any combination thereof.

FIG. 6X depicts another embodiment wherein a plurality of span members 674X are provided across the inner region 676X of the orthopedic device 642X. As shown in FIG. 6X, the span members 674X has an elongate configuration with a generally parallel orientation with respect to one another. In other embodiments, however, one or more span members may have a non-parallel or overlapping configuration with respect to another span member. Each of the span members 674X may be symmetrically oriented with respect to a midline through the orthopedic device, but may also be asymmetrically oriented. The span members 674X in FIG. 6X have any of a variety of cross-sectional shapes (e.g. circular, elliptical, ovoid, squared, rectangular, trapezoidal, or polygonal), and may have uniform or non-uniform cross-sectional areas or shapes along their elongate length.

Figure 6Y:
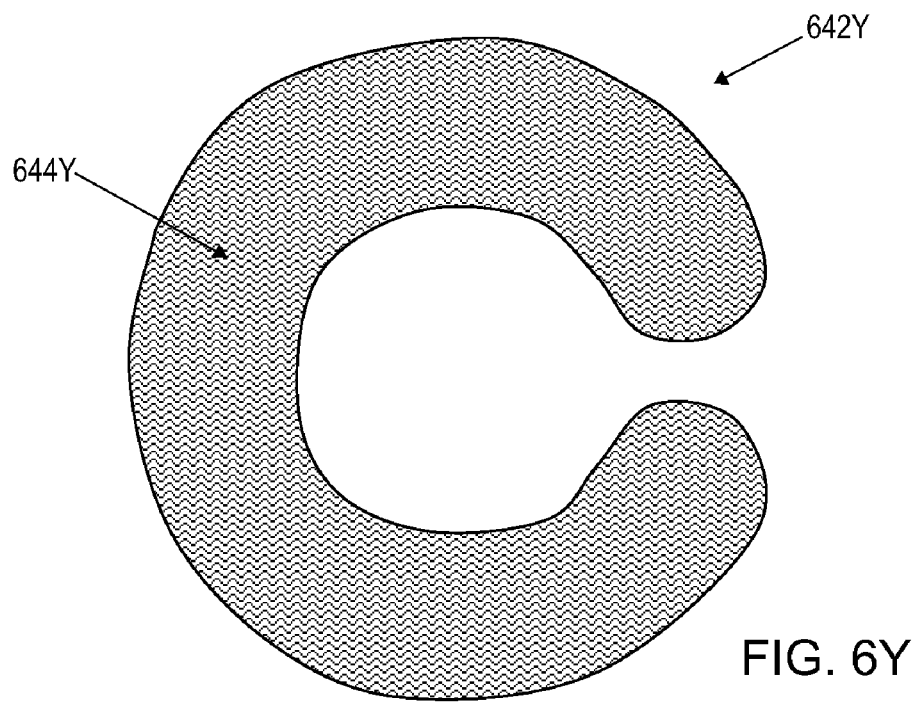
FIG. 6Y is a schematic superior view of an embodiment of an orthopedic device comprising a textured surface.

As mentioned previously, the articular layer of the orthopedic device may comprise a smooth outer surface, or a porous or textured surface. In FIG. 6Y, for example, the articular layer 644Y of the orthopedic device 642Y comprises a textured surface with series of ridges having a repeating angular or oscillating pattern. As mentioned previously, in other embodiments, the textured surface may comprise other types of surface structures, including but not limited to discrete or aggregated microstructures or nanostructures, such as grooves, pores, indentations, hooks, barbs, tubes, rods, cones, spheres, cylinders, loops, pyramids, or a combination thereof. The surface of the orthopedic device or its articular layer may be completely or partially covered with the surface textures, and the density, spacing or size of the ridges or other surface structures may be uniform or non-uniform. In the embodiment depicted in FIG. 6Y, the ridges generally have the same orientation regardless of the particular section of the articular layer 644Y, but in other embodiments, the ridges, structures or textures may be aligned or oriented in any of a variety of other ways, including but not limited to with respect to the longitudinal axis of the orthopedic device 644P, or circumferentially around the device 644Y, for example.

Figure 6Z:
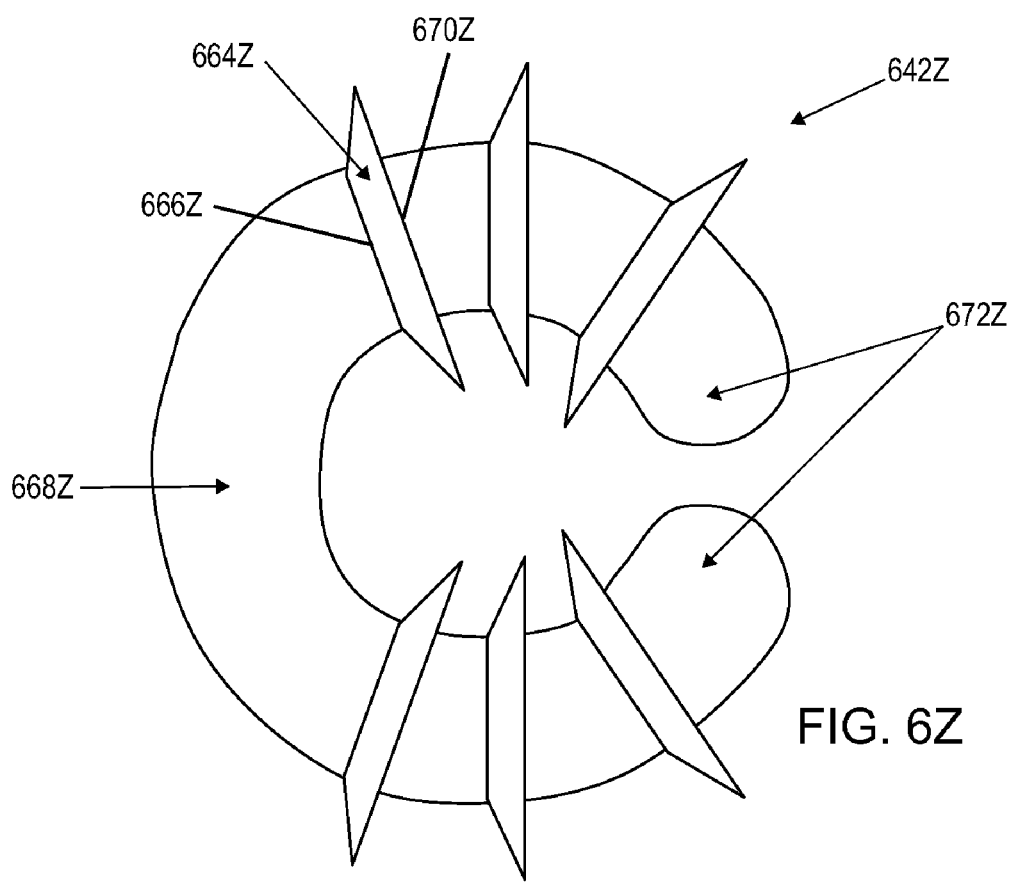
FIG. 6Z is a schematic superior view of an embodiment of an orthopedic device comprising one or more retaining structures.

In some embodiments, larger structures may be provided on the surface of the orthopedic device, in addition or in lieu of surface texturing. In FIG. 6Z, for example, an orthopedic device 644Z comprises a C-shape configuration with one or more ridges or flanges 664Z having a size that alters a gross dimension of the orthopedic device 644Z by about 5% or more. In this specific example, the flanges 664Z have a circumferential configuration around the body of the orthopedic device 644Z and are angled such that the narrow end 666Z of the flange 664Z is closer to the middle portion 668Z of the orthopedic device 644Z while the wider end 670Z of a flange 664Z is closer to the ends 672Z of the orthopedic device 644Z. In other embodiments, the larger structures may comprise large grooves or indentations, or other types of projecting surface structures. These larger structures may be rigid, semi-rigid or flexible, and each structure can have the same or a different configuration, size or material composition. In some embodiments, the flanges 664Z may resist migration or displacement of the orthopedic device 644Z within the joint space and/or out of the joint capsule.

In one embodiment, the articular layer can be at least partially attached to the outer surface of a portion of a backbone or core, either during or after implantation. In one non-limiting example, a core or backbone or wire of fixed length is implanted in a joint, then an articular layer or jacket is advanced over the core. In alternative embodiments, the articular layer is positioned in the joint first, followed by the insertion of the core through the articular layer. The core or backbone or wire is cut to size for a joint and is implanted in a joint, then an articular layer or jacket is advanced over the core. The articular layer or jacket may also be shaped or sized before being advanced over the core. In various embodiments, the core could have a feature such as a ball or hook at one or both ends (proximal and distal) so that when the articular layer is advanced over the proximal end of the core, the articular layer can abut against a distal feature or stop. In still other embodiments, the core may comprise a roughened outer surface, barbs, or other interference structures that resist separation from the articular layer. In an embodiment with a proximal feature such as a ball or cap, the articular layer may be trapped or held in position between the features to resist separation from the core. In other embodiments, heat bonding or adhesives may be used to attach the articular layer to the core. In one embodiment the articular layer can be implanted without a backbone or core.

Some embodiments of an elongate core include a plurality of inter-connectable discrete elongate members, as shown in FIGS. 7 to 9C. In various embodiments, two or more discrete articular structures or members may be connected along a single core wire or a plurality of core wires or elements. In embodiments comprising a plurality of core elements, a separate core element may be used to connect each adjacent pair of articular members, or multiple core elements may be used. In other embodiments, one or more discrete articular members are configured to facilitate or permit rotation or spinning about the connector or core wire. In another embodiment one or more discrete elongate members are affixed to the connectors or core wire in a manner to reduce or prevent rotation of the elongate members with respect to connector or core wire. For example, multiple core wires may be beneficial in resisting rotation of an articular structure around a single core element. As illustrated in FIG. 7A, one embodiment of an orthopedic device 740a comprising a plurality of inter-connectable discrete elongate members 742, 744 and 746 which are linked by connector 760. In some embodiments, the connector 760 can be a single core member extending between all the discrete elongate members 742, 744 and 746, or it can be any number of discrete connecting members between the elongate members. In one embodiment, the connector is flexible or malleable such that orthopedic device can be arranged in a variety of non-linear configurations. In FIG. 7B, for example the orthopedic device may be manipulated to orthopedic device 740b with a plurality of independent or interconnectable discrete elongate members 742, 744, 746 and 748 can having a "W"-shape generally rectilinear configuration. The connectors 760 can be configured to orient the elongate members such as 742, 744, 746 and 748 in any number of orientations or angles, in or out of plane. In some embodiments, the connectors 760 can have shape memory configurations or biases for particular orientations, depending on the doctor's preference or the device selected. The overall shape of an orthopedic device may comprise a "C", "O" and "W"-shape, but the device and/or articular layer and/or elongate core can specific any shape or configuration or general class of shape or configuration as mentioned elsewhere herein. FIG. 8 illustrates an alternate embodiment where the orthopedic device 840 comprises non-elongate interconnected articular members 841, 842, and 843 which are linked by a connector 860 passing through each member 841, 842 and 843, for example. The articular members, may have any of a variety of other shapes and configurations, and need not have a uniform size and shape, or comprise the same material.

In some embodiments, the orthopedic device may be marked to indicate orientation of the device. For example, the orthopedic device can be marked with any of a variety of graphical or other detectable indicia, including but not limited to a symbol, text, colors, magnetic radiographic markers or inks, or other types of markings that can be sensed visually or otherwise with or without the assistance of sensors or other devices, to indicate a side or feature that should be directed to a specific location. In some embodiments, identifying the orientation of an orthopedic device when it is deformed to a substantially straightened configuration may be addressed by markings or other indicia on the device to provide an indication of the orientation of the device. The indicia can be helpful for checking proper function or delivery of the orthopedic device. In some embodiments, the device or a component thereof may comprise a material that has electroresistive property which may change when the device or component is stressed or deformed. Changes in these or other electrical properties may be used as assess the forces acting on the device.

In some embodiments, the orthopedic device may comprise one or more articulations to facilitate configuration changes, in addition or in lieu of flexible interconnecting structures and/or materials. In one embodiment, for example, an elongate core 940a may comprise a plurality of inter-connectable discrete members, or links 950a, in a substantially straightened configuration, as shown in FIG. 9A. The elongate core 940a may be described as a multi-link elongate core, multi-link core, multi-link orthopedic device, or multi-link orthopedic implant. The multi-link orthopedic device may comprise a series of rigid or flexible links configured to translate the multi-link core from a straight or slightly curved configuration into a curved orientation or configuration. The diameter of curvature of the device could be adjustable by the ratcheting features provided on each link 950a. In one embodiment the links 950a are made of a material that can undergo some level of elastic deformation. In another embodiment, the links 950a are made of a more rigid material. With embodiments of the device, core, or link that are made from a superelastic material such as Nitinol, the implant can be straightened from its curved, deployed or implanted configuration and placed in a needle or cannula. Using an angled or curved delivery system, such as one shown in FIG. 10C below, would allow a more-rigid arcuate implant to be slightly straightened enough for insertion, but not enough to cause yielding.

FIG. 9B shows a side view of one link 950b. In one embodiment, link 950b is a link 950a of FIG. 9A. In one embodiment link 950b comprises a first end 951 and a second end 952. Various links 950b are inter-connectable between the second end 952 of a first link 950b and the first end 951 of a second link 950b', and in one embodiment the interconnection is a hinged connection between a first link interface 990 and a second link interface 980. In other embodiments, other connections or joints may be used, such as a ball-and-socket joint, a pivot joint, or a saddle joint, for example. Each link connection need not be the same type of connection. In one embodiment, the first link interface 990 is a post and the second link interface 980 is a channel in which the post is captured to allow rotation. In another embodiment, the second link interface 980 is a post and the first link interface 990 is a channel in which the post is captured to allow rotation. In various other embodiments, other link interfaces allowing some rotation including snap fits, connectors, or other similar interfaces may be used. In the illustrated embodiment, the link 950b comprises a ratchet prong 960 and ratchet teeth 970. The ratchet teeth 970 of one link 950b interact with the ratchet prong 960 of a second link 950b' to allow rotation with respect to links 950b and 950b' while restricting or limiting rotation in the opposite direction.

Various link embodiments may be configured to an arcuate configuration, as in FIG. 9C, which shows an elongate core 940c with links in an arcuate open loop configuration. In one embodiment, the elongate core 940c is actuated and locked into an arcuate configuration by the ratcheting mechanism as described above. In one embodiment the ratchet locking is configured to be disengageable such that the prong is releasable from the teeth to allow the elongate core 940c to rotate in a straight or less-curved configuration.

The orthopedic devices described herein may be implanted using any of a variety of implantation procedures. Although certain embodiments are configured for minimally invasive implantation, surgical implantation using an open procedure is also contemplated. The orthopedic device described herein may be implanted or be adapted for implantation into a variety of joints, including but not limited to the DIP and PIP joints of the hands and feet, the metatarsal-phalangeal joints, the tarsal-metatarsal joints, the metacarpal-phalangeal joints, the carpal-metacarpal joints, the ankle joints, the knee joints, the hip joints, the joints of the spine, including the facet joints, the glenohumeral joint, the elbow joint, the temporomandibular joint and others.

Figure 10A:
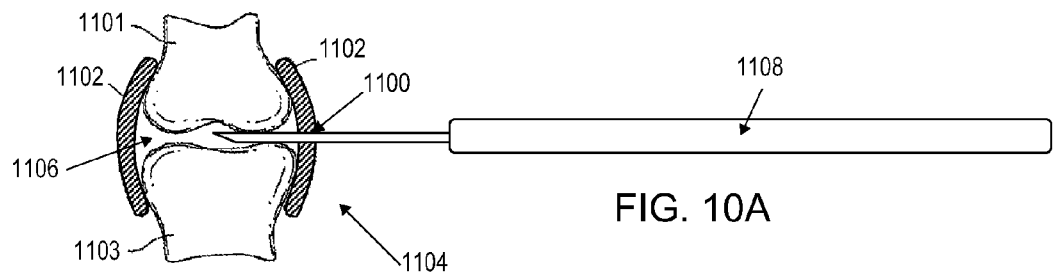
Figure 10B:
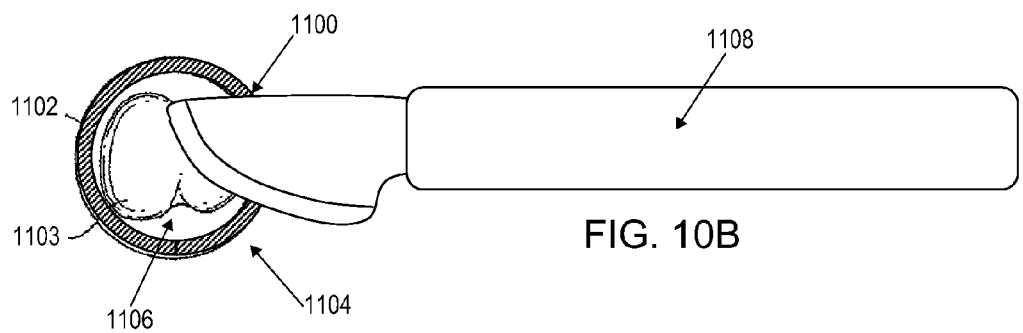

For example, in one embodiment, an arcuate orthopedic device is removed from its sterile packaging and optionally soaked in sterile saline. The joint is palpated or otherwise identified, with or without traction or other joint manipulation (e.g. flexion, extension). The skin region about the patient's affected joint is prepped and draped in the usual sterile fashion, and local, regional or general anesthesia is achieved. An anesthetic such as Marcaine, or other type of fluid such as sterilized water or a contrast agent, may be injected into the joint to cause joint distraction. As depicted in FIGS. 10A and 10B, an arthrotomy incision 1100 is made through the joint capsule 1102 of the joint 1104 to access the joint space 1106. In some embodiments, the arthrotomy incision may be performed using a stab or cut incision from a trocar or a scalpel 1108, for example. The joint space 1106 may be optionally irrigated, and any osteophytes and/or loose cartilaginous material may be removed.

Figure 10C:
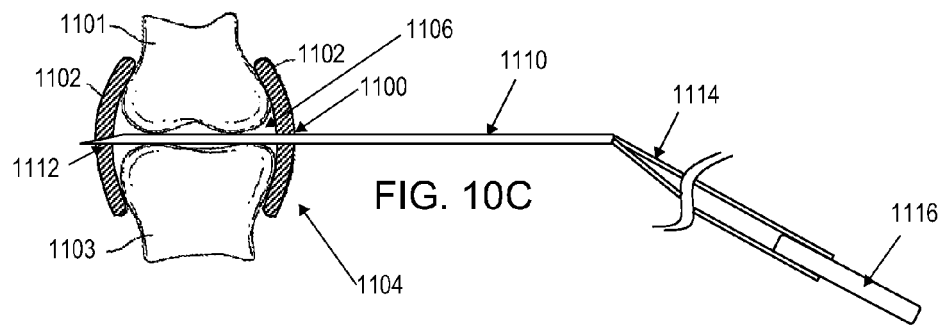
Figure 10D:
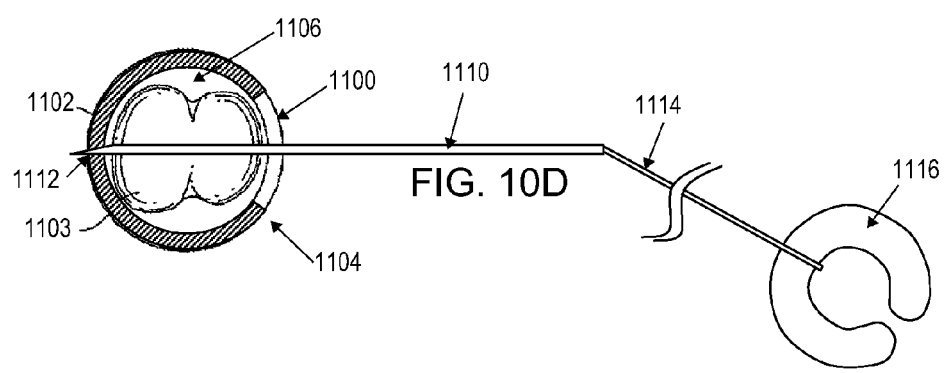
Figure 10I:
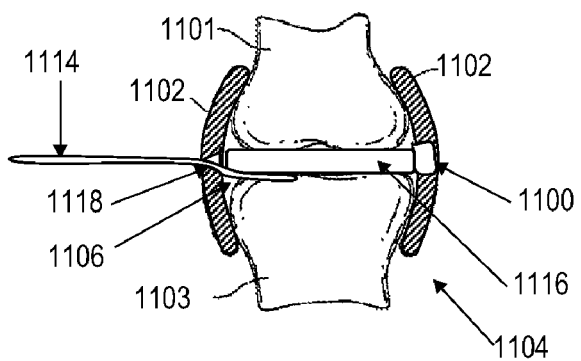
Figure 10J:
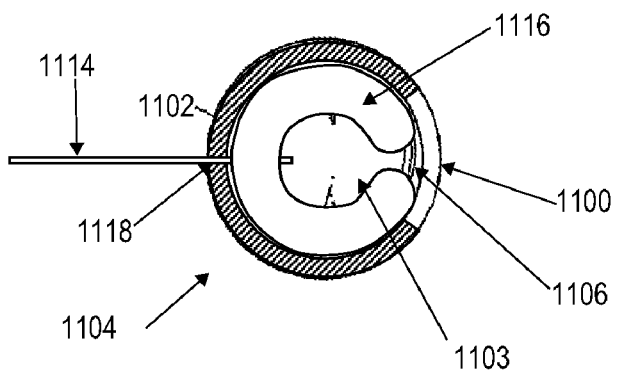

In some embodiments, the incision 1100 or opening may be large enough to insert the orthopedic device without requiring its deformation, but in other embodiments the incision 1100 may be smaller than the insertion profile of the orthopedic device. A Freer elevator, or other type of tissue retracting tool, may optionally be placed into the incision 1100 or opening to facilitate insertion of other components into the joint space. Referring next to FIGS. 10C and 10D, a needle 1110 is then inserted through the incision 1100 or opening and passed through joint space 1106 until it reaches a portion 1112 of the joint capsule 1102 opposite the incision 1100 and penetrates through the opposite skin surface. As the needle 1110 passes through the capsular and skin tissue, a suture 1114 or other tether structure coupled to the needle 1110 and to an orthopedic device 1116 is pulled through the joint space 1106 along with the orthopedic device 1116. As illustrated in FIGS. 10E and 10F, as the orthopedic device 1116 traverses the incision 1100 or opening, the orthopedic device 1116 may deform or collapse to better fit through a smaller incision 1100 or opening. In FIGS. 10G and 10H, as the orthopedic device 1116 passes through the incision 1100 or opening and into the joint space 1106, the orthopedic device 1116 may revert or expand back to its native configuration. In some embodiments, the suture 1114 is pulled until no portion of the orthopedic device 1116 remains in the incision 1100 or opening. In other embodiments, the sutures 1114 may be pulled until the orthopedic device 1116 abuts against the portion 1112 of the joint capsule 1102 opposite the incision 1100. The pathway 1118 through which the needle and suture exit the joint 1104 typically, but not always, has a smaller cross-sectional area than the incision 1100 or opening through which joint access is provided. In some embodiments, a trailing suture (not shown) may be coupled to the orthopedic device to permit withdrawal or repositioning of the orthopedic device through the initial incision. The trailing suture, if any, may be coupled to the orthopedic device using the same or different suture lumen or coupling mechanism.

Figure 10K:
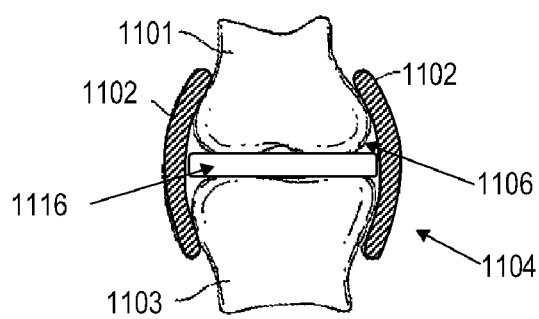
Figure 10L:
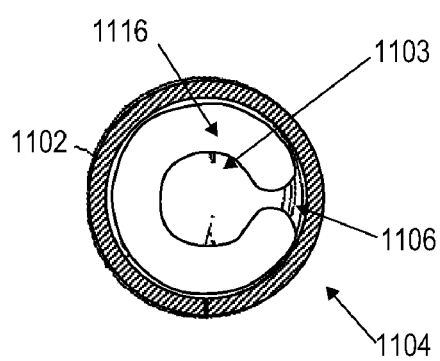
Figure 11:
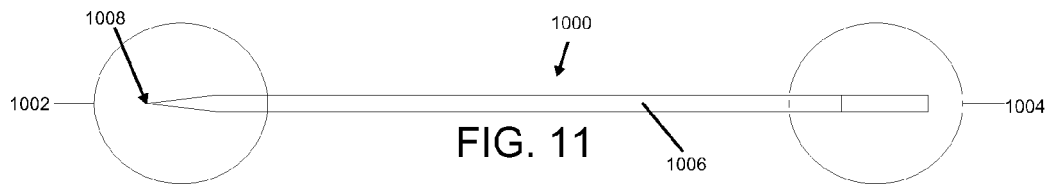
FIG. 11 is a schematic representation of an embodiment of a penetrating member.

As depicted in FIGS. 10G to 10J, once the position of the orthopedic device 1116 is confirmed, the suture 1114 may be cut or manipulated to permit removal of at least a portion of the suture 114 from the patient. In the depicted embodiment, the suture 1114 may be cut using the scalpel 1108 (or other instrument) to permit the loop 1120 of the suture 1114 to be pulled away from the orthopedic device 1116. Once positioning, deployment and functioning of the orthopedic device 1116 is confirmed, the incision 1100 and/or the needle pathway 1118 may be closed. In some embodiments, closure may be performed using sutures, staples and/or adhesives. In some instances where the incision or the needle pathway may be self-sealing and no specific closure procedure is required. FIGS. 10K and 10L depict the orthopedic device 1116 in its final implanted state and the joint capsule closed. The incision may then be dressed, or an optional splint, cast, or other immobilizing or restraining device may be applied to the joint or body region. In some embodiments, the joint space may be filled or infiltrated with one or more therapeutic agents before, during or after the device implantation. As mentioned previously, the therapeutic agents may include but are not limited to an antibiotic, an anti-inflammatory agent, or a viscosupplement (e.g. hylan G-F 20 such as Synvisc®, or various formulations of sodium hyaluronate such as Hyalgan®, Suppartz®, Euflexxa® and Orthovisc®).

In other embodiments, a portion of the suture may be left in the body along with the orthopedic device. For example, the loop of suture may be permanently affixed to the orthopedic device, such that the suture may be cut close are at the skin surface, leaving a portion of the suture attached to the implanted orthopedic device. In some embodiments, tensioning the suture results is transient displacement of the orthopedic device from its base location, and when the exposed portion of the tensioned suture is severed, the unexposed portion is pulled into the body as the orthopedic device retreats back toward its base location.

Although the access procedure described generally above may be applied to any of a variety of joints, in certain embodiments described herein, the orthopedic devices may be sized and configured for implantation in the joints of the hands and wrists. As mentioned elsewhere herein, these joints include the DIP and PIP joints, the MCP joints and the carpo-metacarpal (CMC) joints, as well as the variety of joints between the proximal and distal carpal bones (e.g. scaphoid, lunate, triquetrum, trapezium, trapezoid, capitate, hamate, pisiform), as well as the joints formed between the carpal bones and the radius and ulna. In some embodiments, accessing the joints of the hand and/or wrist may involve making an entry incision on the dorsal side of a joint, such as the CMC joint at the base of a patient's thumb (CMC-1 joint), and using the needle to deliver an orthopedic implant by having the needle exit the CMC-1 joint on the palmar side of the joint. In other embodiments, the entry incision may be made on the palmar side of the joint with the needle exiting the dorsal side. One of skill in the art will understand that one or more needles and other combinations of the entry and exit of the needle are also contemplated, including but not limited to access procedures where the entry and exit of the needle may occur through separate pathways on the same side of a joint (e.g. dorsal/dorsal, or palmar/palmar) or through the medial or lateral side of a joint (e.g. palmar/lateral, palmar/medial, dorsal/lateral, dorsal/medial, lateral/medial, medial/lateral, etc.).

The needle or other penetrating member used to pull the orthopedic device into the joint space may have any of a variety of sizes and configurations. The particular size and configuration may vary and may be based upon the particular joint, the particular access method (e.g. percutaneous vs. cut-down) and other related anatomy (e.g. intra-joint ligaments, extra-capsular ligaments), and/or the type of needle driver (if any), and the size and configuration of the orthopedic device, for example. Other penetrating members may include trocars or rigid wires (e.g. Kirschner wires). In some embodiments, a through lumen may be provided along part or the entire penetrating member.

In some embodiments, other access procedures to the joint may be provided. For example, rather than a stab incision or limited access incision, the skin may be dissected until the joint capsule is exposed, and then a cut is made to form a flap to achieve a larger access opening to the joint. In other embodiments, the exit pathway for the needle and suture may also be created or at least enlarged using a stab incision from a scalpel, or by forming a flap. In another embodiment, a cannula or delivery instrument is inserted through the joint capsule and into the joint space. Various embodiments of delivery instruments that may be used are described in U.S. application Ser. No. 12/099,296, filed Apr. 8, 2008. As depicted in U.S. application Ser. No. 12/099,296, some embodiments of the delivery instrument may comprise a penetrating member that may be used to access a joint without a guidewire or introducer. A small opening in the joint capsule may be formed by the penetration the cannula or delivery instrument, or by the use of a scalpel or trocar, for example.

In some embodiments, instead of using a needle and suture to pull the orthopedic implant into the joint, the orthopedic device (or other type of resilient or shape-memory orthopedic device) may be grasped with fingers or with forceps and inserted into the joint. In some embodiments, the arcuate orthopedic device may be squeezed or restrained to reduce its profile while being inserted into the joint. Once inserted, the restraining force acting on the orthopedic device is relieved to permit reversion to its larger profile. The surgeon can reposition the orthopedic device in the joint to achieve the desired position. The capsule and incision are then closed with a suture and or a dressing (e.g. bandage). In other embodiments, other suture sizes, suture techniques and/or resorbable suture material may be used.

Verification of the position of the various delivery components or the orthopedic device during one or more phases of the implantation procedure may include ultrasound, x-ray imaging, fluoroscopy and MRI. In some instances, verification of the integrity of the joint capsule may be performed to assess the potential for the orthopedic device to migrate or dislodge from the joint.

In another embodiment, the orthopedic device may be inserted in a minimally invasive manner under direct visualization using fluoroscopy, fiberscope or arthroscope. In other embodiments, a limited access procedure using a surgical microscope may also be performed. The insertion of the fiberscope or arthroscope into the joint may be performed percutaneously or by a cut-down procedure as exemplified above, or by other access methods. In some embodiments, the arthroscope may comprise a multi-lumen arthroscope with one or more working channels. The working channels may be used to provide joint irrigation and/or to insert various instruments to smooth the joint surfaces or to cauterize any bleeding that may have occurred, for example.

FIG. 10 depicts one embodiment of a penetrating member 1000, comprising a penetrating section 1002, a suture coupling section 1004 and a body 1006 there between. The length of the penetrating member 1000 may be in the range from about 1 to about 14 cm, sometimes about 2 to about 5 cm, and other times about 2 to about 4 cm. The diameter or transverse dimension of the penetrating member 1000 may be in the range of about 0.5 to about 5 mm or more, sometimes about 1 to about 3 mm, and other times about 1.5 to about 2.5 mm. The penetrating member 1000 in FIG. 10 has a linear-shape penetrating section 1002 and body 1006, but in other embodiments, one or more of the tip, body, or suture coupling section may be may curved or non-linear. In some embodiments, the penetrating member 1000 may comprise a ¼ curve, a ⅜ curve, a ½ curve, a ⅝ curve or a compound curve, for example.

Figure 12A:
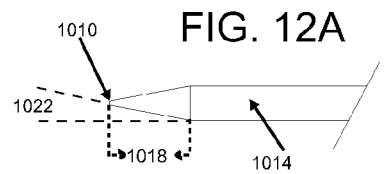
FIGS. 12A and 12B are schematic representations of various embodiments of penetrating sections of penetrating members.
Figure 12B:
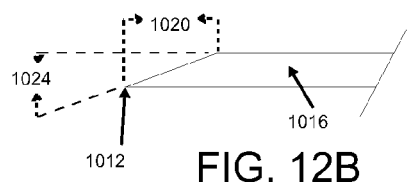

The penetrating section 1002 of the penetrating member 1000 may comprise a sharpened tip 1008 or one or more sharpened edges. The penetrating section 1002 may comprise a tapered tip, a spatula or spade tip, or a triangular cutting tip, for example. In other embodiments, the penetrating member 1000 may have a blunt tip. The sharpened tip 1010, 1012 may be located centrally with respect to the body 1014, as shown in FIG. 12A, or eccentrically with respect to the body 1016, as shown in FIG. 12B. The taper distance 1018, 1020 and/or taper angle 1022, 1024 may vary, and may depend upon the particular penetration characteristics of the joint and/or access procedures, for example.

Figure 13A:
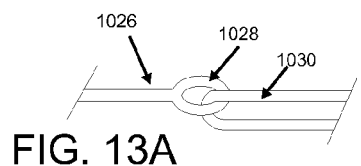
FIGS. 13A to 13C are schematic representations of various embodiments of suture coupling structures of penetrating members.
Figure 13B:
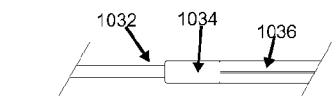
Figure 13C:
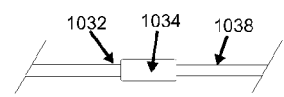

As illustrated in FIGS. 13A to 13C, any of variety of structures or methods may be used to couple a suture to the penetrating member. In FIG. 13A, for example, the suture coupling section 1026 comprises an eyelet 1028 or other aperture structure through which a suture 1030 may be threaded. Although the suture 1030 in FIG. 13A is depicted as being slidably coupled to the eyelet 1026, in other embodiments, one or more suture knots may be used to further secure the suture to the penetrating member. The suture knots used may include but are not limited to square knots, half hitch knots, bowline knots, granny knots or surgical knots. Heat bonding, crimping, soldering and/or an adhesive may also be optionally used to secure the suture to the needle. FIG. 13B depicts another example of a suture coupling section 1032, wherein the suture 1034 is crimped or bonded to a sleeve 1036 of the suture coupling section 1032. The suture 1034 within the sleeve 1036 may comprise a suture loop, or two ends of the same suture, or two or more ends of two or more sutures. FIG. 13C depicts another embodiment wherein a single suture or line 1038 is attached to the sleeve 1036 of the suture coupling section 1032. Although the sleeves 1036 in FIGS. 13B and 13C are closed ended with a single opening into which the sutures 1032, 1038 are inserted, in other embodiments, the sleeves may have one or more other openings. In some embodiments, the sutures may pass and/or be knotted through the additional openings.

Figure 14:
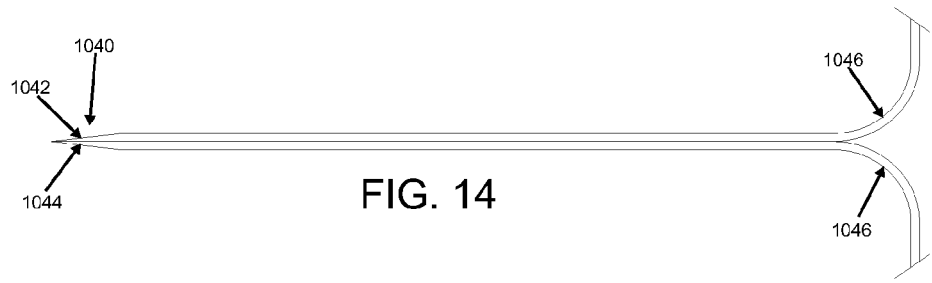
FIG. 14 is a schematic representation of a suture-based penetrating member.

In some embodiments, the suture or elongate member may be integrally formed with the needle or penetrating member. In one example, the penetrating member may comprise a stainless steel needle section which transitions, bifurcates or splits into one or more stainless steel wire sections have a greater flexibility or reduced rigidity than the needle section. In another embodiment, depicted in FIG. 14, the distal section 1040 may comprise the ends 1042 and 1044 of a polymeric or flexible suture 1046, but has been heat treated and/or adhesive bonded together and to stiffen the suture 1046. The distal section 1040 may be shaped to a tapered or beveled tip to function as a needle, or to facilitate insertion of the distal section 1040 into a pre-formed opening or passageway (e.g. by trocar or scalpel). In some embodiments, the polymeric or flexible material may be interwoven or wound about one or more metallic wires or cores to provide stiffening and penetration characteristics. The distal section may also be covered or encapsulated with a sleeve or other type of structure.

The sutures used with various embodiments may have any of a variety of sizes, configurations and materials. The sutures may have a monofilament, a multi-filament or braided configuration. With multi-filament or braided sutures, the individual filaments may have the same or different sizes, configuration and materials. The suture material may comprise one or more absorbable and/or non-absorbable materials, including but not limited plain or chromic catgut, poliglecaprone 25, polyglactin 910, polyglycolic acid, polydioxanone, silk, polyester, stainless steel, polypropylene and polyethylene, for example. The suture diameter may range from about 0.0005 to about 0.04 inches or more (or about size 10-0 to about size 7 per USP suture size standards), but in some embodiments, may be in the range of about 0.04 to about 0.01 inches (or about size 5-0 to about size 2-0), and other times about 0.06 to about 0.08 inches (or about size 4-0 to about size 3-0). Although the suture or pull member may have a generally circular cross-sectional shape, other suture shapes are also contemplated, including but not limited to flat or ribbon-type sutures. In still other embodiments, a suture may be attached to a separately formed sling section. In other embodiments, other flexible elongate structures may be used, including but not limited to chain structures. The suture or other flexible elongate structure may be coated with one or more substances, including but not limited to anti-infective agents (e.g. triclosan) and frictional or anti-frictional agents (e.g. collagen or PTFE, respectively).

In some embodiments, one or more portions of the suture 1400 may be debraided or loosened to form a sling 1402 or other increased surface area section, as depicted in FIG. 14A. As depicted in FIG. 14B, the sling 1402 of the suture 1400 may facilitate the pulling of an orthopedic device 1404 by providing a more stable coupling through an increased surface area and wider force distribution. The sling 1402 may also reduce the potential for damaging the surface of the orthopedic device 1404 from being sliced or cut by a narrower suture line. The coupling of the suture 1046 and the orthopedic device 1404 by wrapping or looping the suture 1400 around a portion of the orthopedic device 1404, and other mechanisms for coupling the suture and orthopedic device, are described in greater detail below.

Figure 15:
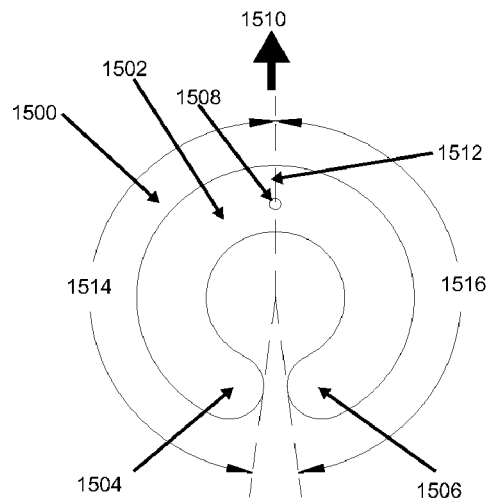
FIG. 15 is a superior elevational view of an embodiment of an orthopedic device.

FIG. 15 depicts one embodiment of an orthopedic device 1500, comprising an arcuate, "C"-shape body 1502 located between two ends 1504 and 1506. A suture coupling structure, comprising an aperture or lumen 1508 through which a suture may be inserted, is provided through the body 1502. In this particular embodiment, the lumen 1508 comprises a lumen axis that is transverse to the plane of the "C"-shaped body 1502. In other embodiments, the suture lumen may have any of a variety of orientations, and may lie within the plane of the "C"-shape body 1502, either aligned with the pull axis 1510, transverse to the pull axis 1510, or any angle there between. The suture lumen may also be oriented in a skewed configuration with respect to the plane of the "C"-shape body 1502. The suture lumen may also have any of a variety of configurations, including but not limited to a linear configuration, a curved configuration, an angled configuration, a branching configuration with multiple suture passageways, or any combination thereof. Also, the suture lumen 1502 of the orthopedic device 1500 in FIG. 15 is provided at a midline 1512 of the body 1502, but in other embodiments, the suture lumen 1508 may be offset from the midline 1512. As shown in FIG. 15, the ends 1504 and 1506 of the orthopedic device 1500 are symmetrically configured with angular dimensions 1514 and 1516 of about 175 degrees from the suture lumen 1502, but in other embodiments, the ends 1504 and 1506 may each be configured anywhere from about 0 degrees to about 180 degrees (or more for spiral or other overlapping configurations). For example, with respect to a suture lumen or other reference point on the orthopedic device, each end may be configured about ±5, about ±10, about ±15, about ±30, about ±45, about ±60, about ±75, about ±90, about ±105, about ±120, about ±135, about ±150, about ±165, about ±180, about ±185, about ±195, about ±210, about ±225, about ±240, about ±255, or about ±270 degrees or more from the suture lumen or reference point. In some embodiments, the ends 1504 and 1506 may be asymmetrical or otherwise configured differently. In some embodiments, more than one suture lumen may be provided, and the configurations of the suture lumens may be the same or different.

Figure 16A:
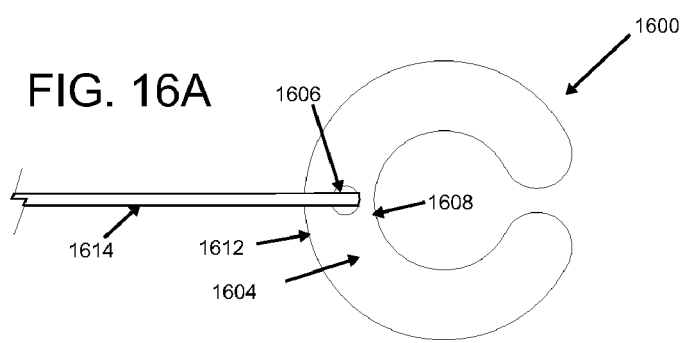
FIGS. 16A and 16B are schematic superior elevational and side cross-sectional views of another embodiment of an orthopedic device.
Figure 16B:
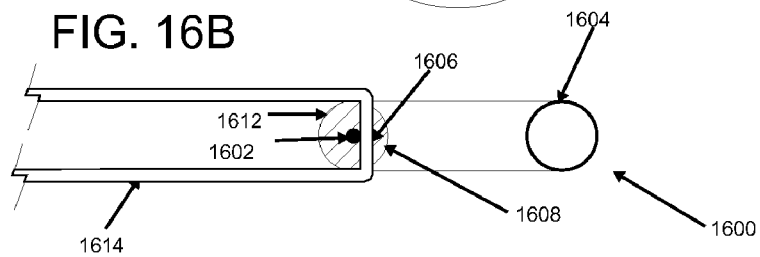
Figure 16C:
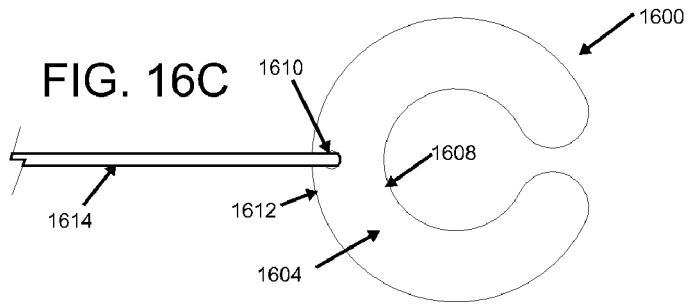
FIGS. 16C and 16D are schematic superior elevational and side cross-sectional views of another embodiment of an orthopedic device.
Figure 16D:
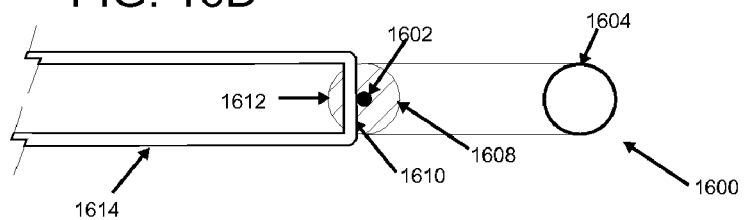

Referring to FIGS. 16A and 16B, in embodiments of the orthopedic device 1600 comprising a core component 1602 and an articular component 1604, the suture lumen 1606 may be located along the lesser curvature 1608 of the orthopedic device 1600 with respect to the core component 1602. In some embodiments, a suture lumen 1606 on the lesser curvature 1608 may facilitate the pulling of the orthopedic device 1600 into a joint or joint capsule by pulling on the more rigid core component 1602 which supports the articular component 1604. This configuration of the suture lumen 1606 may also reduce the potential damage to the articular component 1604 during pulling, by acting directly on the core component 1602 rather than the articular component 1604. In other embodiments, as depicted in FIGS. 16C and 16D, the suture lumen 1610 may be located along the greater curvature 1612 of the orthopedic device 1600 with respect to the core component 1602. Depending upon the particular material and its structure, in some embodiments the articular component 1604 may be stretched or deformed as the suture 1614 is pulling on the orthopedic device 1600. In still other embodiments, the suture lumen may pass above or below the core component on cross-sectional view.

The suture 1614 may be pre-threaded through the suture lumen 1606 and 1610 of the orthopedic device 1600 at the point-of-manufacture, or may be threaded at the point-of-use. The suture may also be pre-threaded or pre-attached to the needle, or may be separate from the needle. In some embodiments, the suture 1614 may be slidably threaded through the suture lumen 1606 and 1610, or may be non-slidable due to surface resistance, heat bonding, adhesives and other processes, for example. A needle threader or other type of loop or threading tool may be provided alone or in kit with the suture and/or orthopedic device to facilitate threading. In embodiments comprising a suture lumen, the suture lumen may be preformed or may be formed by a needle or other penetrating device used to pass the suture through the articular layer.

Figure 17A:
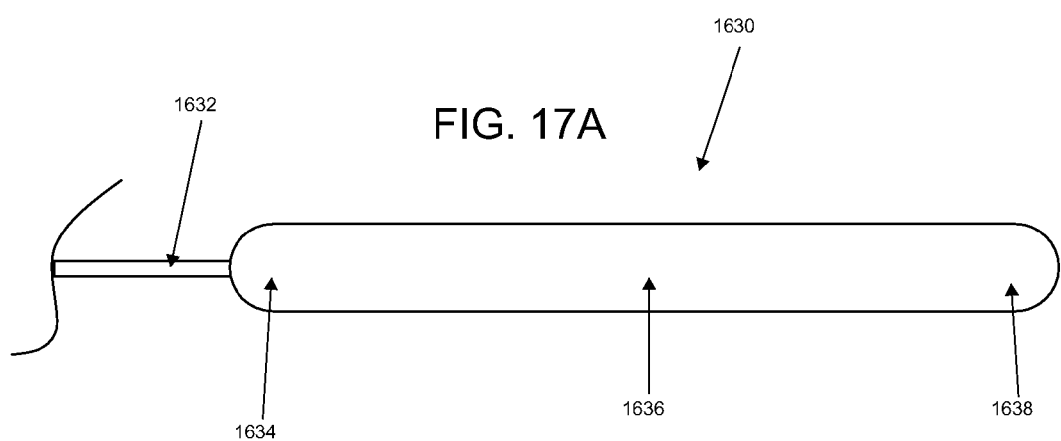
FIGS. 17A and 17B are schematic superior elevational and side cross-sectional views of another embodiment of an orthopedic device.
Figure 17B:
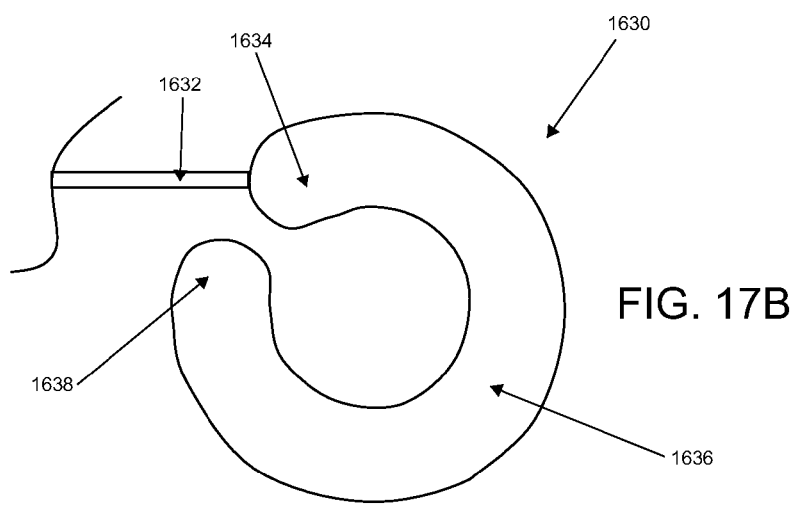

FIGS. 17A and 17B depict another embodiment of an orthopedic device 1630 with an integrally formed suture 1632 or pull member positioned at a first end 1634 of the orthopedic device 1630. In other embodiments, the suture or pull member may comprise a suture loop coupled to a suture lumen located at an end of the device. The orthopedic device 1630 may be pulled into a joint space using the suture 1632 such that the delivery profile of the device 1630 into the joint is similar to the axial cross-sectional area of the device 1630. For example, once the suture 1632 is passed through the joint and tensioned, the first end 1634 of the device 1630 is pulled into the joint, followed by the body 1636 and then the second end 1638. As the device 1630 is pulled into the joint, the device 1630 may assume a straight or straighter configuration, but as a larger proportion of the device 1630 is pulled in, the bias or resilience of the device 1630 may assume a more bent configuration, as depicted in FIG. 17B. Once positioned in the joint, all or at least a portion of the exposed suture 1643 may be separated or cut from the orthopedic device 1630.

Figure 18A:
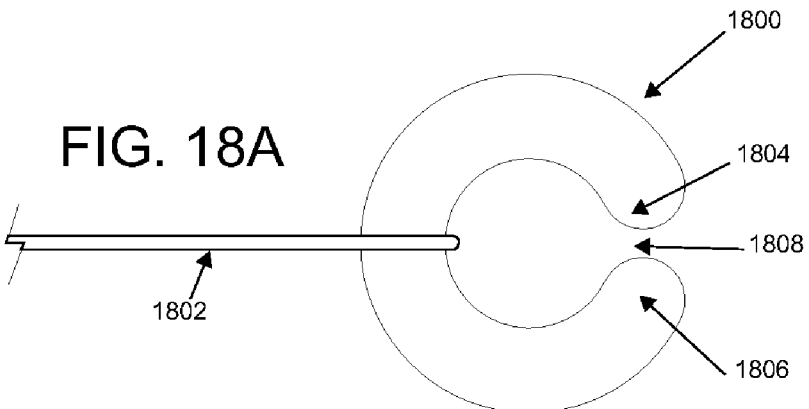
FIGS. 18A and 18B are schematic superior elevational and side cross-sectional views of another embodiment of an orthopedic device.
Figure 18B:
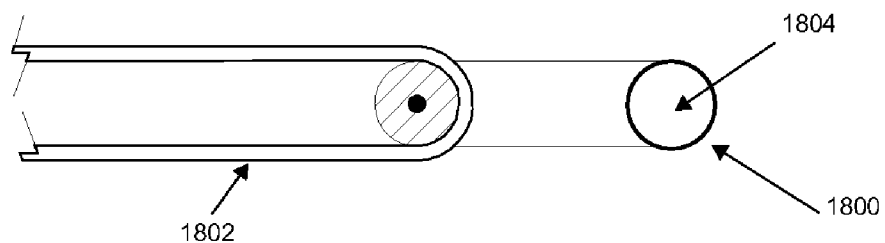
Figure 18C:
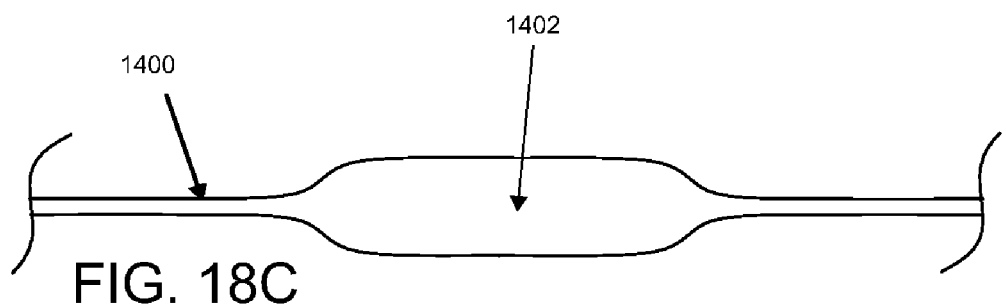
FIG. 18C is a schematic representation of a suture-based sling.
Figure 18D:
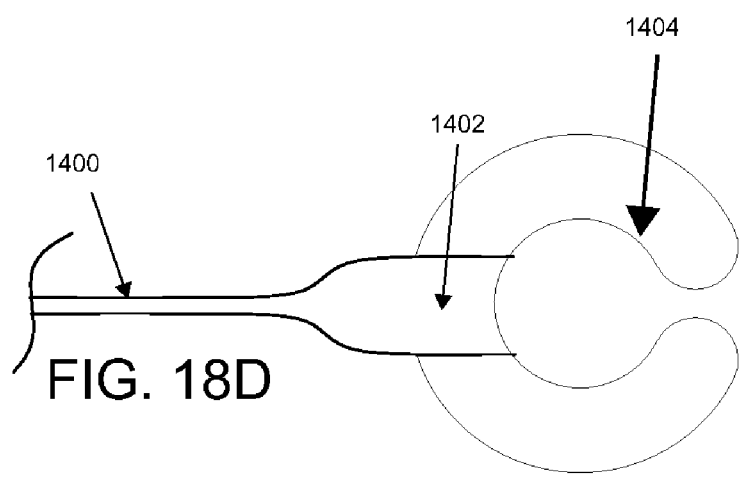
FIG. 18D depicts the sling of FIG. 18C looped around an orthopedic device.

As shown in FIGS. 18A and 18B, in some embodiments of the orthopedic device 1800, no suture lumen or other suture coupling structure is provided. Instead, a loop of suture 1802 is looped around a portion of the orthopedic device 1800 to pull the orthopedic device into the joint. It is understood that this delivery method may also be utilized with orthopedic devices having suture lumens. Although a single loop is depicted in FIGS. 18A and 18B, and two or more loops may be made around the body of the orthopedic device 1800. In some embodiments, the suture 1802 is looped away from either end 1804 and 1806 of the orthopedic device 1800, but not necessarily about a midline of the body or symmetrically between the two ends 1804 and 1806. After the orthopedic device 1800 is pulled into position, one end (not shown) of the suture 1802 may be released and the suture may be pulled off or away from the orthopedic device 1800. In some embodiments, the suture may also be knotted or tied to the orthopedic device 1800, and a portion of the suture may remain attached to the orthopedic device 1800 following implantation. In other embodiments, the suture may be separated from the orthopedic device by passing the suture 1802 out of the gap 1808 between the two ends 1804 and 1806. In other embodiments, a tether (not shown) may be provided across the two ends 1804 and 1806 to resist inadvertent passage of the suture 1802 through the gap 1808. The tether may be provided with a laxity or redundant length, which may permit additional separation of the two ends 1804 and 1806, in addition to permitting the two ends 1804 and 1806 to come closer together or overlap. In still other embodiments, the length of the tether may be configured to control the degree of separation, overlap or crossing between the two ends 1804 and 1806, and in some embodiments, may even be tensioned or taut in its native configuration. The tether may comprise an elastic or inelastic material or structure. Multiple tethers or bridge structures may be provided across the gap, if any, of the orthopedic device.

Figure 19A:
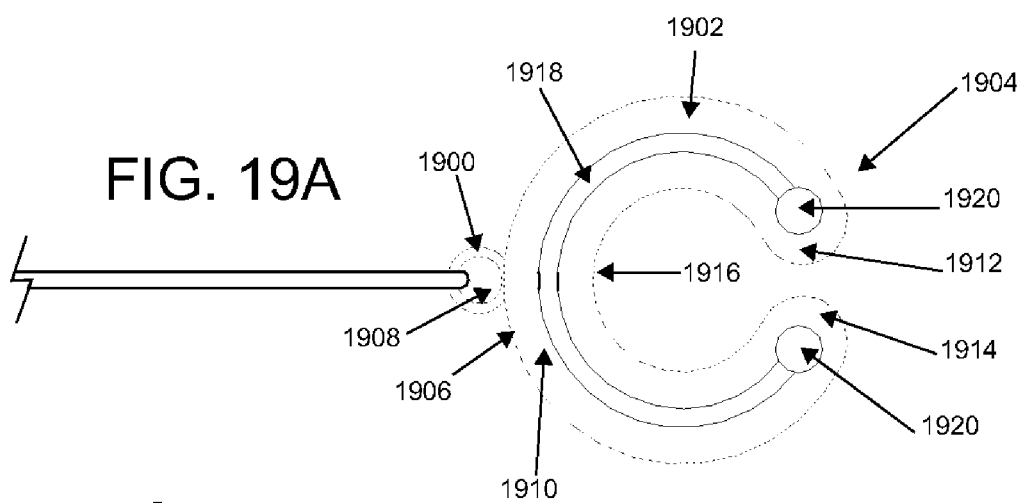
FIGS. 19A and 19B are schematic superior elevational and side cross-sectional views of another embodiment of an orthopedic device.
Figure 19B:
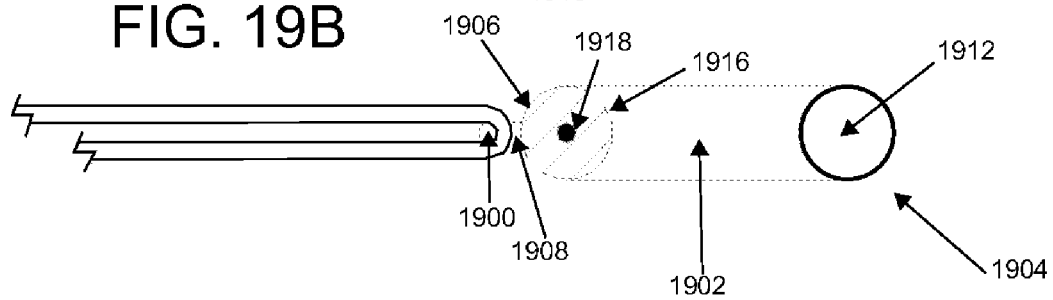

In another embodiment, a suture coupling structure 1900 may extend or otherwise be located external to the outer surface of the articular layer 1902 of the orthopedic device 1904. In FIGS. 19A and 19B, for example, the suture coupling structure comprises an eyelet 1900 located about the greater curvature 1906 of the orthopedic device 1904. As shown, the aperture 1908 of the eyelet 1900 has a through axis that is transverse to the plane of the "C"-shape orthopedic device 1904, but in other embodiments, any other orientation may be used. Although eyelet 1900 has a general circular configurations, other configurations are also contemplated, including but not limited oval, square, triangular or other polygonal or curvilinear shapes. The cross-sectional shape of the aperture may or may not have a similar general shape as the suture coupling structure. In other embodiments, the suture coupling structure may comprise a flange, T-bar, hook or other coupling structure. In some further embodiments, the suture coupling structure may be partially or completely recessed with respect to the outer surface of the articular layer. The suture coupling structure may comprise any of a variety of materials, including but not limited to a metal, plastic, or combination thereof. The material may be the same or different from one or more other components of the orthopedic device. As noted in FIG. 19A, the eyelet 1900 is generally located along the midline that generally splits the orthopedic device body 1910 and/or orthopedic device ends 1912 and 1914 in half, but in other embodiments, may be located on an end 1912 and 1914 of the orthopedic device 1904 or anywhere there between. For example, the eyelet 1900 may be located approximately at the 180 degree position as depicted in FIG. 19A, but may have other locations depending upon the particular orthopedic device configuration, including but not limited to about the 0, 15, 30, 45, 60, 75, 90, 105, 120, 135, 150, 165, 195, 210, 225, 240, 255, 270, 285, 300, 315, 330, and 345 degree positions on a superior elevational view of the orthopedic device. As noted in FIG. 19B, the circumferential location of the eyelet 1900 may be located midway between the upper and lower portions of the orthopedic device along the greater curvature 1906 at the 180 degree position, but in other embodiments may be located on the lesser curvature 1916 or anywhere between the greater curvature 1906 and the lesser curvature 1916, including but not limited to about the 0, 15, 30, 45, 60, 75, 90, 105, 120, 135, 150, 165, 195, 210, 225, 240, 255, 270, 285, 300, 315, 330, and 345 degree positions on an axial cross-sectional view. The eyelet 1900 may also have a general orientation that is perpendicular (i.e. 90 degrees) to the outer surface of the articular layer, but in some embodiments, the angle may be anywhere from about −45 to about +135 degrees, including but not limited to −30, −15, 0, +15, +30, +45, +60, +75, +105, and +120 degrees. The eyelet 1900 of FIG. 19A is shown in a generally flush position with respect to the outer surface of the articular layer, in other embodiments, the eyelet 1900 may have a flexible or rigid stem, stalk or tether with a length of about to about 5 mm or more, and sometimes about 2 to about 4 mm, or more. As illustrated in FIG. 19A, the orthopedic device 1904 further comprises a core component 1918 with enlarged or bulbous ends 1920. In some embodiments, the enlarged ends 1920 of the core component 1918 may reduce the risk that the ends 1920 make poke or protrude from the articular layer. The eyelet 1900 may be attached to the articular layer 1902 and/or the core component 1918, and at least a portion of the eyelet aperture, if not all of the eyelet aperture, may be external to the articular layer. In other embodiments, as described below, the eyelet aperture may be embedded within the articular layer.

Figure 19C:
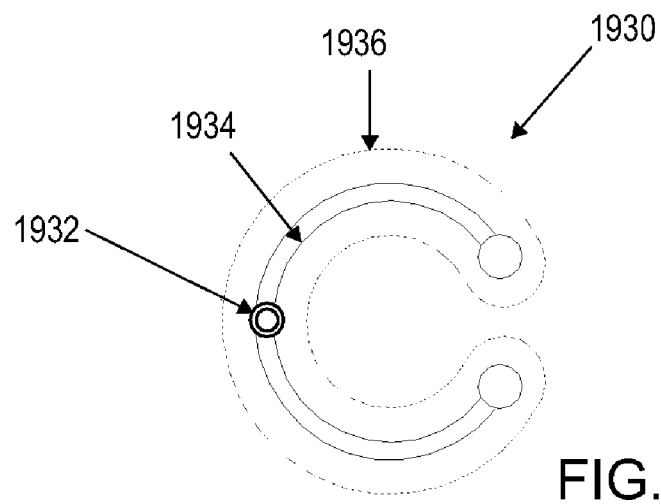
FIGS. 19C to 19E are schematic superior elevational views of other embodiments of orthopedic devices.
Figure 19D:
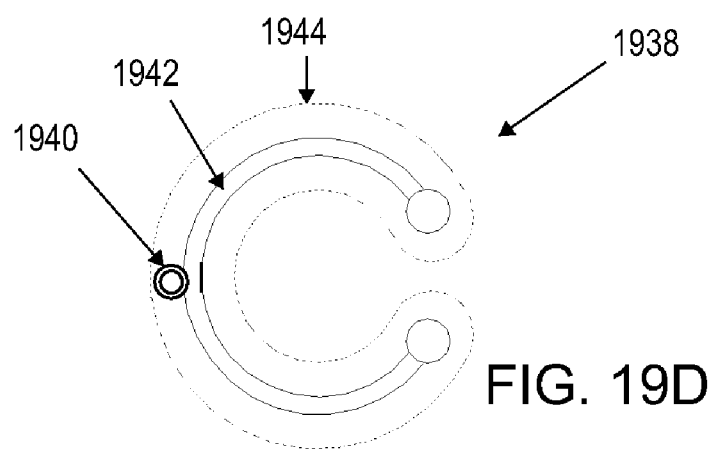
Figure 19E:
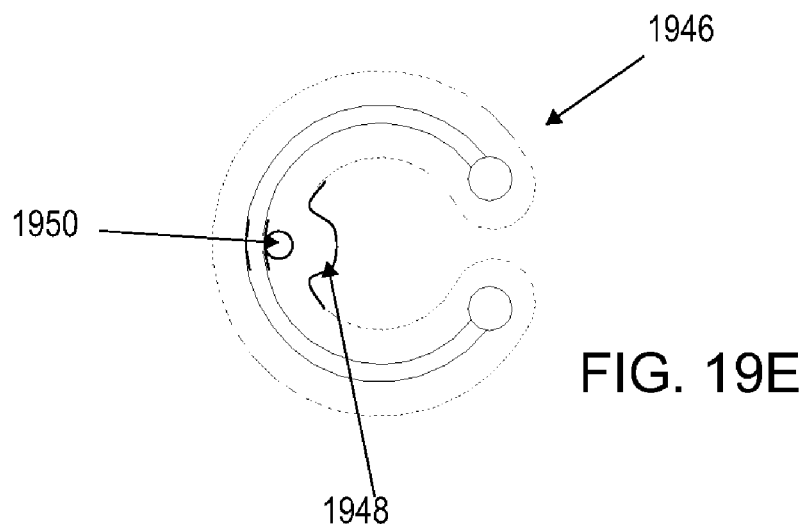

FIG. 19C depicts another embodiment of an orthopedic device 1930, comprising an eyelet 1932 located inline along the length of the core member 1934. An inline eyelet may or may not be covered by the articular layer 1936 of the orthopedic device 1930. FIG. 19D depicts another embodiment of an orthopedic device 1938, comprising an eyelet 1940 offset from the core member 1942 and covered by the articular layer 1944. In this embodiment, the articular layer 1944 maintains its general surface curvature about the eyelet 1940, but in other embodiments, the region of the articular layer overlying the eyelet may be thicker or thinner along the superior, inferior, outer, and/or inner eyelet surface. The eyelet 1940 in FIG. 19D is generally located midway about the greater curvature of the orthopedic device 1938, but in other embodiments, may be located anywhere along the length of the orthopedic device, including the lesser curvature or closer to one of the ends of the orthopedic device. In still other embodiments, such as the embodiment illustrated in FIG. 19E, the orthopedic device 1946 may lack an eyelet or other reinforcement structure, but the articular layer 1948 about the suture opening 1950 may have one or more increased dimensions to resist rupture of the articular layer 1948 by the suture or pull member during implantation. In some of the embodiments, the eyelet may be formed by twisting a loop from the core member.

In some embodiments, the suture may comprise a complementary interfit structure that releasably locks with the coupling structure. For example, the suture may comprise a hook or a latch that may be releasably attached to an eyelet coupling structure of the orthopedic device. Also, in some embodiments, the suture coupling structure may be configured with a pre-selected location with respect to the orthopedic device, but in other embodiments, the location may be user-selected. For example, the suture coupling structure may comprise a slidable eyelet that may be repositioned with respect to the orthopedic device, or a suture coupling structure that may be attached to the orthopedic device at the point-of-use by one or more barbs, books, clamps and the like. The suture coupling structure may be configured to attach to the articular component and/or the core component of the orthopedic device. In some embodiments, more than one suture coupling structure may be provided.

Figure 20A:
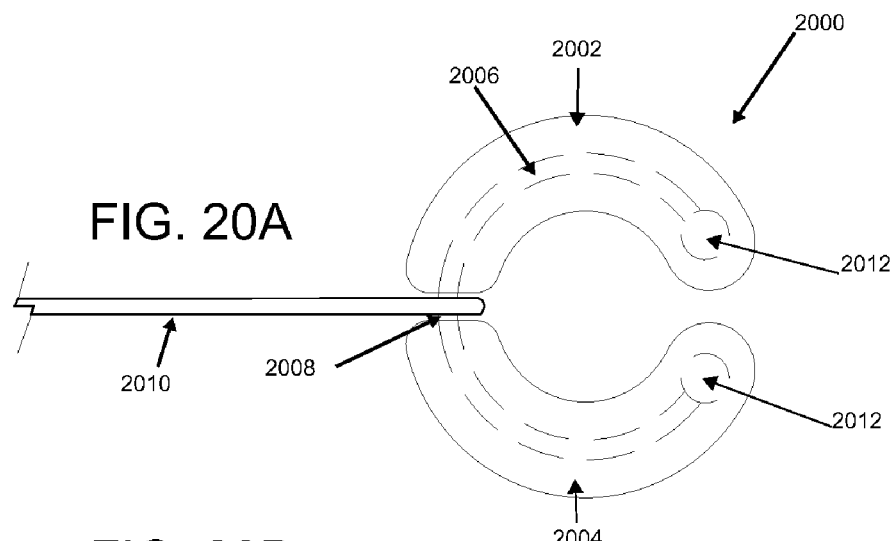
FIGS. 20A and 20B are schematic superior elevational and side cross-sectional views of another embodiment of an orthopedic device.
Figure 20B:
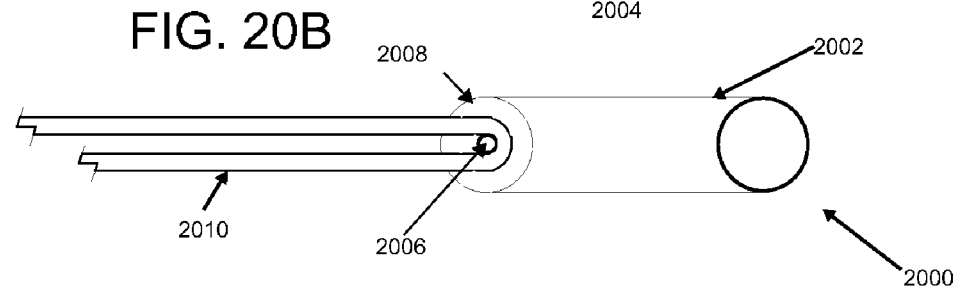

As described for the embodiment illustrated in FIG. 16B, the suture lumen 1606 may be located so that the suture 1614 can contact and potentially act directly on the core 1602. As shown in FIG. 16B, however, when the pulling force from manipulating the suture 1614 is applied, portions of the articular layer 1604 may still experience high stresses where the suture 1516 exits the suture lumen 1606 at its lumen openings 1616 and 1618. In contrast, FIGS. 20A and 20B depicts an embodiment of an orthopedic device 2000 comprises a segmented articular layer 2002 and 2004 with a core component 2006 having an exposed region 2008 where a suture 2010 may be looped around the core component 2006 without necessarily exerting any force on any portion of the articular layer 2002 or 2004. In some embodiments, the exposed region 2008 of the core component 2006 may have a different surface treatment or coating than the other portions that are covered by the articular layer.

Figure 21A:
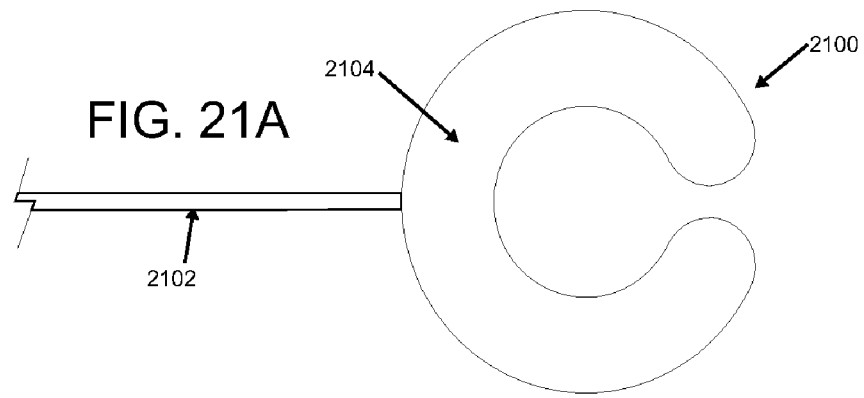
FIGS. 21A and 21B are schematic superior elevational and side cross-sectional views of another embodiment of an orthopedic device.
Figure 21B:
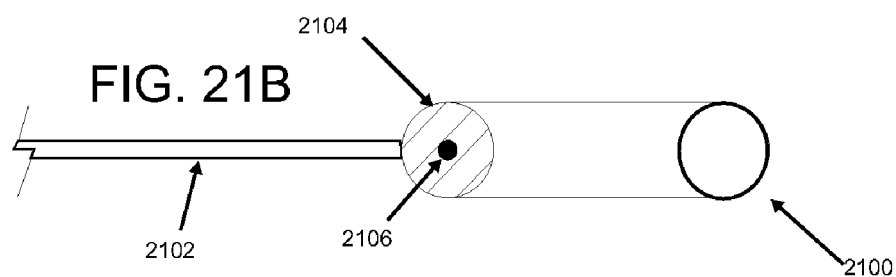

FIGS. 21A and 21B depict another embodiment of an orthopedic device 2100, comprising a suture or tether 2102 that has been integrally formed with the orthopedic device 2100. The tether 2100 may be bonded to the surface and/or the internal structure of the articular layer 2104, and/or optionally bonded or formed with the core component 2106 of the prosthesis 2100. In some embodiments, the tether 2102 may be heat bonded or glued to the orthopedic device, embedded within the orthopedic device, and/or extruded from the orthopedic device (e.g. wherein the tether 2102 comprises a flowable material that is similar to the material comprising the articular layer 2104 or core component 2106).

Figure 22A:
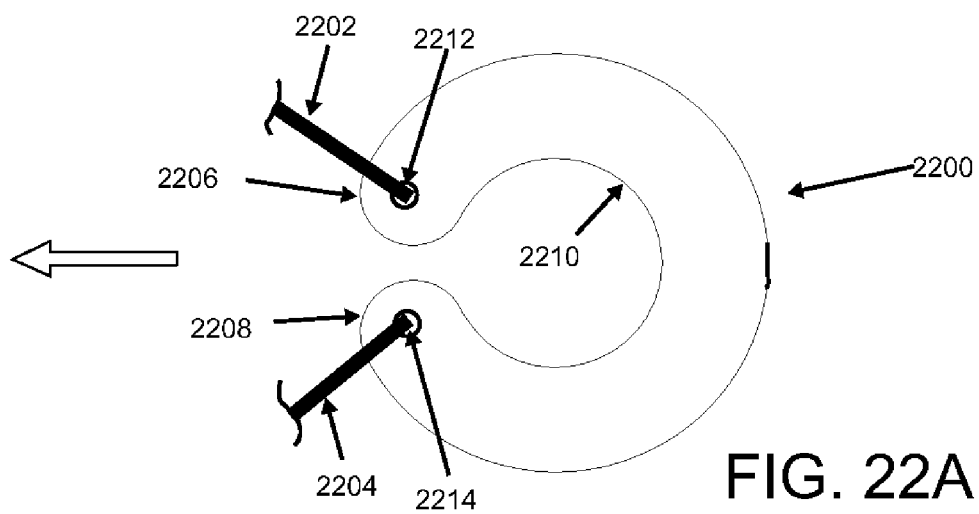
FIGS. 22A and 22B depict various embodiments of an orthopedic device with multiple sutures.

Although several embodiments described herein may comprise or may be implanted using a single needle or suture, in some embodiments, two or more sutures and/or needles may be used to implant the orthopedic device. In FIG. 22A, for example, the orthopedic device 2200 may be attached to two sutures 2202 and 2204 during the implantation procedure. The two sutures 2202 and 2204 may be attached or threaded to the same needle or to different needles. In some embodiments, the use of two sutures may facilitate the implantation of an orthopedic device that is implanted in an alternate fashion, e.g. where the ends 2206 and 2208 of the orthopedic device 2200 are inserted into the joint space first, or where the inner curvature 2210 of the orthopedic device will be looped around an intra-articular structure (e.g. the anterior or posterior cruciate ligament of a knee joint), and the ends 2206 and 2208 of the orthopedic device 2200 are spread apart. Although the suture lumens 2212 and 2214 of the orthopedic device 2200 are symmetrically located on each end 2206 and 2208 of the orthopedic device 2200, each suture lumen 2212 and 2214, may be located any where along the length of the orthopedic device and the configurations each suture lumen may be the same or different. In some examples, orthopedic devices attached to multiple sutures, such as the sutures 2202 and 2204 attached to the orthopedic device 2200, may also be cinched and/or tied together to adjust the configuration of the orthopedic device and/or to form a closed-loop device. In still other embodiments, one or more sutures may be integrally formed with the orthopedic device, rather than being looped through a suture lumen or looped around the body of the orthopedic device.

Figure 22B:
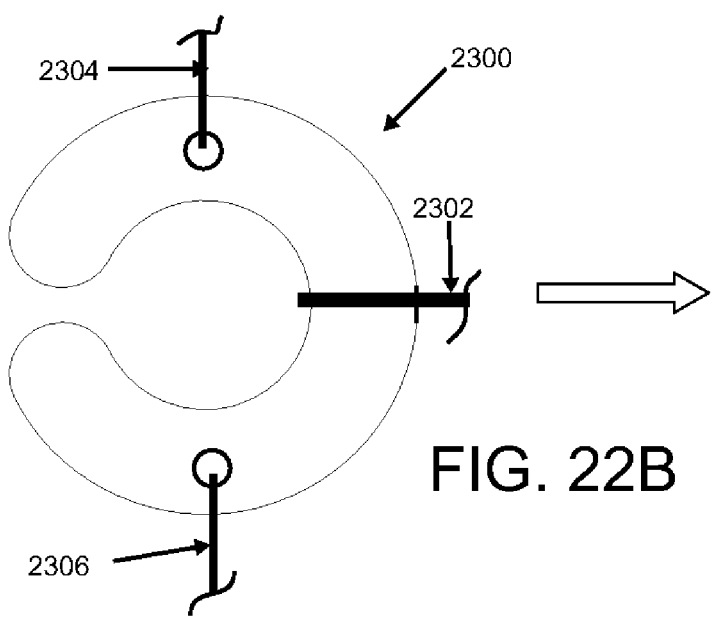

In some embodiments, different suture types may be used during an implantation procedure. For example, in FIG. 22B the orthopedic device 2300 is attached to three sutures 2302, 2304 and 2306, wherein one suture 2302 is larger than the other sutures 2304 and 2306. In the illustrated embodiment, the larger sutures 2302 may be used to pull the orthopedic device, for example, through a percutaneous pathway, through one or more joint capsules, and sometimes even through one or more ligaments or other connective tissue structure about the affected joint. The larger suture 2302 may tolerate higher pulling forces than one or more of the other sutures 2304 and 2306. In some embodiments, the other sutures 2304 and 2306 may be to reorient the orthopedic device 2300 to its desired position and need not have a greater thickness.

Figure 23A:
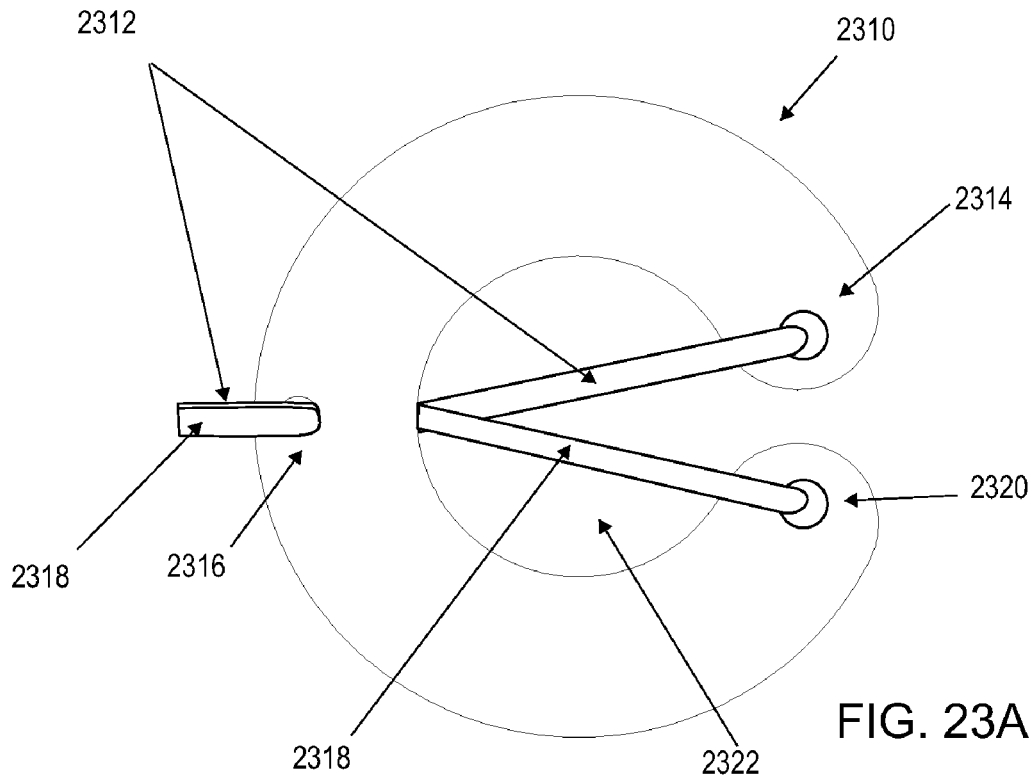
FIGS. 23A and 23B depicts another embodiment of a user-adjustable orthopedic device with multiple sutures, before and after adjustment.
Figure 23B:
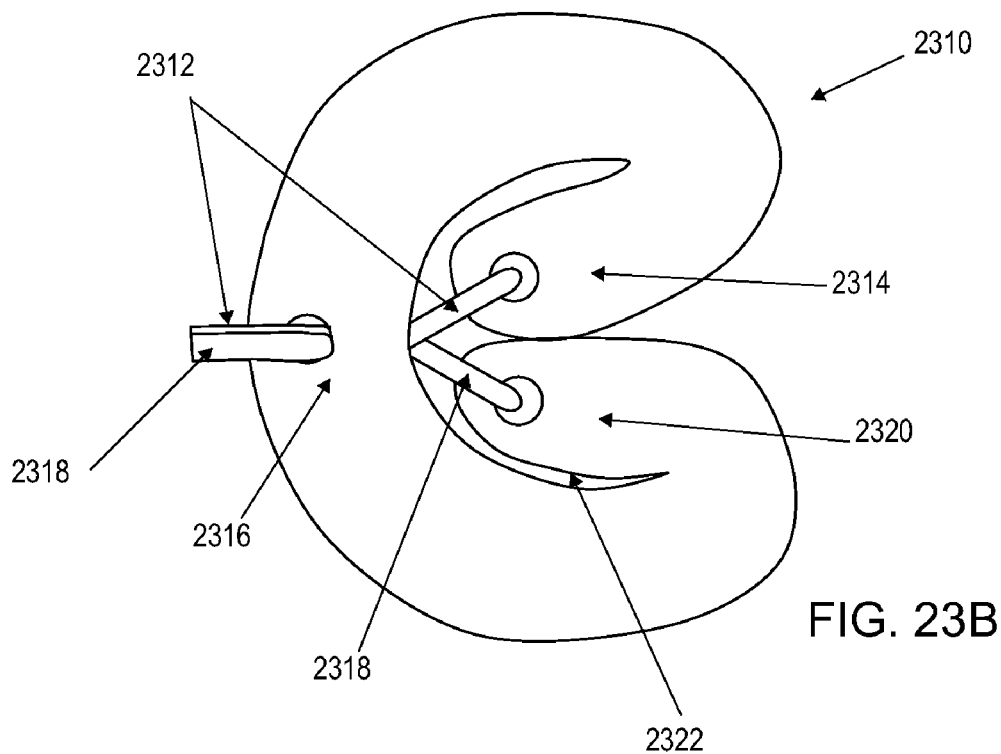

FIG. 23A illustrates another embodiment of an orthopedic device 2310 with at least one suture or pull member 2312 coupled to a first distal region 2314 of the orthopedic device 2310, wherein the pull member 2312 is further slidably or movable coupled to a first proximal region 2316 of the orthopedic device 2310. In this particular embodiment, the pull member 2312 may be used to adjust the relative position of the first distal region 2314 (e.g. end region) with respect to the first proximal region 2316 (e.g. midline region). As shown in FIG. 23A, multiple discrete pull members 2312 and 2318 may be provided, and each may be attached to different distal regions 2314 and 2320, or a branched or interconnected pull member may be provided. Discrete multiple pull members 2312 and 2318 may permit independent adjustment or manipulation of the distal regions 2314 and 2320. The pull members 2312 and 2318 may be coupled to the same proximal region 2316 or to different proximal regions. The distal regions 2314 and 2320 in FIG. 23B are depicted as being folded inward into the central opening 2322 of the orthopedic device 2310, but in other embodiments, the pull members 2312 and 2318 may be manipulated to a lesser degree, e.g. to adjust the relative gap spacing between the regions 2314 and 2320 without infolding into the central opening 2322. Although not depicted in FIGS. 23A and 23B, the orthopedic device 2310 may further comprise a third pull member looped or coupled to the first proximal region 2316, which may be used to pull on the orthopedic device 2310 without pulling on the distal regions 2314 and 2320.

Figure 23C:
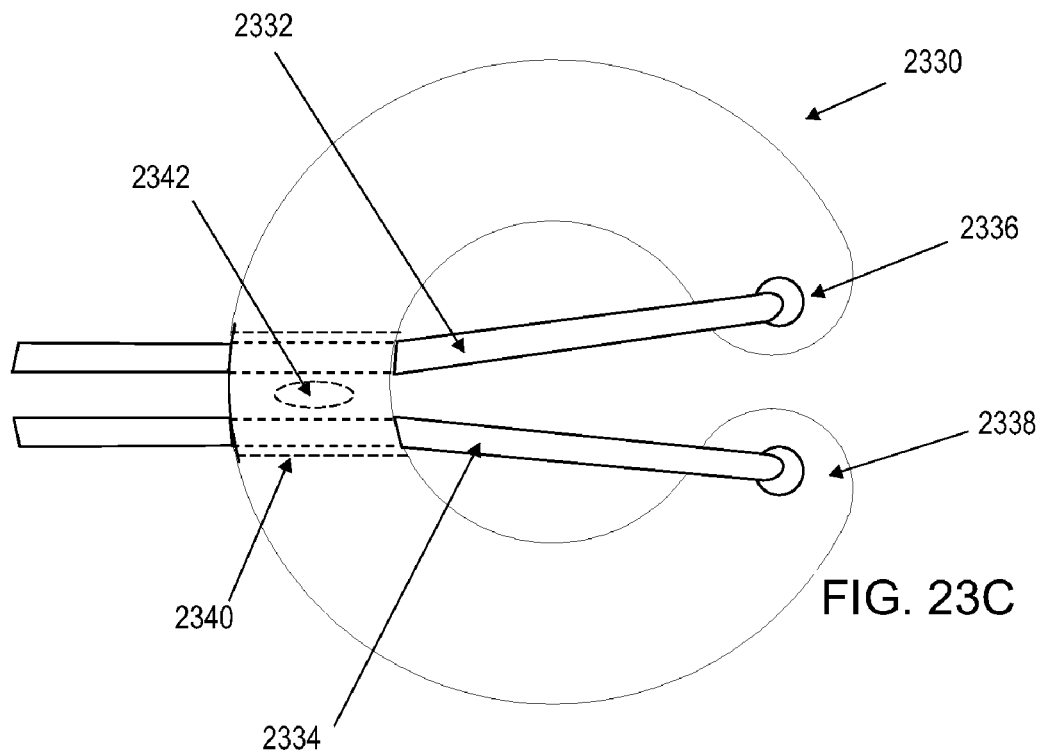
FIGS. 23C and 23D depict another embodiment of a user-adjustable orthopedic device, before and after suture fixation.
Figure 23D:
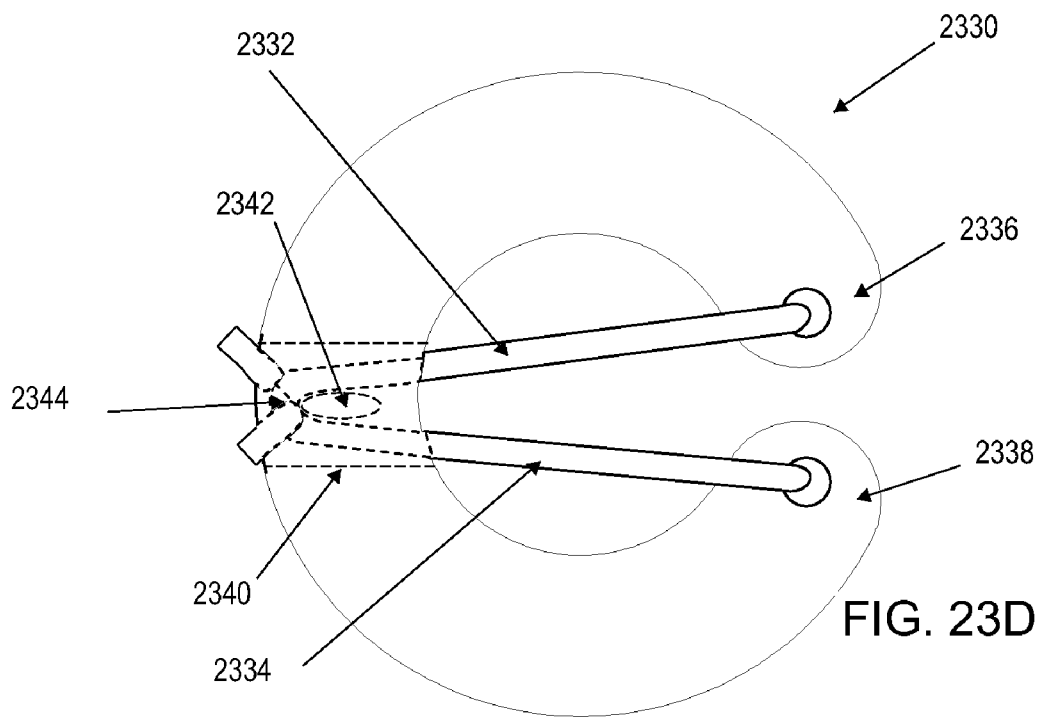

In some embodiments, orthopedic devices with multiple pull members may be used, for example, to restrict the range of configurational change of the orthopedic device. In FIGS. 23C and 23D, for example, the orthopedic device 2330 may comprise pull members 2332 and 2334 attached to distal regions 2336 and 2338 passing through one or more proximal regions 2340. Rather than separating or severing the pull members 2332 and 2334 from the distal regions 2336 and 2338, once the orthopedic device 2330 is positioned, one or more pull members 2332 and 2334 may be attached to each other or further attached to the orthopedic device 2330 to limit or restrict separation of distal regions 2336 and 2338 from the proximal region(s) 2340. In FIG. 23D, for example, the proximal region 2340 comprises a post 2342 or other interference structure. When the pull members 2332 and 2334 are fixedly coupled to each other (e.g. with knot 2344 or other coupling procedure or mechanism), the post 2342 restricts or limits the distance by which the distal regions 2336 and 2338 may separate from the proximal region 2340. In this specific embodiment, some relative sliding the knotted pull members 2332 and 2334 may occur with respect to the post 2342, which may permit some separation of the distal regions 2336 and 2338, but in other embodiments, the pull members 2332 and 2334 may be directly knotted to the post 2342 or interference structure to restrict or limit sliding or other movement of the pull members 2332 and 2334.

Figure 23E:
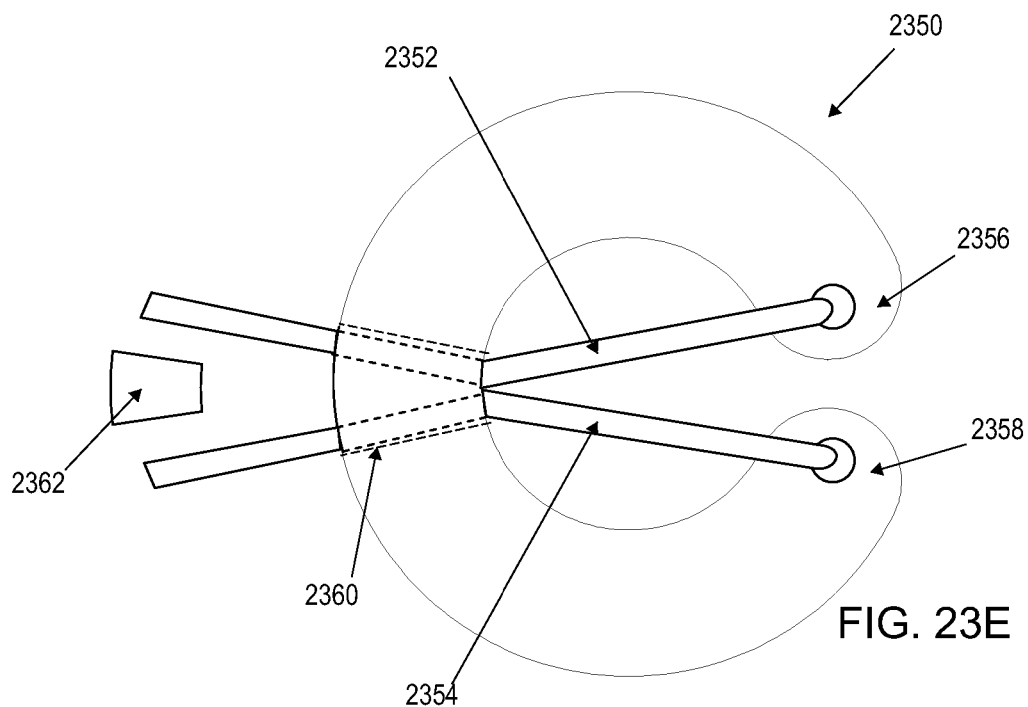
FIGS. 23E and 23F depict another embodiment of a user-adjustable orthopedic device, before and after locking.
Figure 23F:
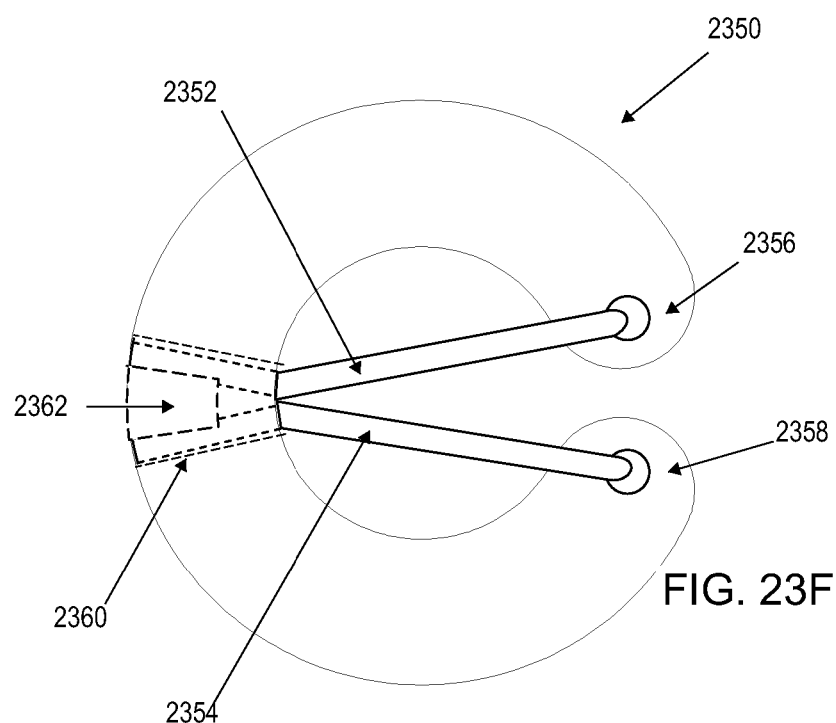

FIGS. 23E and 23F depict another embodiment of an orthopedic device 2350 comprising multiple pull members 2352 and 2354 distally coupled to multiple distal regions 2356 and 2358 and proximally passing through a proximal region 2360. An interference member 2362 may be positioned with respect to the proximal region 2360 to restrict sliding or movement of the pull members 2352 and 2354. In the particular embodiment depicted in FIGS. 23E and 23F, the interference member 2362 comprises a plug structure which may be configured to form a friction and/or mechanical interfit with the through opening of the proximal region 2360 and/or the pull members 2352 and 2354. In other embodiments, the interference member 2362 may comprise a clip, clamp, or crimp member, for example.

Figure 24:
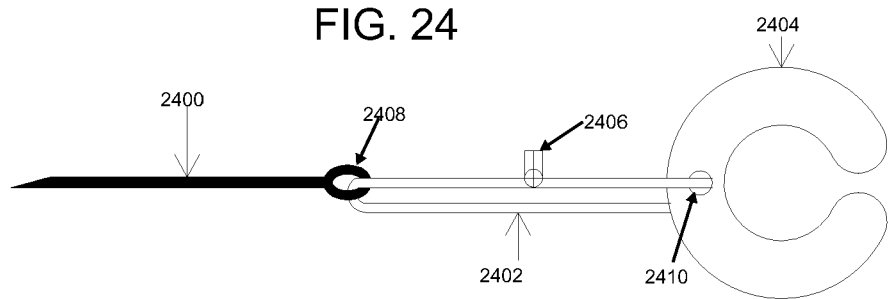
FIG. 24 depicts one embodiment of an orthopedic device coupled to a needle using a suture.

As previously described, in some embodiments, the needle used to insert the suture through the joint capsule and joint space may be manipulated manually by hand or with a pair of needle forceps. In some embodiments, longer and larger needles may be used when manipulating by hand, and/or when the orthopedic device implantation procedure is performed percutaneously through thicker dermal and connective tissue layers. In other embodiments, however, shorter needles may be used. FIG. 24, for example, depicts one embodiment of a short needle 2400 connected to a short suture loop 2402 that is looped through a small orthopedic device 2404 that is configured for a DIP, PIP, MP or CMC joint. These joints of the hand and wrist may involve minimal skin and underlying connective tissue penetration during percutaneous access, even in obese patients. Although the suture knot 2406 of the suture loop 2402 is schematically depicted between the needle eyelet 2408 and the suture lumen 2410 of the orthopedic device 2404, in practice, the knot 2406 may be positioned at or adjacent to the needle eyelet 2408, or buried within the suture lumen 2410.

Figure 25A:
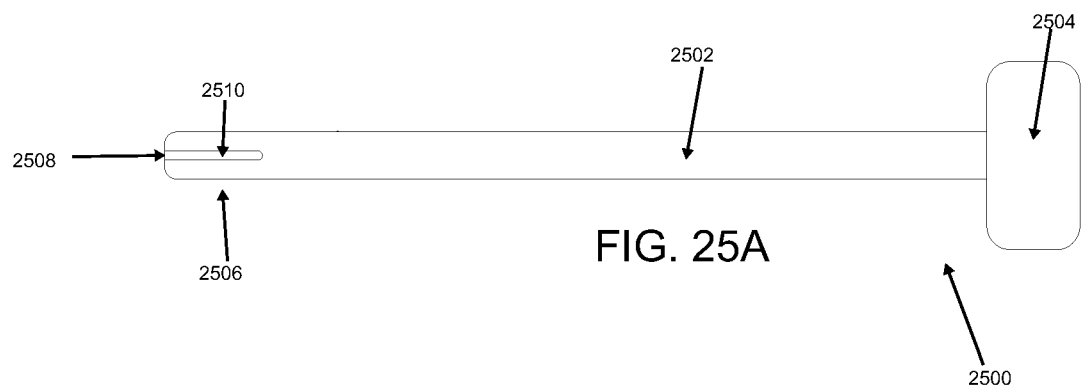
FIGS. 25A and 25B are superior and anterior elevational views of one embodiment of a needle driver.
Figure 25B:
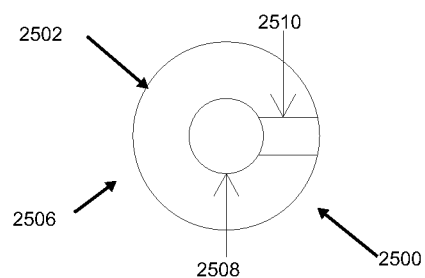

Referring to FIGS. 25A and 25B, in some embodiments, to facilitate the manipulation and use of needles during the implantation procedure, a needle driver 2500 may be provided. In some embodiments, the needle driver 2500 may permit improved control and/or force application compared to pair of needle forceps, as the driver shaft 2502 of the driver 2500 may be aligned with the direction of force application. In contrast, a needle held by a pair of needle forceps is often oriented transversely or skewed with respect to the clamp members of the forceps, and therefore lacks the direct force transfer and stability of a needle driver as depicted in FIG. 25A. As illustrated, the needle driver 2500 may comprise a proximal handle 2504 from which the driver shaft 2502 distally extends. The distal end 2506 of the driver shaft 2502 comprises a longitudinal lumen 2508 which is configured to regain the proximal end of a needle, such as the suture coupling section 2412 of the needle 2400 depicted in FIG. 24. The lumen 2508 is typically configured to retain at least a portion the suture 2402 attached to the needle 2400. The lumen 2508 may comprise one or more optional side slots 2510 or openings to permit the suture 2402 to emerge from the driver shaft 2502. In some embodiments, the side slot(s) 2510 may permit the walls of the lumen 2508 to expand outward, particularly for but not limited to when the needle 2400 is inserted into the lumen 2508. In embodiments where the lumen 2508 is expandably configured to retain the proximal end of the needle 2400 and suture 2402, frictional resistance from the compressive forces acting on the needle may further facilitate retention of the needle 2400 by the needle driver 2500. In other embodiments, a releasable clamp, retaining pin assembly or other active holding mechanism may be provided on the needle driver to releasably hold the needle 2400.

Figure 26:
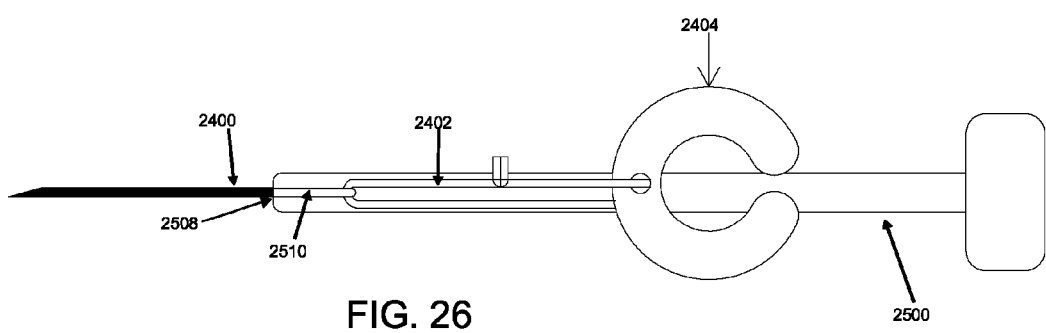
FIG. 26 is a superior elevational view of the needle driver of FIG. 25A loaded with the orthopedic device of FIG. 24.

FIG. 26 depicts the needle driver 2500 of FIG. 25 with the needle 2400 of FIG. 24 inserted into its lumen and with the suture loop 2402 located in the side slot 2510. As depicted, the suture loop 2402 and the orthopedic device 2404 are not attached to the driver 2500 and are freely mobile. In some embodiments, in use, the suture loop 2402 and the orthopedic device 2404 may dangle from the driver 2500, or may be held in place by the surgeon in the same hand used to hold and manipulate the driver 2500.

Figure 27:
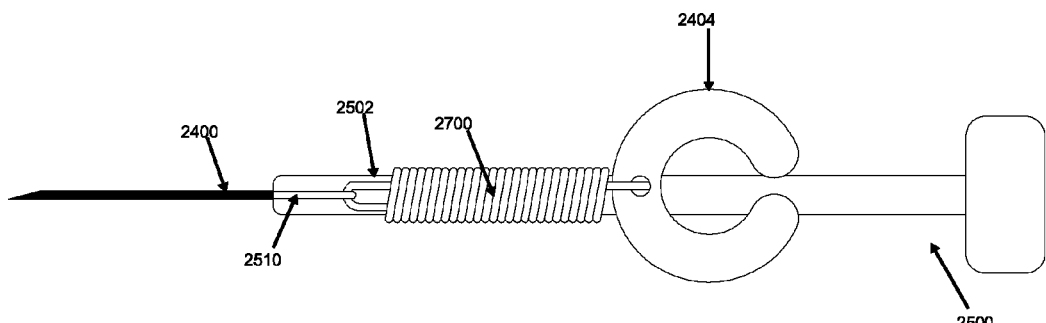
FIG. 27 is a superior elevational view of the needle driver of FIG. 25A loaded with an embodiment of an orthopedic device with a coiled suture.

FIG. 27 depicts the needle driver 2500 of FIG. 25 loaded with the needle 2400 of FIG. 24, but with a longer suture loop 2700 attaching the orthopedic device 2404 and the needle 2400. As shown in FIG. 27, the longer suture loop 2700 may be wrapped along the length of the driver shaft 2502 to retain at least some loose length of suture loop 2700. Depending on the manner with which the suture loop 2700 is wrapped, the extent with which the orthopedic device 2404 may dangle or hang during the procedure may also be reduced. In use, the needle driver 2500 with loaded needle 2400 is inserted through the affected joint until the needle 2400 is accessible on the opposite side of the joint. In one embodiment, the needle driver 2500 may be held in place as the needle 2400 is pulled out of the body. As the needle 2400 is pulled, the coiled suture loop 2700 may be unraveled and may be pulled out along with the needle 2500. In some embodiments, once the needle 2400 is accessible on the opposite side of the joint, the needle driver 2500 may be withdrawn, leaving an unsupported coil of the suture loop 2700 in the patient, which is then pulled out using the needle 2400 or portion of the suture loop 2700 connected to the needle 2400.

Figure 28A:
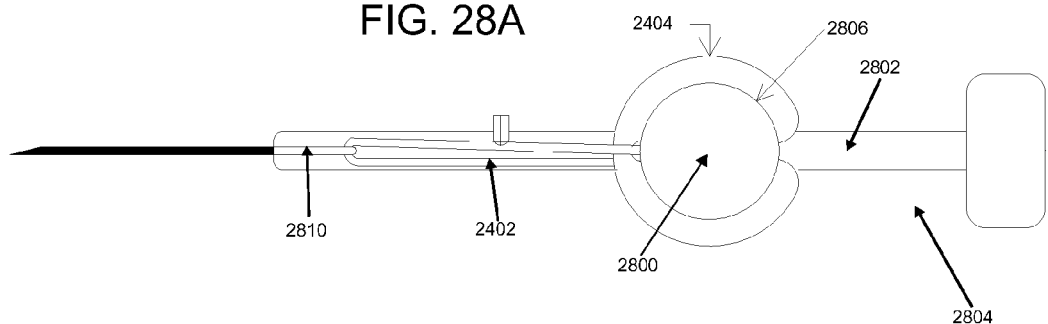
FIGS. 28A and 28B are superior elevational and side cross-sectional views of another embodiment of a needle driver with a flanged mount and loaded with the orthopedic device of FIG. 24.
Figure 28B:
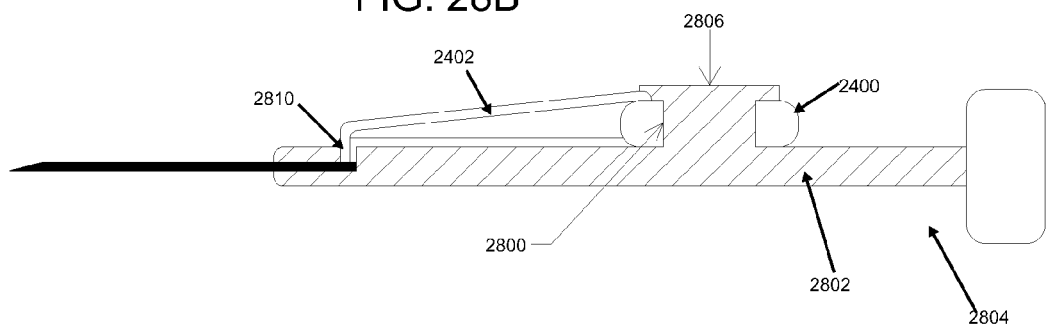
Figure 29:
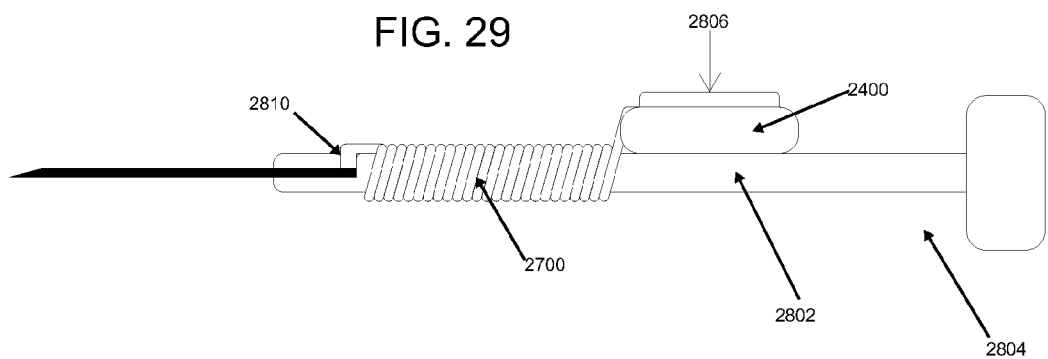
FIG. 29 is a side elevational view of the needle driver in FIG. 28A loaded with the orthopedic device of FIG. 27.

In other embodiments, the needle driver may include one or more other retaining structures to releasably hold the suture loop and/or the orthopedic device during the implantation procedure. The retaining structures may include but are not limited to hooks, clamps, clips, latches, posts, slots, recesses, cavities and other structures which may be used to retain one or more portion of the suture loop and/or the orthopedic device. In FIGS. 28A and 28B, for example, the "C"-shape orthopedic device 2404 may be resiliently and releasably clipped to a post or drum 2800 located on the driver shaft 2802 of the needle driver 2804. In this particular embodiment, the drum 2800 further comprises a flange 2806 that may resist slippage of the orthopedic device 2404 off of the drum 2800. As shown in FIG. 28A, the drum 2800 may be positioned on the driver shaft 2802 in generally circumferential alignment with the slot 2810 of the driver shaft 2800. In some embodiments, this alignment may facilitate the release of the orthopedic device 2404 from the drum 2800 by providing a direct pulling vector along the suture loop 2402 from the needle 2400 to the orthopedic device 2404. In other embodiments, the drum 2800 may be located out of alignment with respect to the slot 2810 of the driver shaft 2800, and/or one or more coils of suture loop 2402 may be wound onto the driver shaft 2500. FIG. 29, for example, depicts the needle driver 2804 of FIG. 28A is loaded with the needle 2400, orthopedic device 2404 and suture loop 2700 from FIG. 27, where the excess portions of the suture loop 2700 have been releasably coiled onto itself and the driver shaft 2802 of the needle driver 2804.

FIGS. 30A to 32B illustrate one embodiment of an implantation method involving an orthopedic device 2900 and a needle driver 2902. The joint 2904 depicted in FIGS. 30A to 32B is a schematic representation of a metacarpal-phalangeal (MCP) joint 2904 formed between a proximal phalanx Ph and its associated metacarpal MC and enclosed by a joint capsule JC, but in other embodiments, may be schematically illustrative of a variety of joints that may be treated in a medical or veterinary setting. In some embodiments, the orthopedic device 2900 may be inserted on an out-patient basis using only local or regional anesthesia, but in other embodiments, general anesthesia may be used. Depending upon whether the various components of the procedure are provided in pre-attached form or not, the needle 2906, suture 2908 and orthopedic device 2900 may be attached as needed and loaded into the needle driver 2902. In some embodiments, the orthopedic device 2900 may be provided in sealed, pre-hydrated packaging, but in other embodiments, the orthopedic device 2900 may be soaked in a saline or other type of liquid for about 5 minutes to about 15 or about 30 minutes before being coupled to the suture 2908 and/or needle 2906, if not already coupled or pre-coupled. The patient's affected hand is prepped and draped in the usual sterile fashion. The MCP joint is identified on the dorsal and palmar (or other proximal and distal) surfaces of the affected region, with or without finger flexion or traction. A dorsal transverse incision is made across the joint. In some embodiments, the incision is made using a scalpel, but in other embodiments, the penetrating tip of the needle driver 2902 may comprise a spatula or spade cutting tip, which may be oriented to achieve a transverse incision. In some alternate embodiments, a longitudinal incision or stab incision may be used instead, and/or the incision may be initiated on the palmar side of the MCP joint, or from the lateral or medial aspect of the MCP joint, taking care not to injure any of the digital nerves of the fingers. The connective tissue is optionally dissected if desired until the joint capsule of the MCP joint is identified.

Figure 30A:
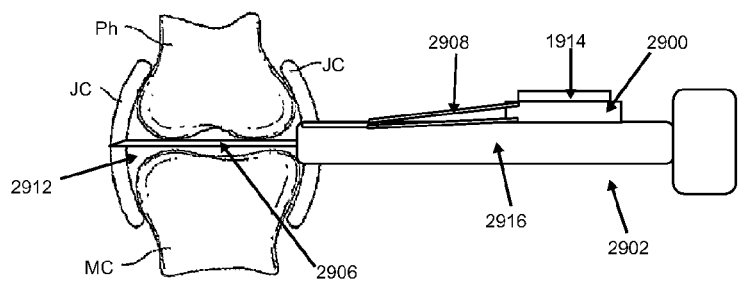
Figure 30B:
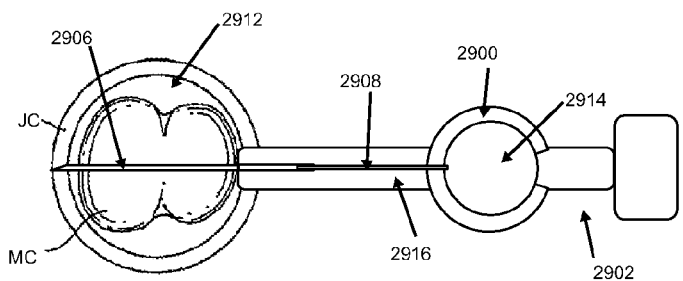
FIGS. 30B, 31B and 32B are the corresponding superior cutaway views, respectively.
Figure 31A:
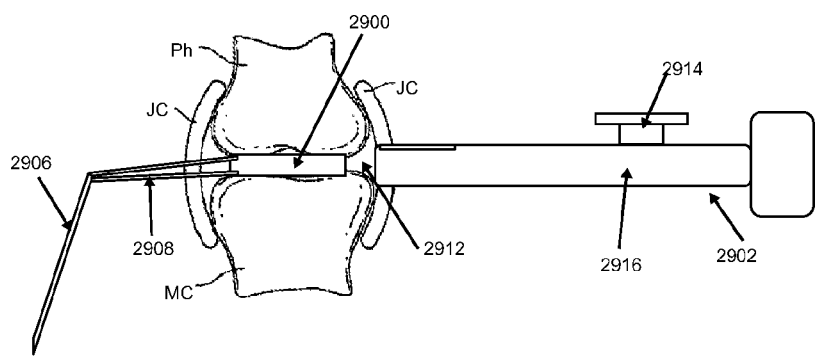
Figure 31B:
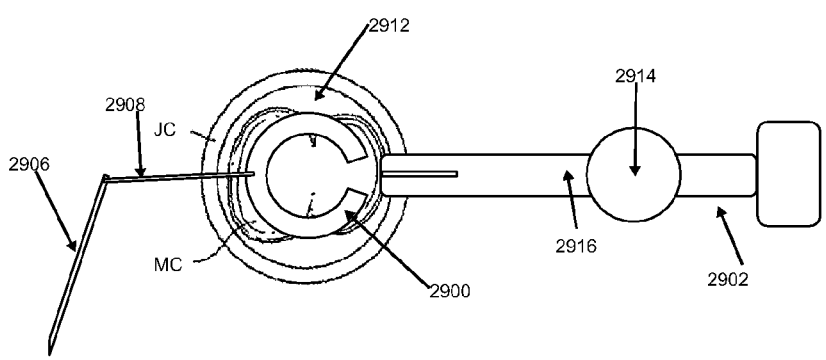
Figure 32A:
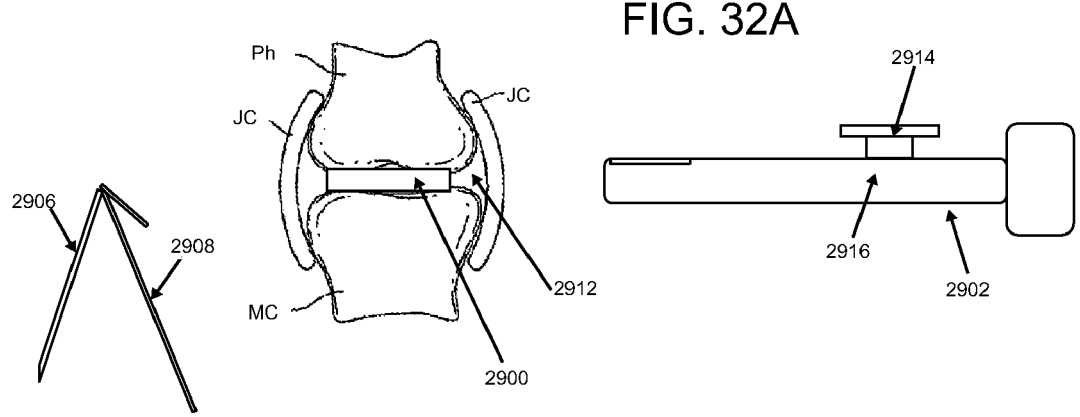
Figure 32B:
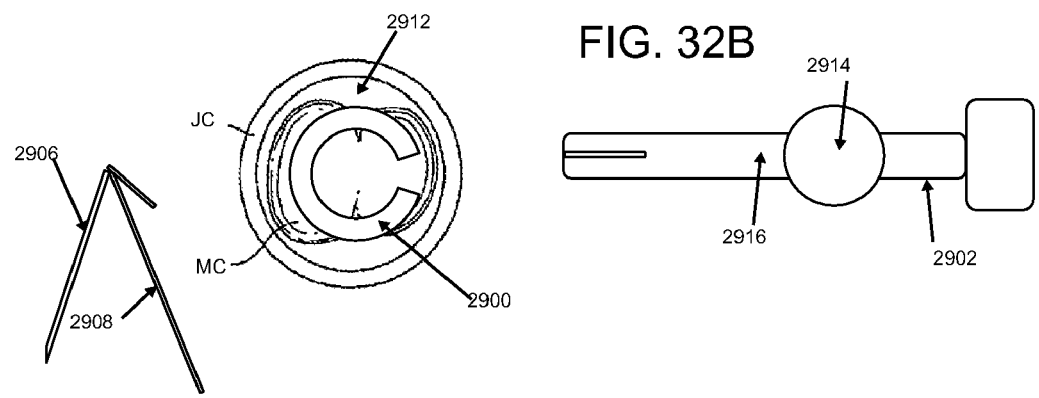

As shown in FIGS. 30A and 30B, the loaded needle driver 2902 may be inserted through the joint capsule JC. The needle driver 2902 may be directed across the joint space 2912 until the opposing side of the joint capsule JC is penetrated and the needle 2906 may be accessed. Referring to FIGS. 31A and 31B, forceps or other type of grasping instrument may be used to engage the protruding needle 2906 and is further pulled out and/or away from the joint 2904. The needle driver 2902 may be braced or stabilized as the suture 2908 is tensioned and begins to pull the orthopedic device 2900. The orthopedic device 2900 may be pulled away from the retaining post 2914 of the driver shaft 2916, through the joint capsule JC and into the joint space 2912. Depending upon the method used to achieve joint access, the orthopedic device 2900 may collapse or pinch inward as the orthopedic device passes through the joint capsule JC and then expands as the orthopedic device 2900 emerges from joint capsule JC and into the joint space 2912. The seating or positioning of the orthopedic device 2900 in the joint space may be checked by tactile response to tensioning the suture 2908 and/or by fluoroscopy or arthroscopy, for example. Once the desired positioning of the orthopedic device 2900 is confirmed, the joint range of motion may be checked, along with joint loading to check for joint crepitus or locking. As depicted in FIGS. 32A and 32B, one or both suture lines 2908 exposed on the palmar side of the joint may be cut or severed and then pulled out to separate from the orthopedic device. In some embodiments, closure of the initial incision is not required due to the small size of the incision, but in other embodiments, about one to about three small stitches may be applied using 4-0 or 5-0 non-resorbable sutures, for example, to close the incision. The skin incision, if any, may be closed using sutures, staples or tissue adhesives. The range of motion is optionally rechecked again, and the incision may then be dressed or splinted as determined by the surgeon.

It will be understood that the foregoing is only illustrative of the principles of the invention, and that various modifications, alterations, and combinations can be made by those skilled in the art without departing from the scope and spirit of the invention. Any of the embodiments of the various orthopedic devices disclosed herein can include features described by any other orthopedic devices or combination of orthopedic devices herein. Furthermore, any of the embodiment of the various orthopedic device delivery and/or retrieval systems can be used with any of the orthopedic devices disclosed, and can include features described by any other orthopedic device delivery and/or retrieval systems or combination of orthopedic device delivery and/or retrieval systems herein. Accordingly, it is not intended that the invention be limited, except as by the appended claims. For all of the embodiments described above, the steps of the methods need not be performed sequentially.

What is claimed as new and desired to be protected by Letters Patent of the United States is:

1. A method of implanting an orthopedic device in a patient, comprising:
  inserting a needle through a first joint capsule opening of a joint space located at a dorsal side of a carpo-metacarpal joint;
  passing the needle with an attached suture across the joint space and piercing through tissue to form a second joint capsule opening located at an opposite palmar side of the carpo-metacarpal joint, wherein the second joint capsule opening is smaller than the first joint capsule opening;

pulling a resilient orthopedic device into the joint space using the suture, wherein the resilient orthopedic device comprises a first end, a second end, and a body therebetween having an elongate arcuate configuration;

separating at least a portion of the suture from the resilient orthopedic device; and removing at least a portion of the suture from the patient.

2. The method of claim 1, further comprising abutting the resilient orthopedic device against the second joint capsule opening.

3. The method of claim 1, further comprising positioning the resilient orthopedic device symmetrically within the joint space with respect to the second joint capsule opening.

4. The method of claim 1, further comprising restraining the resilient orthopedic device in a reduced profile as the resilient orthopedic device traverses the first joint capsule opening.

5. The method of claim 4, further comprising enlarging the resilient orthopedic device from a reduced profile to an enlarged profile with substantially the same volume as the orthopedic device in the reduced profile.

6. The method of claim 4, further comprising enlarging the resilient orthopedic device from a reduced profile to an enlarged profile with substantially the same mass as the orthopedic device in the reduced profile.

7. The method of claim 1, further comprising restraining the resilient orthopedic device in a delivery configuration as the resilient orthopedic device traverses the first joint capsule opening.

8. The method of claim 7, further comprising releasing the resilient orthopedic device from the delivery configuration in the joint space to assume an implantation configuration that is non-linear.

9. The method of claim 8, wherein a distance between the first end and the second end of the resilient orthopedic device in the delivery configuration is greater than the distance between the first end and the second end of the resilient orthopedic device in the implantation configuration.

10. The method of claim 8, wherein the implantation configuration comprises at least one arcuate section.

11. The method of claim 8, wherein the implantation configuration is a generally a non-planar implantation configuration.

12. The method of claim 1, wherein the resilient orthopedic device is pre-coupled to the suture at the point-of-manufacture.

13. The method of claim 1, wherein a needle path between the between the first joint capsule opening and the second joint capsule opening is straight.

14. The method of claim 1, wherein the resilient orthopedic device comprises a C-shaped body surrounding a span member, and a gap between two ends of the C-shaped body.

* * * * *